US005679511A

United States Patent [19]
Kwon

[11] Patent Number: 5,679,511
[45] Date of Patent: Oct. 21, 1997

[54] CDNA CLONES FOR A REGULATORY PROTEIN IN THE MELANIN-PRODUCTION PATHWAY

[75] Inventor: Byoung Se Kwon, Carmel, Ind.

[73] Assignees: Donald Guthrie Foundation for Medical Research, Inc., Sayre, Pa.; Indiana University Foudation, Bloomington, Ind.

[21] Appl. No.: 891,942

[22] Filed: Jun. 1, 1992

Related U.S. Application Data

[60] Continuation-in-part of Ser. No. 362,847, Jun. 7, 1989, abandoned, which is a division of Ser. No. 915,753, Oct. 6, 1986, Pat. No. 4,898,814.

[51] Int. Cl.$^6$ .................... C12Q 1/68; C12N 15/70; C12N 15/11; C07K 14/00
[52] U.S. Cl. .................... 435/6; 435/320.1; 530/350; 536/23.2; 536/23.5
[58] Field of Search .................... 536/23.2, 23.5; 435/320.1, 6; 530/350

[56] References Cited

PUBLICATIONS

Houghton et al., J. Exp. Med., vol. 156, pp. 1755–1766 (1982).
Gown et al., Am. J. Pathology, vol. 123, pp. 195–203 (1986).
Deranlowicz et al., Neoplasma, vol. 27 No. 4.
Chang et al., J. Invest. Dermatol. vol. 87 No. 3.
Tomita et al., Diag. Immunol., vol. 4, No. 3.
Vachtenheim et al., J. Invest. Dermatol., vol. 86 No. 3.
Shibahara et al., Nucl. Acids Res., vol. 14, No. 6, pp. 2413–2427 (1986).
Old, Princ. of Gene Manipul., Blackwell Sci. Publ., 3rd ed. pp. 9–10 (1985).
Coleman, D., Effect of Genic Substitution on the Incorporation of Tyrosinase into the Melanin of Mouse Skin, (1962) Arch. Biochem. Biophys., pp. 69, 562–568.
Gluecksohn–Waelsch, S., "Genetic Control of Morphogenetic and Biochemical Differentiation: Lethal Albino Deletions in the Mouse", (1979) Cell, 16, 225–227.
Halaban, S. H., "Selective Elimination of Fibroblasts From Cultures of Normal Human Melanocytes", (1984) In Vitro, 20, pp. 447–450.
Halaban, R. et al, "Human Melanocytes Cultured from Nevi and Melanomas", (1986), Jou. of Invest. Dermatoloqy, 87, pp. 95–101.
ROSS, R.A et al, "Expression of a Melanocyte Phenotype in Human Neuroblastoma Cells In Vitro", (1985), Adv. In Neuroblastoma, pp. 249–255.
Chirgwin, J. et al., "Isolation of Biologically Active Ribonucleic Acid from Sources Enriched in Ribonuclease", 1979, Biochem. 18, pp. 5294–5299.
Aviv, H. et al, "Purification of Biologically Active Globin Messenger RNA by Chromatography on Oligothymidylic acid–Cellulose" (1972) Proc. Natl. Acad. Sci. USA 69, 1408–1412.

Thomas, P., "Hybridization of denatured RNA and small DNA fragments transferred to nitrocellulose", 1980 Proc. Natl. Acad. Sci, USA 77, 5201, 5205.
Gross–Bellard, M. et al., "Isolation of High–Molecular–Weight DNA from Mammalian Cells", (1973) Eur. J.Biochem., 36, pp. 32–38.
Sanger, F. et al, "DNA sequencing with chain–terminating inhibitors", 1977, Proc. Natl. Acad. Sci. USA, 74, pp. 5463–5467.
Biggin, M. et al., "Buffer gradient gels and 35S label as an aid to rapid DNA sequence determination", 1983 Proc. Natl Acad. Sci. USA, 80, pp. 3963–3965.
Goeddel, D. et al, "The structure of eight distinct cloned human leuckoyte interferon cDNAs", 1981, Nature (London) 290, 20–26.
Steiner, D. et al, "Processing Mechanisms in the Biosynthesis of Proteins" 1980, Ann. N.Y. Acad. Sci., 343, pp. 1–16.
Marshall, R., "The Nature and Metabolism of the Carbohydrate–Peptide Linkages of Glycoproteins",1974, Biochem. Soc. Symp. 40, pp. 17–26.
Richardson, J. et al., "Crystal Structure of Bovine Cu, Zn superoxide Dismutase at 3 A Resolution: Chain Tracing and Metal Liquids", 1975, Proc. Natl. Acad. Sci. USA, 72, pp. 1340–1353.
Mason, H., "The Mechanism of The Oxidation of Dihydroxyphenylalanine by Tyrosinase", 1948, J. Bio. Chm. 172, pp. 83–99.
Land, H. et al, "Terminal sequences of eucaryotic mRNA can be cloned with high efficiency", 1981, Nucl. Acid. Res., 9, pp. 2251–2261.
Young, R. et al, "Efficient isolation of genes by using antibody probes", 1983, Proc. Natl. Acad. Sci. 80, pp. 11194–1198.
Blobel, G. et al, "Transfer of Proteins Across Membranes", 1975 J. Cell Biol. 67, pp. 852–862.

(List continued on next page.)

*Primary Examiner*—Nancy T. Vogel
*Attorney, Agent, or Firm*—Barnard, Brown & Michaels

[57] ABSTRACT

The present invention started when a λgt11 cDNA library of normal human melanocytes was screened with antibodies directed against purified hamster tyrosinase. Two important cDNA clones were isolated: cDNA λmel 34 and λmel 17-1. It is concluded that λmel 34 contained cDNA encoding human tyrosinase. Moreover, the cDNA gene for human tyrosinase was recovered from the λmel 34 and can be used for many purposes including the production of pure human tyrosinase. This gene and its promoter are characterized herein. Studies suggested that λmel 17-1 gene product act on melanin biosynthesis's pathway distal to tyrosinase. Melanocytes preferentially express an mRNA species, Pmel 17, whose protein product cross reacted with anti-tyrosinase antibodies and whose expression correlated with the melanin content. The deduced protein structure has been analyzed and its chromosomal location in mouse and man has been mapped. The human Pmel 17 gene, designated D12S53E, maps to Chromosome 12, region 12pter-q21; and the mouse homologue, designated D12S53Eh, maps to the distal region of mouse Chromosome 10, a region also known to carry the coat color locus si (silver).

6 Claims, 25 Drawing Sheets

OTHER PUBLICATIONS

Bause, E., "Structural requirement so f N-glycosylation of proteins", 1983 Biochem. J., 209, pp. 331–336.

Nishioka, K., "Particulate Tyrosinase of Human Malignant Melanoma 1978", Eur. J. Biochem., 85, pp. 137–146.

Lerch, J., "An Epr Study of Neurospora Tyrosinase", 1976, FEBS Lett, 69, pp. 161–164.

Messing, J. et al, "A system for shotgun DNA sequencing" 1981, Nucleic Acids Res. 9, pp. 309–322.

Beermann, F. et al., Rescue of albino phenotype by introduction of a functional tyrosinase gene into mice, 1990, EMBO J., 9:2819–2826.

Charthew, R. et al, An RNA polymerase II transcription factor binds to an upstream element in the adenovirus major late promoter, 1985, Cell., 43: 439–448.

Green, M.C., (1961) Journal of Heredity, 52, 73–75.

Kidson, S.H. et al, 1981, Journal of Exp. Zoology 215, 91–97.

Southern, E.,–1975–J. Mol. Biol. 87, 503–517.

Biossy, R. et al, 1986, J. of Investigative Dermatology, 88, 292–300.

Witkop, C. Jr., 1984, The Clinics in Dermatology, vol.2, 70–134.

Halaban, R. et al., 1983, J. Cell Biol., 97, 480–488.

Mehra, V. et al., 1986, Proc. Natl. Acad. Sci. USA 83, 7013–7017.

Shibahara, S. 1987, Advance in Pigment Cell Research, pp. 263–271.

Kwon, et al, Isolation and initial characterization of multiple species of T-lymphocyte subset cDNA clones, Pro. Natl. Acad. Sci USA, Vo. 84. pp. 2896–2900, May 1987.

Yamamoto et al, Cloning and sequencing of mouse tyrosianse cDNA, Jpn, J. Genet. (1987) 62, pp. 271–274.

Shibahara, S. et al., Cloning and expression of cDNA encoding mouse tyrosinyase, IRL Press Limited, Oxford, GB., pp. 2413–2427.

Chodosh, L. et al., "A single polypeptide possess the binding and transcription activities of the adenovirus major late transcription factor" 1986, Mol. Cell. Biol., 6:4723–4733.

Dignam, J. et al, "Accurate transcription initiation by RNA Polymerase II in a soluble extract from isolated mammalian nuclei", 183, Nucleic. Acids. Res., 11: 1475–1489.

Emerson, B. et al., "Interaction of specific nuclear factors with the nuclease-hypersensitive region of the chicken adult β-globin gene", 1985, Cell. 41:21–30.

Kadonaga, J. et al., "Affinity purification of sequence-specific DNA binding proteins", 1986 Proc. Natl. Acad. Sci. USA, 83:5889–5893.

Kluppel, M. et al., "The mouse tyrosinase promoter is sufficient for expression in melanocytes and in the pigmented epithelium of the retina", 1991, Proc. Natl. Acad. Sci. USA., 88:3777–3781.

Kwon, B. et al., "Sequence analysis mouse tyrosinase cDNA and the effects of melanotropin on its gene expression", 1988, Biochem. Biophys. Res. Comm., 153:1301–1309.

Kwon, B. et al., "Isolation, chromosomal mapping and expression of the mouse tyrosinase gene", 1989 J. Invest. Dermotol., 93:589–594.

Muller, G. et al, "Functional analysis of alternatively spliced tyrosinase gen transcripts", 1988 EMBO J., 7:2723–2730.

Yokoyama, T. et al, "Conserved cysteine to serine, mutation in tyrosinase is responsible for the classical albino mutation in laboratory mice", 1990, Nucleic. Acids. Res., 18:7293–7298.

Barton, D. et al., "Human tyrosinase gone mapped to chromosome 11(q14–q21) defines second region of homology with mouse chromosome 7", 1988, Genomics. 3:17–24.

Bouchard, B. et al, "Induction of pigmentation in mouse fibroblasts by expression of human tyrosinase cDNA", 1989 J. Exp. Med. 169:2029–2042.

Chintamaneni, C. et al., "A single base insertion in the putative transmembrane domain of the tyrosinase gene as cause for tyrosinase-negative oculocutaneous albinism", 1991, Proc. Natl. Sci. USA, 88:5272–5276.

Giebel, L. et al., "Organization and nucleotide sequence of the human tyrosinase gene and a truncated tyrosinase-related segment", 1919, Genomics., 9:435–445.

Halaban, R. et al., "The dual effect of melanocyte-stimulating hormone (MSH) on the growth of cultured mouse melanoma cells", 1977, Exp. Cell. Res. 108:111–117.

Halaban, R. et al., "Tyrosinase activity and abundance in cloudman melanoma cells", 1984 Arch. Biochem. Biophys. 230:383–387.

Kwon, B. et al., "Isolation and sequence of a cDNA for human tyrosinase that maps at the mouse c–albino locus", 1987 Proc. Natl. Acad. Sci. USA 84:7473–7477.

Lee, W. et al., "Activation of transcription by two factors that bind promoter and enhancer sequences of the human metallothionein gene and SV40", 1987, Nature. 325:368–372.

Ruppert, S. et al., "Multiple transcripts of the mouse tyrosinase gene are generated by alternative splicing", 1988, EMBO.J. 7:2715–2722.

Shibahara, S. et al., "Molecular basis for the heterogeneity of human tyrosinase", 1988, Tohuka. J. Exp. Med. 156:403–414.

Spritz, R. et al., "Detection of tyrosinase gene mutations in a patient with type IA oculocutaneous albinism", 1990 N. Eng. J. Med. 322:1724–1728.

Takeda, A. et al., "Functional analysis of the cDNA encoding human tyrosinase precursor", 1989, Biochem. Biophys. Res. Commun. 162:984–990.

Tomita, Y. et al., "Human oculocutaneous albinism causes by single base insertion in the tyrosinase gene", 1989 Biochem. Biophys. Res. Commun. 164:990–996.

Giebel, L. et al., 1990, Proc. Natl. Acad. Sci. USA, 87:3255–3258.

Kwon, B. et al., 1987, Mol. Biol. Md., 4:339–355.

Francke, U. et al., 1986, Cold Spring Harbor Symposia on Quantitative Biology, 51:855–866.

Yang-Feng, T. et al., 1986 Proc. Natl. Acad. Sci. USA, 83:8679–8683.

Shaw, A. et al., 1990, Mol. Cell. Biol., 10:1853–1862.

Halaban, R. et al., 1990, Proc. Natl. Acad. Sci. USA, 87:4809–4813.

Kwon, B. et al., Oct. 1991, Proc. Natl. Acad. Sci. USA, 88:9228–9232.

Gaulton., G. et al., 1983, Contolf of Tyrosinase Gene Expression and Its Relationship to Neural Crest Induction in Rana Pipiens, J. of Biol. Chem., vol. 258, No. 24, 14845–14849.

Houghton, A. et al., 1982, Surface Antigens of Melanocytes and Melanomas, J. Exp. Med., 156:1755–1766.

Jackson, I., 1988, A cDNA encoding tyrosinase-retlated proteins maps to the brown locus in mouse, Proc. natl. Acad. Sci. USA, 85:4392–4396.

Pawwlek, J. et al, 1974, Proc. Nat. Acad. Sci. USA, vol. 71 No: 4, 1073–1077, Genetic Control of Melanization: Isolation and Analysis Amelanotic Variants from Cultured Melanotic Melanoma Cells.

```
-40              -30              -20              -10              -1 1              10
GAA TTC CTG CTC CTG GCT GTT TTG TAC TGC CTG CTG TGG AGT TTC CAG ACC TCC GCT GGC
--------Leu Leu Leu Ala Val Leu Tyr Cys Leu Leu Trp Ser Phe Gln Thr Ser Ala Gly
EcoRl            -10                                      -1   1

20               30               40               50               60               70
CAT TTC CCT AGA GCC TGT GTC TCC TCT AAG AAC CTG ATG GAG AAG GAA TGC TGT CCA CCG
His Phe Pro Arg Ala Cys Val Ser Ser Lys Asn Leu Met Glu Lys Glu Cys Cys Pro Pro
                 10                                       20

80               90               100              110              120              130
TGG AGC GGG ACA GGA GTC TGT GGC CAG CTT TCA GGC AGA GGT TCC TGT CAG AAT ATC CTT
Trp Ser Gly Thr Gly Val Cys Gly Gln Leu Ser Gly Arg Gly Ser Cys Gln Asn Ile Leu
                 30                                       40

140              150              160              170              180              190
CTG TCC AAT GCA CCA CTT GGG CCT CAA TTT CCC TTC ACA GGG GTG GAT GAC CGG GAG TCG
Leu Ser Asn Ala Pro Leu Gly Pro Gln Phe Pro Phe Thr Gly Val Asp Asp Arg Glu Ser
                 50                                       60

200              210              220              230              240              250
TGG CCT TCC GTC TTT TAT AAT AGG ACC TGC CAG TGC TCT GGC AAC TTC ATG GGA TTC AAC
Trp Pro Ser Val Phe Tyr Asn Arg Thr Cys Gln Cys Ser Gly Asn Phe Met Gly Phe Asn
                 70                                       80

260              270              280              290              300              310
TGT GGA AAC TGC AAG TTT GGC TTT TGG GGA CCA AAC TGC ACA GAG AGA CGA CTC TTG GTG
Cys Gly Asn Cys Lys Phe Gly Phe Trp Gly Pro Asn Cys Thr Glu Arg Arg Leu Leu Val
                 90                                       100

320              330              340              350              360              370
AGA AGA AAC ATC TTC GAT TTG AGT GCC CCA GAG AAG GAC AAA TTT TTT GCC TAC CTC ACT
Arg Arg Asn Ile Phe Asp Leu Ser Ala Pro Glu Lys Asp Lys Phe Phe Ala Tyr Leu Thr
                 110                                      120

380              390              400              410              420              430
TTA GCA AAG CAT ACC ATC AGC TCA GAC TAT GTC ATC CCC ATA GGG ACC TAT GGC CAA ATG
Leu Ala Lys His Thr Ile Ser Ser Asp Tyr Val Ile Pro Ile Gly Thr Tyr Gly Gln Met
                 130                                      140

440              450              460              470              480              490
AAA AAT GGA TCA ACA CCC ATG TTT AAC GAC ATC AAT ATT TAT GAC CTC TTT GTC TGG ATG
Lys Asn Gly Ser Thr Pro Met Phe Asn Asp Ile Asn Ile Tyr Asp Leu Phe Val Trp Met
        150                                       160
```

FIG. 6A

```
500         510         520         530         540         550
CAT TAT TAT GTG TCA ATG GAT GCA CTG CTT GGG GGA TAT GAA ATC TGG AGA GAC ATT GAT
His Tyr Tyr Val Ser Met Asp Ala Leu Leu Gly Gly Tyr Glu Ile Trp Arg Asp Ile Asp
                        170                     180
560         570         580         590         600         610
TTT GCC CAT GAA GCA CCA GCT TTT CTG CCT TGG CAT AGA CTC TTC TTG TTG CGG TGG GAA
Phe Ala His Glu Ala Pro Ala Phe Leu Pro Trp His Arg Leu Phe Leu Leu Arg Trp Glu
                        190                     200
620         630         640         650         660         670
CAA GAA ATC CAG AAG CTG ACA GGA GAT GAA AAC TTC ACT ATT CCA TAT TGG GAC TGG CGG
Gln Glu Ile Gln Lys Leu Thr Gly Asp Glu Asn Phe Thr Ile Pro Tyr Trp Asp Trp Arg
                        210                     220
680         690         700         710         720         730
GAT GCA GAA AAG TGT GAC ATT TGC ACA GAT GAG TAC ATG GGA GGT CAG CAC CCC ACA AAT
Asp Ala Glu Lys Cys Asp Ile Cys Thr Asp Glu Tyr Met Gly Gly Gln His Pro Thr Asn
                        230                     240
740         750         760         770         780         790
CCT AAC TTA CTC AGC CCA GCA TCA TTC TTC TCC TCT TGG CAG ATT GTC TGT AGC CGA TTG
Pro Asn Leu Leu Ser Pro Ala Ser Phe Phe Ser Ser Trp Gln Ile Val Cys Ser Arg Leu
                        250                     260
800         810         820         830         840         850
GAG GAG TAC AAC AGC CAT CAG TCT TTA TGC AAT GGA ACG CCC GAG GGA CCT TTA CGG CGT
Glu Glu Tyr Asn Ser His Gln Ser Leu Cys Asn Gly Thr Pro Glu Gly Pro Leu Arg Arg
                        270                     280
860         870         880         890         900         910
AAT CCT GGA AAC CAT GAC AAA TCC ACA ACC CCA AGG CTC CCC TCT TCA GCT GAT GTA GAA
Asn Pro Gly Asn His Asp Lys Ser Thr Thr Pro Arg Leu Pro Ser Ser Ala Asp Val Glu
                        290                     300
920         930         940         950         960         970
TIT TGC CTG AGT TTG ACC CAA TAT GAA TCT GGT TCC ATG GAT AAA GCT GCC AAT TTC AGC
Phe Cys Leu Ser Leu Thr Gln Tyr Glu Ser Gly Ser Met Asp Lys Ala Ala Asn Phe Ser
                        310                     320
980         990         1000        1010        1020        1030
TTT AGA AAT ACA CTG GAA GGA TTT GCT AGT CCA CTT ACT GGG ATA GCG GAT GCC TCT CAA
Phe Arg Asn Thr Leu Glu Gly Phe Ala Ser Pro Leu Thr Gly Ile Ala Asp Ala Ser Gln
                        330                     340
```

FIG. 6B

```
1040        1050        1060        1070        1080        1090
AGC AGC ATG CAC AAT GCC TTG CAC ATC TAT ATG AAT GGA CAT GTC CCA GGT ACA GGA TCT
Ser Ser Met His Asn Ala Leu His Ile Tyr Met Asn Gly His Val Pro Gly Thr Gly Ser
                        350                                 360
1100        1110        1120        1130        1140        1150
GCC AAC GAT CCT ATC TTC CTT CTT CAC CAT GCA TTT GTT GAC AGT ATT TTT GAG CAG TGG
Ala Asn Asp Pro Ile Phe Leu Leu His His Ala Phe Val Asp Ser Ile Phe Glu Gln Trp
                        370                                 380
1160        1170        1180        1190        1200        1210
CTC CAA AGG CAC CGT CCT CTT CAA GAA GTT TAT CCA GAA GCC AAT GCA CCC ATT GGA CAT
Leu Gln Arg His Arg Pro Leu Gln Glu Val Tyr Pro Glu Ala Asn Ala Pro Ile Gly His
                        390                                 400
1220        1230        1240        1250        1260        1270
AAC CGG GAA TCC TAC ATG GTT CCT TTT ATA CCA CTG TAC AGA AAT GGT GAT TTC TTT ATT
Asn Arg Glu Ser Tyr Met Val Pro Phe Ile Pro Leu Tyr Arg Asn Gly Asp Phe Phe Ile
                        410                                 420
1280        1290        1300        1310        1320        1330
TCA TCC AAA GAT CTG GGC TAT GAC TAT AGC TAT CTA CAA GAT TCA GAC CCA GAC TCT TTT
Ser Ser Lys Asp Leu Gly Tyr Asp Tyr Ser Tyr Leu Gln Asp Ser Asp Pro Asp Ser Phe
                        430                                 440
1340        1350        1360        1370        1380        1390
CAA GAC TAC ATT AAG TCC TAT TTG GAA CAA GCG AGT CGG ATC TGG TCA TGG CTC CTT GGG
Gln Asp Tyr Ile Lys Ser Tyr Leu Glu Gln Ala Ser Arg Ile Trp Ser Trp Leu Leu Gly
                        450                                 460
1400        1410        1420        1430        1440        1450
GCG GCG ATG GTA GGG GCC GTC CTC ACT GCC CTG CTG GCA GGG CCT GTG AGC TTG CTG TGT
Ala Ala Met Val Gly Ala Val Leu Thr Ala Leu Leu Ala Gly Pro Val Ser Leu Leu Cys
                        470                                 480
1460        1470        1480        1490        1500        1510
CGT CAC AAG AGA AAG CAG CTT CCT GAA GAA AAG CAG CCA CTC CTC ATG GAG AAA GAA GGA
Arg His Lys Arg Lys Gln Leu Pro Glu Glu Lys Gln Pro Leu Leu Met Glu Lys Glu Gly
                        490                                 500
1520        1530        1540        1550        1560        1570
TTA CCA CAG CTT GTA TCA GAG CCA TTT ATA AAA GGC TTA GGC AAT AGA GTA GGG CCA AAA
Leu Pro Gln Leu Val Ser Glu Pro Phe Ile Lys Gly Leu Gly Asn Arg Val Gly Pro Lys
                        510                                 520
```

FIG. 6C

```
1580        1590        1600        1610        1620        1630
AGC CCT GAC CTC ACT CTA ACT CAA AGT AAT GTC CAG GTT CCA GAG AAT ATC TGC TGG TAT
Ser Pro Asp Leu Thr Leu Thr Gln Ser Asn Val Gln Val Pro Glu Asn Ile Cys Trp Tyr
             530                                     540

1640        1650        1660        1670        1680        1690
TTT CTG TAA AGA CCA TTT GCA AAA TTG TAA CCT AAT ACA AAG TGT AGC CTT CTT CCA ACT
Phe Izu---

1700        1710        1720        1730        1740        1750
CAG GTA GAA CAC ACC TGT CTT TGT CTT GCT GTT TTC ACT CAG CCC TTT TAA CAT TTT CCC 1760        1770        1780        1790        1800        1810
CTA AGC CCA TAT GTC TAA GGA AAG GAT GCT ATT TGG TAA TGA GGA ACT GTT ATT TGT ATG 1820        1830        1840
TGA ATT AAA AGT GCT CTT AGG AAT TC
```

```
  1  MDLVLKRCLL HLAVIGALLA VGATKVPRNQ DWLGVSRQLR TKAWNRQLYP
 51  EWTEAQRLDC WRGGQVSLKV SNDGPTLIGA NASFSIALNF PGSQKVLPDG
101  QVIWVNNTII NGSQVWGGQP VYPQETDDAC IFPDGGPCPS GSWSQKRSFV
151  YVWKTWGQYW QVLGGPVSGL SIGTGRAMLG THTMEVTVYH RRGSRSYVPL
201  AHSSSAFTIT DQVPFSVSVS QLRALDGGNK HFLRNQPLTF ALQLHDPSGY
251  LAEADLSYTW DFGDSSGTLI SRAPVVTHTY LEPGPVTAQV VLQAAIPLTS
301  CGSSPVPGTT DGHRPTAEAP NTTAGQVPTT EVVGTTPGQA PTAEPSGTTS
351  VQVPTTEVIS TAPVQMPTAE STGMTPEKVP VSEVMGTTLA EMSTPEATGM
401  TPAEVSIVVL SGTTAAQVTT TEWVETTARE LPIPEPEGPD ASSIMSTESI
451  TGSLGPLLDG TATLRLVKRQ VPLDCVLYRY GSFSVTLDIV QGIESAEILQ
501  AVPSGEGDAF ELTVSCQGGL PKEACMEISS PGCQPPAQRL CQPVLPSPAC
551  QLVLHQILKG GSGTYCLNVS LADTNSLAVV STQLIMPVPG ILLTGQEAGL
601  GQVPLIVGIL LVLMAVVLAS LIYRRRLMKQ DFSVPQLPHS SSHWLRLPRI
651  FCSCPIGENS PLLSGQQV
```

FIG. 7b

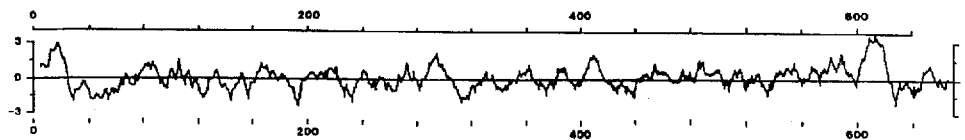

FIG. 7c

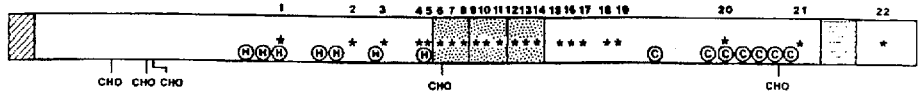

Fig. 11

FIG. 13
A
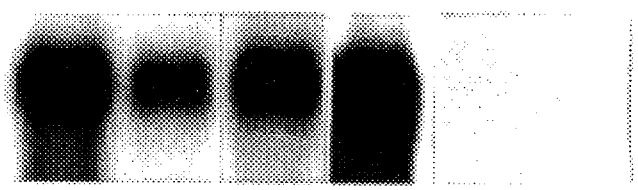
B
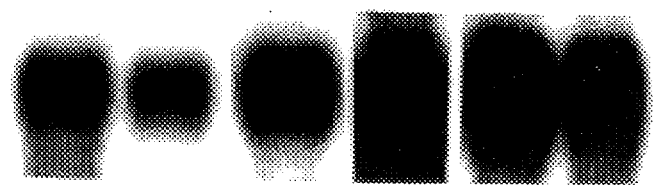

Fig. 14

```
                                          T CCTGCAGACC TTGTGAGGAC TAGAGGAAGA
   -18                                                              -1  +1
   1 ATG CTC CTG GCT GTT TTG TAC TGC CTG CTG TGG AGT TTC CAG ACC TCC GCT GGC CAT TTC
     Met Leu Leu Ala Val Leu Tyr Cys Leu Leu Trp Ser Phe Gln Thr Ser Ala Gly His Phe
                                    10                                      20
  61 CCT AGA GCC TGT GTC TCC TCT AAG AAC CTG ATG GAG AAG GAA TGC TGT CCA CCG TGG AGC
     Pro Arg Ala Cys Val Ser Ser Lys Asn Leu Met Glu Lys Glu Cys Cys Pro Pro Trp Ser
                                    30                                      40
 121 GGG GAC AGG AGT CCC TGT GGC CAG CTT TCA GGC AGA GGT TCC TGT CAG AAT ATC CTT CTG
     Gly Asp Arg Ser Pro Cys Gly Gln Leu Ser Gly Arg Gly Ser Cys Gln Asn Ile Leu Leu
                                    50                                      60
 181 TCC AAT GCA CCA CTT GGG CCT CAA TTT CCC TTC ACA GGG GTG CAT GAC CGG GAG TCG TGG
     Ser Asn Ala Pro Leu Gly Pro Gln Phe Pro Phe Thr Gly Val Asp Asp Arg Glu Ser Trp
                                    70                                      80
 241 CCT TCC GTC TTT TAT AAT AGG ACC TGC CAG TGC TCT GGC AAC TTC ATG GGA TTC AAC TGT
     Pro Ser Val Phe Tyr Asn Arg Thr Cys Gln Cys Ser Gly Asn Phe Met Gly Phe Asn Cys
                                    90                                     100
 301 GGA AAC TGC AAG TTT GGC TTT TGG GGA CCA AAC TGC ACA GAG AGA CGA CTC TTG GTG AGA
     Gly Asn Cys Lys Phe Gly Phe Trp Gly Pro Asn Cys Thr Glu Arg Arg Leu Leu Val Arg
                                    110                                    120
 361 AGA AAC ATC TTC GAT TTG AGT GCC CCA GAG AAG GAC AAA TTT TTT GCC TAC CTC ACT TTA
     Arg Asn Ile Phe Asp Leu Ser Ala Pro Glu Lys Asp Lys Phe Phe Ala Tyr Leu Thr Leu
                                    130                                    140
 421 GCA AAG CAT ACC ATC AGC TCA GAC TAT GTC ATC CCC ATA GGG ACC TAT GGC CAA ATG AAA
     Ala Lys His Thr Ile Ser Ser Asp Tyr Val Ile Pro Ile Gly Thr Tyr Gly Gln Met Lys
                              *     150                                    160
 481 AAT GGA TCA ACA CCC ATG TTT AAC GAC ATC AAT ATT TAT GAC CTC TTT GTC TGG ATG CAT ATA
     Asn Gly Ser Thr Pro Met Phe Asn Asp Ile Asn Ile Tyr Asp Leu Phe Val Trp Met His Ile
                                    170           *                        180
 541 TAT TAT GTG TCA ATG GAT GCA CTG CTT GGG GGA TAT GAA ATC TGG AGA GAC ATT GAT TTT TCT
     Tyr Tyr Val Ser Met Asp Ala Leu Leu Gly Gly Tyr Glu Ile Trp Arg Asp Ile Asp Phe Ser
                                    190                                    200
 601 GCC CAT GAA GCA CCA GCT TTT CTG CCT TGG CAT AGA CTC TTC TTG TTG CGG TGG GAA CAA
     Ala His Glu Ala Pro Ala Phe Leu Pro Trp His Arg Leu Phe Leu Leu Arg Trp Glu Gln
                                    210                                    220
 661 GAA ATC CAG AAG CTG ACA GGA GAT GAA AAC TTC ACT ATT CCA TAT TGG GAC TGG CGG GAT
     Glu Ile Gln Lys Leu Thr Gly Asp Glu Asn Phe Thr Ile Pro Tyr Trp Asp Trp Arg Asp
                                    230                                    240
 721 GCA GAA AAG TGT GAC ATT TGC ACA GAT GAG TAC ATG GGA GGT CAG CAC CCC ACA AAT CCT
     Ala Glu Lys Cys Asp Ile Cys Thr Asp Glu Tyr Met Gly Gly Gln His Pro Thr Asn Pro
                                    250                                    260
 781 AAC TTA CTC AGC CCA GCA TCA TTC TTC TCC TCT TGG CAG ATT GTC TGT AGC CGA TTG GAG
     Asn Leu Leu Ser Pro Ala Ser Phe Phe Ser Ser Trp Gln Ile Val Cys Ser Arg Leu Glu
                                    270                                    280
 841 GAG TAC AAC AGC CAT CAG TCT TTA TGC AAT GGA ACG CCC GAG GGA CCT TTA CGG CGT AAT
     Glu Tyr Asn Ser His Gln Ser Leu Cys Asn Gly Thr Pro Glu Gly Pro Leu Arg Arg Asn
                                    290*                                   300
 901 CCT GGA AAC CAT GAC AAA TCC ACA ACC CCA AGG CTC CCC TCT TCA GCT GAT GTA GAA TTT AGA
     Pro Gly Asn His Asp Lys Ser Arg Thr Pro Arg Leu Pro Ser Ser Ala Asp Val Glu Phe Arg
                                    310                                    320
 961 TGC CTG AGT TTG ACC CAA TAT GAA TCT GGT TCC ATG GAT AAA GCT GCC AAT TTC AGC TTT
     Cys Leu Ser Leu Thr Gln Tyr Glu Ser Gly Ser Met Asp Lys Ala Ala Asn Phe Ser Phe
                                    330                                    340
1021 AGA AAT ACA CTG GAA GGA TTT GCT AGT CCA CTT ACT GGG ATA GCG GAT GCC TCT CAA AGC
     Arg Asn Thr Leu Glu Gly Phe Ala Ser Pro Leu Thr Gly Ile Ala Asp Ala Ser Gln Ser
                                    350                                    360
1081 AGC ATG CAC AAT GCC TTG CAC ATC TAT ATG AAT GGA ACA ATG TCC CAG GTA CAG GGA TCT
     Ser Met His Asn Ala Leu His Ile Tyr Met Asn Gly Thr Met Ser Gln Val Gln Gly Ser
                                    370                                    380
1141 GCC AAC GAT CCT ATC TTC CTT CTT CAC CAT GCA TTT GTT CAG AGT ATT TTT GAG CAG TGG
     Ala Asn Asp Pro Ile Phe Leu Leu His His Ala Phe Val Gln Ser Ile Phe Glu Gln Trp
                       *            390                                    400
1201 CTC CAA AGG CAC CGT CCT CTT CAA GAA CTT TAT CCA GAA GCC AAT GCA CCC ATT GGA CAT CGA
     Leu Arg Arg His Arg Pro Leu Gln Glu Val Tyr Pro Glu Ala Asn Ala Pro Ile Gly His Arg
                                    410                                    420
1261 AAC CGG GAA TCC TAC ATG GTT CCT TTT ATA CCA CTG TAC AGA AAT GGT GAT TTC TTT ATT
     Asn Arg Glu Ser Tyr Met Val Pro Phe Ile Pro Leu Tyr Arg Asn Gly Asp Phe Phe Ile
                                    430                                    440
1321 TCA TCC AAA GAT CTG GGC TAT GAC TAT AGC TAT CTA CAA GAT TCA GAC CCA GAC TCT TTT
     Ser Ser Lys Asp Leu Gly Tyr Asp Tyr Ser Tyr Leu Gln Asp Ser Asp Pro Asp Ser Phe
                                    450                                    460
1381 CAA GAC TAC ATT AAG TCC TAT TTG GAA CAA GCG AGT CGG ATC TGG TCA TGG CTC CTT GGG
     Gln Asp Tyr Ile Lys Ser Tyr Leu Glu Gln Ala Ser Arg Ile Trp Ser Trp Leu Leu Gly
                                    470           *                        480
1441 GCG GCG ATC GTA GGG GCC GTC CTC ACT GCC CTG CTG GCA GGG CCT GTG AGC TTG CTG TGT CTT
     Ala Ala Met Val Gly Ala Val Leu Thr Ala Leu Leu Ala Gly Pro Val Ser Leu Leu Cys Leu
                       ➔TGC CCT GCT GGC AGG GCC TGT GAG CTT GCT GTG
                        Cys Pro Ala Gly Arg Ala Cys Glu Leu Ala Val
                                    490                                    500
1501 CGT CAC AAG AGA AAG CAG CTT CCT GAA GAA AAG CAG CCA CTC CTC ATG GAG AAA GAG GAT
     Arg His Lys Arg Lys Gln Leu Pro Glu Glu Lys Gln Pro Leu Leu Met Glu Lys Glu Asp
     TCG TCA CAA GAG AAA GCA GCT TCC TGA
     Ser Ser Gln Glu Lys Ala Ala Ser ---
                                    510                                    520
1561 TAC CAC AGC TTG TAT CAG AGC CAT TTA TAA AAAGGCTTAGGCAATAGGAGTAGGGCCAAAAAGCCTGACCT
     Tyr His Ser Leu Tyr Gln Ser His Leu ---

1631 CACTCTAACTCAAAGTAATGTCCAGGTTCCCAGAGAATATCTGCTGGTATTTTCTGTAAAGACCATTTGCAAAATTGTAA
1712 CCTAATACAAAGTGTAGCCTTCTTCCAACTCAGGTAGAACACACCTGTCTTTGTCTTGCTGTTTTCACTCAGCCCTTTTA
1792 ACATTTTCCCCTAAGCCCATATGTCTAAGGAAAGGATGCTATTTGGTAATGAGGAACTGTTATTTGTATGTGAATTAAAA
1873 GTGCTCTTATTTTAAAAAA
```

```
-2228 TAGACTGTTGAGTACAACACGTGTAGGCCAGAGAGACAGTGGCCTATAC
-2178 TTGGGACAAATAATAAAGAGGTCTGTCCTATTTAAGAAAATCAACCTGTAAA
-2128 GGAAATTAATAGGACTAAGTACATTTTAGTAAGGCCTCTAAGCAGCTCT
-2078 AAAGATTATGAAAAATACACGGACAGCAGACACAAAAGCCCTTAAAGAG
-2028 CATGAAGACTTTCTAAGTTATTTCACTGGAAGCCTGATAGTGGGCAAGT
-1978 GTAAGGCAAAATTCTTAATTAAATTGAAAATGATAAGTTGAATTCTGTCT
-1928 TCGAGAACATAGAAAAAGAATTATGAAATCCAACATGTGGTTACAAGTAA
                              URE
-1878 TGCAGACCCAAGGCTCCCCAGGGACAAGAAGTCTTGTGTTAACTCTTTGT
           AP-2  AP-2
-1828 GGCTCTGAAAGAAAGAGAGAAAGATTAAGCGTCCTGTGGAGATC
-1778 ATGTGATGACTTCCTGATTCCAGCCAGGAGCCATTTCATTGAAACTT
                                    Oct-1
-1728 CTCTTCCTCTTCACCCACACACTGCTCACCTACCTGAAAGCCTGTTCT
                                            GRE
-1678 GTCTCAAAAAAGTTGTTGGATGAGCCGTGACTTTTTTTTTTTCTTAAATA
-1628 ATGAGACAAACTCCAGAAAAAGAGAAAAAGCAGAAGCACTCTGACATTCC
-1578 CGCATCATCGAAATAGTGATGGCTTTTCTAGAATGCTTCAGCTAAGGAC
-1528 CCAAAATAATACTCTTTTGTCACTCTTCAAAGCTTCAGAGGGCAACTTTGATTTG
-1478 ACTACTCTTTTGTCACTCTTCAGCTCAAAAAGAGCTCACTTTAGTTCA
-1428 AACACAAAAGCTTAAGCCCTCCAGTTGGTCCAGGTTTAATTTTCT
                                         GRE
-1378 ATGAGTGGAGGCCTCAGTTAATGCTCAACTTGATAGATGAAACAC
-1328 AGTCCCTCCTCTACACATTTCCCTGACTCAGGAGTTTGTATATATTCT
                              AP-1
-1278 CAGTTGTCTGTCCAACTTATGCCACTCTTTGAGATATTAATCAAGGAC
-1228 TCCCTTGATAACACTTGCATATTATTCAAAATTATGCAATTCTTCTA
        URE, Oct-1
-1178 ATATCAGCCCACAAATACATTCTCTTCCATTAAAAGTTGACTAATTATCT
                                         AP-1
-1128 ATACTACTCATTTGAAAACTAACATAGTTAAGTTGTATTTTTAGCCATGA
-1078 ATTTCAGTTTCCCTAGCTCACTACTATACACAGAGAAGGAAACTTTTGAAATA
-1028 ATTGAGATGATCAAAAATATTTGCTGAAGTAAATATATTTCTCTTTTCA
-978  TTCACTCACTAATTGAGAATGTCTTTGCACAAAACACATTGCAAAAACAT
      AP-1
-928  TTTCAAAAAAATTCCTAATTTCTAGAATTGATAGGAAAACACATATGGCT
-878  ACAGCATTGGAGAGAGAGAGAAAGGAAGAGAGAGAGAGGAGAGAGAGAA
-828  AGGAGAGGAGAGAGACACAGAGGAGAGAGAGAGAGGATAGAGGGGAGAG
-778  AGAGAGAAGAGACACAGAGGAGAGAGAGAGAGGAGAGGATAGAGGGAGAGAG
-728  AGGGAGAGGGAGAGAGAAAGAGAGAGAGGAGAGAGAGAGAGAGAGAGGG
-678  AGAGAGAGAGAGAAAGAGAGAGAGAGAGGAGAGAGAGAGAGAGAGCTCTT
-628  AACGTGAGATATCCACAATGAACAATCTGCCCAGTTATCAAAGTGCAG
-578  CTATCCTTAGGAGTTGTCAGAAAATGCATCAGGATTATCAGAGAAAGTA
-528  TCAGAAAGATTTTTTTTCTGATACGTTGTCTGGGCTCTGAAGACAATCTCTC
-478  TTCAATAACATATAAGAATTCTGTCTGAAACATTGTAGCCTCTTTATGGTCTCTGAGAAA
-428  TGCATATTGAGTTCTTCAAACATTGTAGCCTCTTTATGGTCTCTGAGAAA
-378  TAACTACCTTAAACCCATAATCTTAATACTTCCTAAACTTTCTTAATAA
-328  GAGAAGCTCTATTCCTGACACTACTCTCATTTGAAGGTCAAATCATCA
                                    Oct-1
-278  TTAGTTTTGTAGTCTATTAACTGGGTTGCTTAGGTCAGGCATTATTATT
-228  ACTAACCTTATTGTTAATATTGTAATCTAACCATAAGAATTAAACTATTAATGGT
-178  GAATAGAGTTTTTCACTTTAACATAGGCCTATCCCACTGGTGGGATACGA
-128  GCCAATTCGAAAGAAAAAGTCAGTCATGTGCTTTTCAGAGGATGAAAGCT
      CAT-box                    AP-1
-78   TAAGATAAAGACTAAAGTGTTTGATGCTGGAGGTGGGAGTGGTATTATA
                                                TATA
-28   TAGGTCTCAGCCAAGACAGATGTGATAATCACTGTAGTAGCTGGAAGA
      -box
      GAAATCTGTGACTCCATTAGCCAGTTCCTGCGAGACCTTGTGAGGACTAG
      AGGAAGAATTGCTCCTGGCTGTTTTGTACTGCCTGCTGTGGAGTTTCCAGA
      CCTCCGCTGGCCATTTCCCTAGAGCCTGTGTCTCCTCTCTAAGAACCTGAT
```

Fig. 26

CDNA CLONES FOR A REGULATORY PROTEIN IN THE MELANIN-PRODUCTION PATHWAY

This is a continuation-in-part of application Ser. No. 07/362,847, filed Jun. 7, 1989, now abandoned, which is a division of application Ser. No. 06/915,753, filed Oct. 6, 1986 now U.S. Pat. No. 4,898,814 granted Feb. 6, 1990.

This invention was made with governmental support under the National Institutes of Health grant RO1 AR40248. The government has certain rights in the invention.

FIELD OF THE INVENTION

The present invention relates to cDNA clones for human tyrosinase and for a regulatory protein in the melanin-production pathway. More specifically, it relates to the cDNA clones and methods of using of the cDNA clones.

BACKGROUND OF THE INVENTION

Human tyrosinase is an essential enzyme which regulates the production of melanin, a group of brown of black pigments in the skin and eyes of humans. The lack of a human tyrosinase gene in usable form greatly limited medical research in the field of albinism, and other medical and nonmedical applications relating to the control of pigment production in human melanocyte cells. This invention relates to the discovery of the cDNA gene which expresses human tyrosinase and the applications of this discovery. When the cDNA is fused to an expression vector, the cDNA is useful to produce pure tyrosinase. When used as a cDNA probe the DNA is useful in the production or the control of production of human melanin. As a cDNA probe the cDNA gene is useful for genetic analysis of human albinism and melanotic and amelanotic melanoma, and also prenatal diagnosis of albinism.

There was a minimum of research on the genetic control of melanin formation because of the lack of availability of suitable nucleic acid probe (gene sequence). cDNA for human tyrosinase is a key material for the study. The material has been used to further our understanding of why some melanoma cells lose the expression of tyrosinase gene and become more invasive. Differences in tyrosinase expression in cancer cells make it possible that the gene probe can be used in understanding and as a marker for malignancy. Understanding of the regulation of melanin biosynthesis will lead to the development of a rational chemotherapy of human melanoma because the intermediate substances of melanin are known to be toxic to pigment cells. Deletion of genes around albino locus (tyrosinase structural gene) becomes lethal in mice. The cDNA probe has and will continue to open up new research areas to identify genes causing lethal effect in mouse embryo.

A major obstacle in understanding the biology of pigmentation and pigment-related diseases is the lack of molecular probes specific for molecules involved in melanin biosynthesis. Tyrosinase catalyzes the first two steps of melanin biosynthesis and, therefore, is a key enzyme. Tyrosinase-negative oculocutaneous albinism is due to inactivating mutations of the tyrosinase gene (Tomita, Y., Takeda, A., Okinaga, S., Tagami, H. & Shibahara, S. (1989) Biochem. Biophys. Res. Commun. 164, 990–996); Chintamaneni, C. S., Halaban, R., Kobayashi, Y., Witkop, C. J. & Kwon, B. S. (1991) Proc. Anti. Aca. Sci. USA (in press) each incorporated herein by reference). Other albino mutants may, however, be positive for tyrosinase activity, which indicates that a block in melanin synthesis is not necessarily due to the absence of tyrosinase. Elucidation of the influence of additional factors in the control of melanization could be significant for the understanding of tyrosinase-positive albinism and variations in skin and hair pigmentation.

When a λgt11 cDNA library of a primary culture of pigmented human melanocytes was screened with anti-tyrosinase antibodies, sixteen cDNA clones whose gene products reacted to anti-tyrosinase antibodies were isolated. Thirteen clones which cross-hybridized to each other were mapped to the mouse albino locus (c) and characterized as the cDNA encoding human tyrosinase. The three remaining clones also cross-hybridized but did not share homology with the other group of clones. The representative cDNA clone was referred to as Pmel 17-1/Pmel 14. The gene for Pmel 17-1 did not map to the c-locus on mouse Chromosome 7 and that the transcripts of Pmel 17-1 could be detected by Northern blotting in melanocytes but not in various non-pigmented cells including hepatoma, leukemia, fibroblast, and neuroblastoma cells or in non-pigmented organs such as the liver, spleen, and kidney of mouse and man.

Pmel 17-1 gene expression is inducible in human and mouse melanoma cells by β-melanotropin or isobutylmethyl xanthine; this inducibility is similar to that of tyrosinase. Therefore, the Pmel 17-1 protein may be a positive regulator of melanin biosynthesis. This protein is probably important because the gene showed a high degree of evolutionary conservation. Pmel 17-1 mRNA and the melanin content in melanocytes were found to be proportionally identical. In addition, since Pmel 17-1 expression correlates more closely with the level of melanin than does the expression of tyrosinase, the Pmel 17-1 protein may regulate the melanin pathway at steps in the eumelanin synthesis pathway distal to dopaquinone.

Mouse molecular genetic linkage maps have proved invaluable for the structural and functional characterization of the mouse genome. They have been utilized to determine whether newly identified genes are homologous to known genes or classic mutations (Justice, M. J., Siracusa, L. D., Gilbert, P. J., Heisterkamp, N., Groffen, J., Chada, K., Satan, C. M., Copeland, N. G. & Jenkins, N. A. (1990) Genetics 125, 855–866; Chabot, B., Stephenson, D. A., Chapman, V. M., Besmer, P. & Bernstein, A. (1988) Nature 335, 88–89; Geissler, E. A., Ryan, M. A. & Housman, D. E. (1988) Cell 55, 185–192; Bailing, R., Deutsch, U. & Gruss, P. (1988) Cell 55, 531–535; Danciger, M., Bowes, C., Kozak, C. A., LaVail, M. M., Farber, D. B. (1990) Invest. Ophthalmol. Vis. Sci. 31, 1427–1432; each incorporated herein by reference). By analyzing interspecies crosses, the mouse homologue of Pmel 17 gene was mapped to Chromosome 10 near si (silver), a mouse coat color locus.

This information was reported in a paper entitled "A melanocyte-specific gene, Pmel17, maps near the silver coat color locus on mouse chromosome 10 and is in a syntenic region on human chromosome 12", by Byoung S. Kwon, Chaya D. Chintamaneni, Christine A. Kozak, Neat G. Copeland, Debra J. Gilbert, Nancy Jenkins, David Barton, Uta Francke, Yvonne Kobayashi, & Kack K. Kim, Proc. Natl. Acad. Sci., Vol. 88 pp. 9228–9232, October 1991, and this paper is incorporated herein by reference.

Oculocutaneous albinism (OCA) is a syndrome that encompasses a group of individual inborn errors, each inherited as a Mendelian autosomal recessive trait and characterized by the absence or near absence of melanin pigmentation in the skin, hair, and eyes. To date, depending upon the classification method, there are 8 or 11 recognized forms of OCA (King, R. A. (1987) in Neurocutaneous Diseases, ed. Gomez, M. R. (Butterworth, Boston), pp. 311–325, incorporated herein by reference). No melanin is produced in the absence of tyrosinase, a copper-containing glycoprotein (Lerner, A. B., Fitzpatrick, T. B., Calkins, E. & Summerson, W. H. (1949) J. Biol. Chem. 178, 185–195, incorporated herein by reference.). Tyrosinase (monophenol, 3,4-dihydroxyphenylalanine:oxygen oxidoreductase, EC 1.14.18.1) catalyzes three reactions in the melanin biosynthetic pathway: hydroxylation of L-tyrosine to 3,4-dihydroxy-L-phenylalanine (dopa), oxidation of dopa to dopaquinone, and oxidation of 5,6-dihydroxyindole to indole-5,6-quinone (Pomerantz, S. H. (1966) J. Biol. Chem. 241, 161–168; Shimao, K. (1962) Biochim. Biophys. Acta 62, 205–215; Korner, A. & Pawelek, J. M. (1982) Science 217, 1163–1165; each incorporated herein by reference.). OCA is a serious disorder since the deficiency of melanin produces visual difficulties such as nystagmus, strabismus, photophobia, and astigmatism. The cutaneous photosensitivity results in a predisposition of the skin to cancer (Witkop, C. J., Jr., Quevedo, W. C., Jr., Fitzpatrick, T. B. & King, R. A. (1989) in "The Metabolic Basis of Inherited Disease," eds. Scriver, C. R., Bcaudet, A. L., Sly, W. S. & Valle, D. (McGraw-Hill, New York), Vol. 2, pp. 2905–2947, incorporated herein by reference.). The most severe form of OCA is tyrosinase-negative albinism, in which, by definition, tyrosinase activity is not detected in the hair bulbs (Witkop, C. J., Jr. (1971) in Advances in Human Genetics. eds. Hariss, H. & Hirschhoen. J. (Plenum. New York). Vol. 2, pp. 61–142, incorporated herein by reference.). The incidence of this form of OCA in the United States is estimated at 1:39,000 in the Caucasian population and 1:28,000 in the Black population.

The human tyrosinase cDNA, disclosed herein and in Kwon B. S., Haq, A. K., Pomerantz, S. H. & Halaban, R. (1987) Proc. Natl. Acad. Sci. USA 84, 7473–7477, incorporated herein by reference, was used to show that the tyrosinase gene is present as a single copper haploid genome at the TYR locus on human chromosome 11 (Barton, D. E., Kwon, B. S. & Francke, U. (1988) Genomics 3, 17–24, incorporated herein by reference.) and at the c locus on mouse chromosome 7. The availability of tyrosinase cDNA enabled the identification of mutations in human and murine tyrosinase-negative albinos (Kwon, B. S., Wakulchik, M., Haq, A. K., Halaban, R. & Kestler, D. (1988) Biochem. Biophys. Res. Commun. 153, 1301–1309; Kwon, B. S., Halaban, R. & Chintamaneni, C. (1989) Biochcm. Biophys. Res. Commun. 161, 252–260; Tomita, Y., Takeda, A. Okinaga, S., Tagami, H. & Shibahara. S. (1989) Biochcm. Biophys. Res. Commun. 164, 990–996; Giebel, L. B., Strunk, K. M., King, R. A., Hanifin, J. M. & Spritz, R. A. (1990) Proc. Natl. Acad. Sci. USA 87, 3255–3258; Spritz, R. A., Strunk, K. M., Giebel, L. B. & King, R. A. (1990) N. Engl. J. Med. 322, 1724–1728; each incorporated herein by reference.). As part of the present disclosure, a mutation is shown in the tyrosinase gene of a tyrosinase-negative albino patient that resulted in an inactive enzyme with an altered carboxyl terminus. This information was reported in a paper entitled "A single base insertion in the putative transmembrane domain of the tyrosinase gene as a cause for tyrosinase-negative oculocutaneous albinism", by Chaya D. Chintamaneni, Ruth Halaban, Yvonne Kobayashi, Carl J. Witkop, Jr., and Byoung S. Kwon, Proc. Natl. Acad. Sci., Vol. 88 pp. 5272–5276, June 1991) and this paper is incorporated herein by reference.

The cis-acting elements controlling transcription of eukaryotic genes typically include the core promoter elements that determine the basal level of transcription and several enhancer elements that mediate the action of trans-acting regulatory factors involved in determining the overall rate of transcription. Tyrosinase (monophenol monoxygenase, monophenol, L-dopa: oxygen oxidoreductase, E.C. 1.14.18.1) is specifically expressed in the melanocytes and is an essential enzyme in melanogenesis (Hearing, V. J., and M. Jimenez (1989) Analysis of mammalian pigmentation at the molecular level. Pigment. Cell. Res., 2:75–85 incorporated herein by reference).

The isolation of cDNA for mouse tyrosinase gene has been reported (Yamamoto, H., Takenchi, S., Kudo, T., Sato, C., and T. Takeuchi (1989). Melanin production in cultured albino melanocytes transfected with mouse tyrosinase cDNA. Jpn. J. Genet., 64:121–135 incorporated herein by reference; Kwon et al., 1988; Muller, G., Ruppert, S., Schmid, E., and G. Schutz (1988) Functional analysis of alternatively spliced tyrosinase gene transcripts. EMBO J., 7:2723–2730 incorporated herein by reference). The mouse tyrosinase gene was characterized (Ruppert et al., 1988) and showed that the gene encoding tyrosinase is situated at the genetically well characterized c-locus in mouse (Kwon et at., 1988; Kwon, B. S., Haq, A. K., Wakulchik, M. S., Kestler, D., Barton, D. E., Francke, U., Lamoreux, M. L., Whitney, J. B., and R. Halaban (1989) Isolation, chromosomal mapping and expression of the mouse tyrosinase gene. J. Invest. Dermatol., 93:589–594 incorporated herein by reference). This was also demonstrated by the rescue of c-locus mutant albino through the introduction of functional tyrosinase minigene constructs into mice (Yamamoto et al.,1989; Beermann, F., Ruppert, S., Hummler, E., Bosch, F. X., Muller, G., Ruther, U., and G. Schutz (1990) Rescue of albino phenotype by introduction of a functional tyrosinase gene into mice. EMBO J., 9:2819–2826 incorporated herein by reference). Studies also indicated that a 2.1 kb of 5' upstream regulatory region of tyrosinase gene appears sufficient to provide appropriate developmental regulation and tissue-specific expression of tyrosinase gene (Yokoyama, T., Silversides, D. W., Waymire, K. G., Kwon, B. S., Takeuchi, T., and P. Overbeek (1990) Conserved cysteine to serine mutation in tyrosinase is responsible for the classical albino mutation in laboratory mice. Nucleic. Acids. Res., 18:7293–7298 incorporated herein by reference. More recently, it has been reported that a 270 base pair region upstream of the transcriptional start site of the mouse tyrosinase gene was sufficient to induce tissue-specific expression of the tyrosinase gene in transgenic mice (Kluppel, M., Beermann, F., Ruppert, S., Schmid, E., Hummler, E., and G. Schutz (1991) The mouse tyrosinase promoter is sufficient for expression in melanocytes and in the pigmented epithelium of the retina. Proc. Natl. Acad. Sci. USA., 88:3777–3781 incorporated herein by reference). These observations indicate that essential and tissue specific cis-acting element(s) regulating the expression of the mouse tyrosinase gene should lie within a short segment adjacent to the transcription start site.

Investigation has been done for a potential cis-acting element and trans-acting factor regulating mouse tyrosinase gene expression using DNA binding studies, affinity purification and transient expression system, and is disclosed herein.

Tyrosinase (monophenol monooxygenase; monophenol, L-dopa: oxygen oxidoreductase, E.C. 1.14.18.1) is the core enzyme in melanogenesis and is expressed in tissue-specific manner among the pigmented cells (Mason, 1948; Hearing and Jimenez, 1989). Inactivating mutations of the tyrosinase gene cause tyrosinase-negative oculocutaneous albinism in humans (Tomita et at., 1989; Spritz et al., 1990; Chintamaneni et at., 1991). The human tyrosinase cDNA (Kwon et al., 1987) mapped to the q arm of chromosome 11 (Barton et at., 1988). The human and mouse tyrosinase cDNA sequences were reported (Kwon et al., 1988; Shibahara et al., 1988; Muller et al., 1988, Bouchard et at., 1989). The gene encoding tyrosinase in humans comprises five exons and a partial characterization of this gene has also been reported (Giebel, L. B., Strunk, K. M and Spritz, R. A. (1991). Organization and nucleotide sequence of the human tyrosinase gene and a truncated tyrosinase-related segment. Genomics. 9, 435–445., incorporated herein by reference.

Earlier observations in the mouse indicated that the gene for tyrosinase is encoded by the genetically well characterized c locus (Kwon et al., 1987; Kwon et al., 1989). This has been demonstrated by the rescue of the c locus mutant-albino through introduction of functional tyrosinase minigene constructs into mice (Yamomoto et al., 1989, Beerman et al., 1990). A 2.1 Kb of the 5' flanking sequence was sufficient to provide appropriate developmental regulation of tyrosinase gene expression including induction of pigmentation in the retinal pigment epithelial cells (Yokoyama et al., 1990). Kluppel et al., (1991) have also indicated that melanocyte specific expression of tyrosinase gene in mouse could be obtained with as little as 270 base pairs (bp) of 5' flanking sequence thereby suggesting that cis-acting elements determining the expression of mouse tyrosinase gene should lie within the small promoter region. On the contrary, in humans, this important information of transcriptional control region is yet to be identified. Analysis of promoter function becomes essential to identify cis-acting elements and trans-acting factors that direct tissue-specific and developmentally-controlled expression of human tyrosinase gene. These analyses are also important for the understanding of the regulation of human pigmentation and certain forms of pigmentation disorders such as human hypopigmentation and albinism.

A partial restriction map of a 40 Kb region of human tyrosinase gene which contains the promoter region was determined, the sequence of 2.2 Kb promoter was determined, the transcription start site was identified and the promoter function in transient expression system was characterized, and are disclosed herein.

SUMMARY OF THE PRESENT INVENTION

The present invention started when a λgt11 cDNA library of normal human melanocytes was screened with antibodies directed against purified hamster tyrosinase. Sixteen independent clones which gave a positive signal were isolated from 5×10$^5$ independent plaques. cDNA inserts of 13 clones among the 16 candidates cross-hybridized with each other, indicating that they were from related mRNA species. mRNA homologous to a representative cDNA λmel 34 was expressed specifically in melanocytes, detecting an approximately 2.4 kb mRNA species of human melanocytes. The nucleotide sequence of the three overlapping cDNA inserts spanning 1.88 kb was determined and an amino acid sequence was deduced. The human tyrosinase is composed of 548 amino acids with a molecular weight of 62,160 excluding a hydrophobic signal peptide. Mouse genomic DNA blot analysis revealed that the gene for λmel 34 was deleted in albino mouse homozygous for the deletion at and around the albino locus on chromosome 7. It is concluded that λmel 34 contained cDNA encoding human tyrosinase. Moreover, the cDNA gene for human tyrosinase was recovered from the λmel 34 and can be used for many purposes including the production of pure human tyrosinase.

The three clones of the 11 not represented by λmel 34 are represented by λmel 17-1. The gene for λmel 17-1 cDNA was not mapped at the albino locus, detected signal hybridizing restriction fragment in human and mouse DNA, and was highly conserved from mouse to human. The abundance of λmel 17-1 cRNA paralleled the melanin content in human and mouse melanocytes. The expression of λmel 17-1 cRNA was elevated after stimulation of mouse and human melanoma cells with MSH or/and IBMX, and U-V light (such as suntan). This was also closely correlated with the elevation of melanin content. The fact that the λmel 17-1 is gene conserved evolutionarily indicates that the molecule encoded by the λmel 17-1 has biologically important functions. The expression of that gene is controlled by hormones (MSH) or U-V light and positively correlated with the melanin content. These data indicate that the gene is involved in melanin biosynthesis in addition to tyrosinase. Current studies suggest that λmel 17-1 gene product act on melanin biosynthesis's pathway distal to tyrosinase.

Melanocytes preferentially express an mRNA species, Pmel 17, whose protein product cross reacted with anti-tyrosinase antibodies and whose expression correlated with the melanin content. The deduced protein structure has been analyzed and its chromosomal location in mouse and man has been mapped. The amino acid sequence deduced from the nucleotide sequence of the Pmel 17 cDNA showed that the protein is composed of 645 amino acids with a molecular weight of 68,600. The Pmel 17 protein contains a putative leader sequence and a potential membrane anchor segment which indicates that this may be a membrane-associated protein in melanocytes. The deduced protein contains five potential N-glycosylation sites and relatively high levels of serine and threonine. Three repeats of a 26 amino acid motif appear in the middle of the molecule. The human Pmel 17 gene, designated D12S53E, maps to Chromosome 12, region 12pter-q21; and the mouse homologue, designated D12S53Eh, maps to the distal region of mouse Chromosome 10, a region also known to carry the coat color locus si (silver).

A molecular defect is the likely basis for inactivity of the tyrosinase (EC 1.14.18.1) for a patient with tyrosinase-negative oculocutaneous albinism. A single base (thymine) was inserted in exon 5 of the tyrosinase gene following codon 471 in the putative transmembrane coding region. This insertion caused a shift in the reading frame of 19 amino acids at the 3' end and introduced a premature termination signal that would be expected to truncate the protein by 21 amino acids at the carboxyl terminus. The albino tyrosinase was not recognized by antibodies directed to the carboxyl terminus of tyrosinase. Furthermore, as shown by gel electrophoresis of the immunoprecipitated protein, the tyrosinase was ~3 kDa smaller than normal. Similar immunoprecipitation data were obtained when cloned normal and mutant tyrosinases were expressed in COS-1 cells.

Tyrosinase gene is specifically expressed in melanocytes. The understanding of the molecular basis of tissue specific expression of the tyrosinase gene will greatly explain the mechanism of pigmentation. A nucleotide sequence, SEQ ID NO:1 TGATGTATTC, located −236 base pairs upstream of the transcription start site, enhances tyrosinase gene expression in mouse melanoma cells. The sequence is referred to as tyrosinase element-1 (TE-1). TE-1 was protected from DNase I cleavage by pigment cell nuclear extract but was not protected by non-pigment cell nuclear extract. Partial purification of TE-1 binding protein (TEBP-1) was performed from the B16 mouse melanoma cell nuclear extract using biotin-cellulose affinity chromatography. The affinity purified fraction exhibited binding to DNA fragment containing TE-1 and to synthetic oligomer representing TE-1. UV-cross-linking indicated that the size of TEBP-1 is approximately 49 kD. TE-1 also directed enhanced CAT activity in the B16 melanoma cells but not in non-pigment cells. These data indicate that TE-1 may be an enhancer element which is responsible for pigment cell specific expression of the tyrosinase gene.

Tyrosinase is the principal enzyme in the biosynthesis of melanin. The expression of tyrosinase is tissue specific and appears to be regulated by various hormonal and environmental factors. The elucidation of molecular basis of the control of tyrosinase gene expression will enhance greatly our understanding of the regulation of human pigmentation. A recombinant cosmid clone containing the promoter region of human tyrosinase gene was mapped, sequenced and characterized. The potential regions regulating tyrosinase gene expression were also determined. The cosmid clone (Cos 28A) with a ~40 Kb insert of human tyrosinase gene contains a 7 Kb 5' flanking region, the first exon, first intron, the second exon and a 10 Kb region of the second intron. The sequence analysis of the promoter region revealed the presence of transcription initiator elements TATA and CAAT sequences. In addition, other potential enhancer elements such as AP-1, AP-2, glucocorticoid responsive element (GRE), Oct-1 and UV-responsive element (URE) were also found. A series of plasmids (pHTY-CAT) that contain 5' sequential deletions of human tyrosinase 5' flanking sequence were constructed and fused to the reporter gene, chloramphenicol acetyltransferase (CAT). The plasmids were used to locate promoter regions that potentially regulate tyrosinase gene expression in transient expression system with melanoma cell lines. The plasmid construct with −2020 bp promoter directed highest CAT activity. When the deletion reached −1739 bp, the CAT activity was dramatically reduced indicating the presence of enhancer elements between −2020 and −1739 bp. Further deletions up to −550 bp resulted in constant decrease of CAT activity indicating the existence of silencer elements between −1730 and −550 bases of the promoter. −550 bp of the 5' flanking sequence directed approximately 91% CAT activity of that by the −2020 bp promoter region. Further deletions beyond −550 bp reduced CAT activity. Based on the data, human tyrosinase gene expression is governed by multiple regulatory elements.

It is a primary object of the present invention to provide a new and improved cDNA gene which expresses human tyrosinase.

It is another object of the present invention to identify a new and improved cDNA gene which expresses human tyrosinase by its nucleotide sequence.

It is still another object of the present invention to teach that the cDNA from bacteriophage λmel 34 may be used as a probe for the production or control of production of human melanin.

It is another object of the present invention to teach that the cDNA gene contained in the λmel 34 is useful as a probe for genetic analysis of human albinism and melanotic and amelanotic melanoma, and also for prenatal diagnostics for albinism.

It is another object of the present invention to teach that the cDNA gene contained in λmel 17-1 is useful as a probe for detecting the change in the degree of melanization of normal human melanocytes and melanoma cells.

It is still another object of the present invention to teach an isolated protein, Pmel 17.

It is still another object of the present invention to teach a DNA sequence coding for the protein Pmel 17 and fragments and derivatives thereof, said fragments and derivatives which: 1) can be used as a probe for similar coding sequences, 2) can be used as a probed for genetic analysis of human albinism, or 3) can be used the diagnostics of prenatel albinism.

It is still another object of the present invention to teach an isolated protein, TEBP-1, obtainable by probing with a 27 base pair double stranded oligomer having two 27 base pair complementary oligomers with sequences:

a) SEQ ID NO:2 5' AGCTTGATGTATTCTTGATAC-TACTTA 3', and b) SEQ ID NO:3 5' AGCTTAAGTAGTATCAAGAATA-CATCA 3'.

Figure 5:
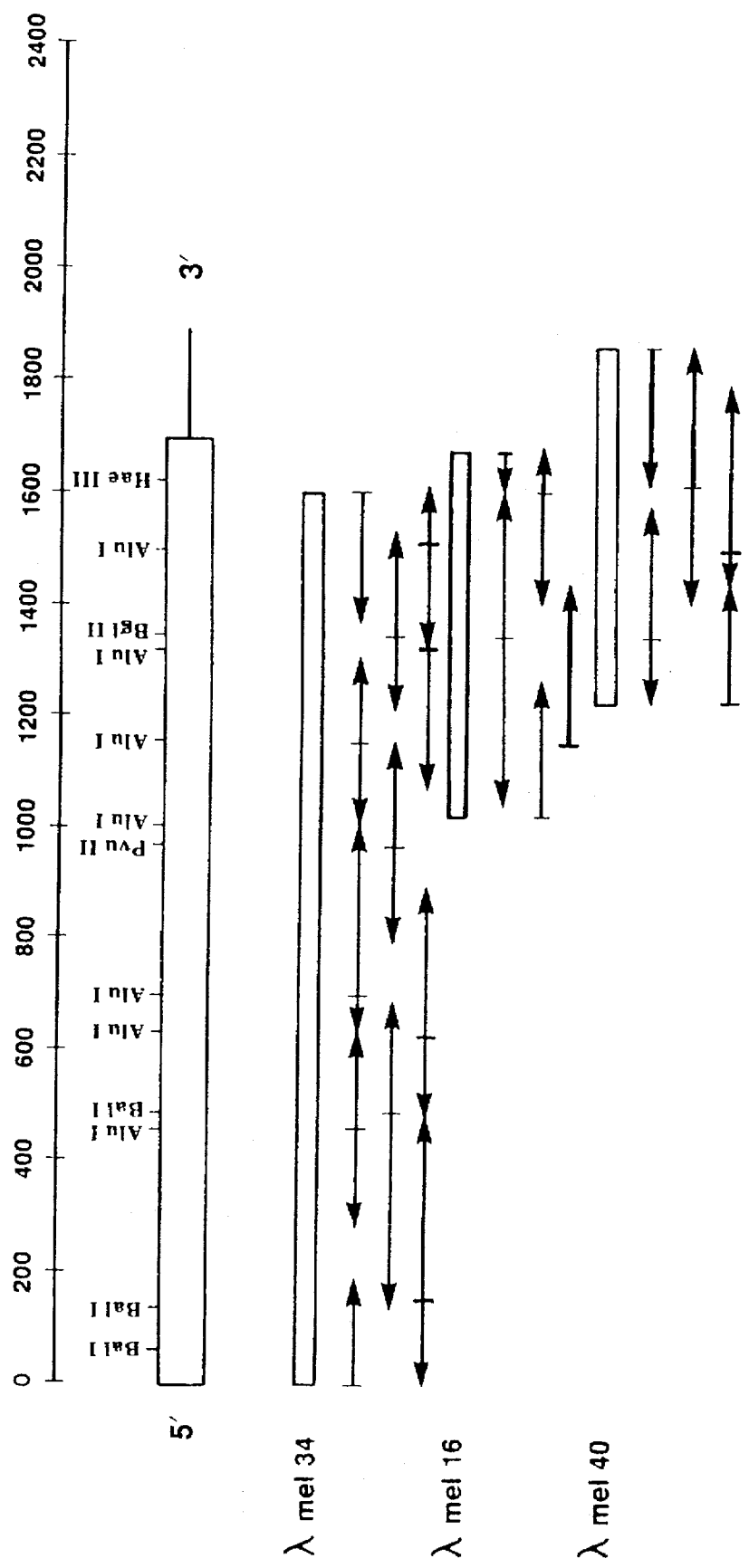

FIG. 5 shows a partial restriction map and sequencing strategy for human tyrosinase cDNA.

FIGS. 6A, 6B, 6C and 6D together are a table showing the nucleotide sequence of cDNA encoding human tyrosinase and its deduced amino acid sequence shown in SEQ ID NO:4 and SEQ ID NO:5 respectively.

FIG. 7 shows an amino acid sequence analysis of the potential Pmel 17 protein: A. The deduced amino acid sequence of Pmel 17 shown in SEQ ID NO:6. The signal region is heavily underlined. The potential glycosylation sites are underlined in regular print. The putative transmembrane region is doubly underlined. Three repeat motifs of 26 amino acids are indicated by overline with bars. Each bar indicates the start amino acid of the repeat.; B. Hydropathicity profile of the deduced amino acid sequence of Pmel 17. Local hydropathicity values calculated by the method of Kyte and Doolittle were plotted versus amino acid residues. Positive values indicate hydrophobic regions, and negative values indicate hydrophilic regions.; C. Schematic representation of the potential Pmel 17 protein. The entire coding region is boxed. The potential signal peptide is hatched. The transmembrane segment is indicated by parallel lines. The central repeat motifs are stippled. Positions of histidines (H), cysteines (C), and possible N-linked glycosylation sites (CHO) are indicated. The numbers (1–22) on the box indicate the positions of asterisks (*) which indicate the positions of Ser/Thr-Ser/Thr sequences.

Figure 8:
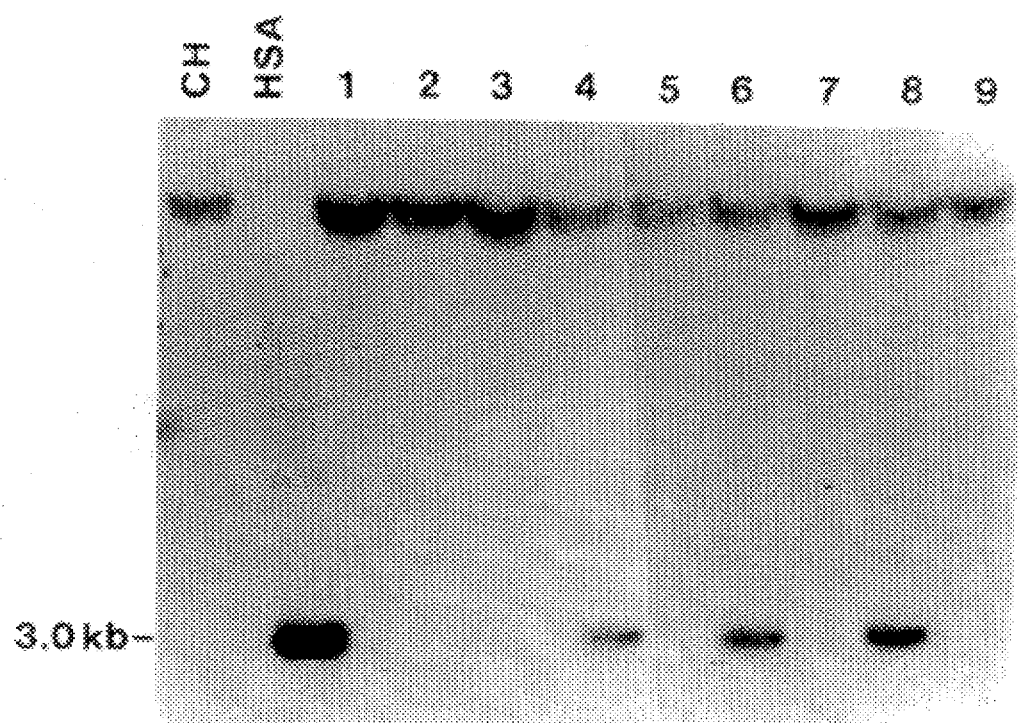

FIG. 8 shows a southern Blot of Hind III digested DNA of human (HSA) and Chinese hamster (CH) origin and from CH×HSA hybrid cell lines (lanes 1–9). Only the hybrids in lanes 4,6, and 8 are positive for the human-specific 3 Kb fragment.

Figure 9:
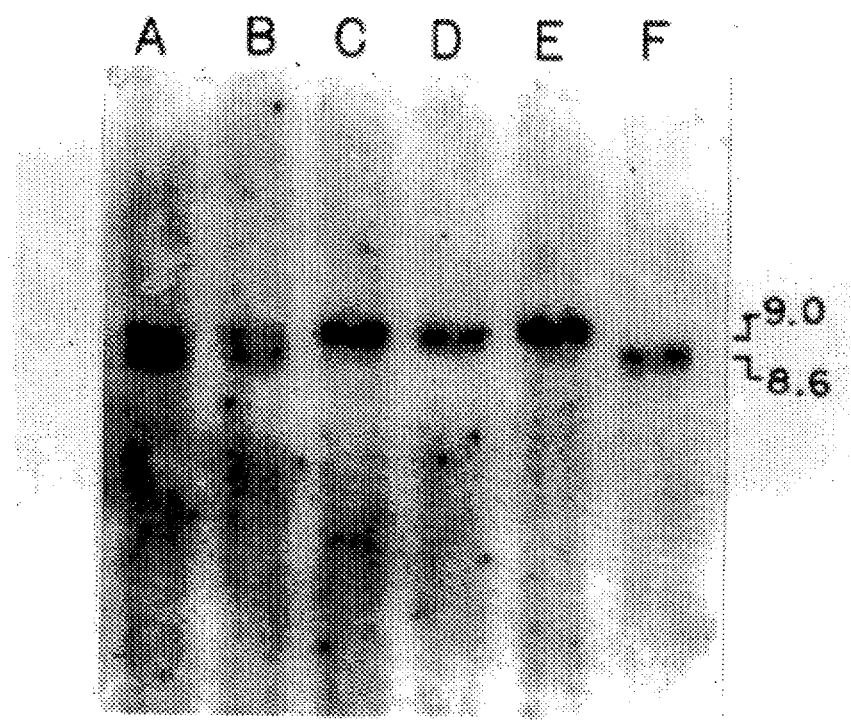

FIG. 9 shows a southern blot analysis of DNAs from the intersubspecies backcross using Pmel 17-1 as hybridization probe. Lanes A–E, individual backcross mice. Lane F, NFS/N.

Figure 10:
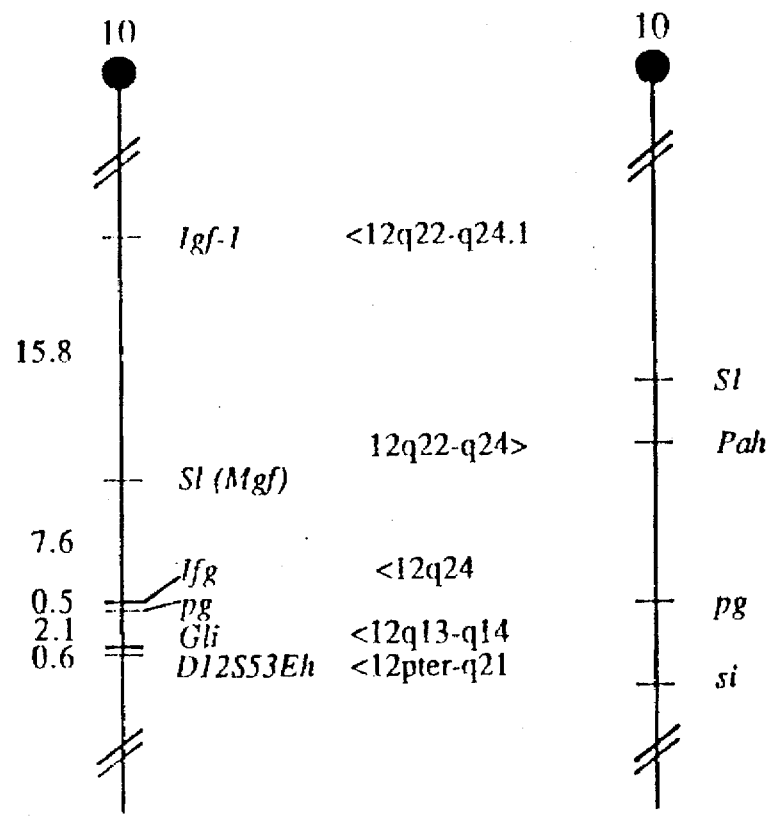

FIG. 10 shows the position of the D12S53Eh locus on mouse Chromosome 10 from an analysis of an interspecies backcross. The segregation patterns of Pmel 17-1 and flanking genes in 167 backcross animals is shown at the top of the figure. For individual pairs of loci, more than 167 animals were typed with the probes shown. Each column represents the chromosome identified in the backcross progeny that was inherited from the (C57BL/6J×M. spretus) $F_1$ parent. The shaded boxes represent the presence of a C57BL/6J allele and white boxes represent the presence of a M. spretus allele. The number of offspring inheriting each type of chromosome is listed at the bottom of each column. A partial Chromosome 10 linkage map showing the location of D12S53Eh in relation to linked genes in the interspecific backcross is shown at the bottom left of the figure. Recombination distances between loci in centimorgans are shown to the left of the chromosome. A partial Chromosome 10 composite linkage map (from GBASE) is shown at the bottom right of the figure. The two maps were aligned at the pg locus. The position of loci mapped in humans is shown between the two maps.

Figure 11:
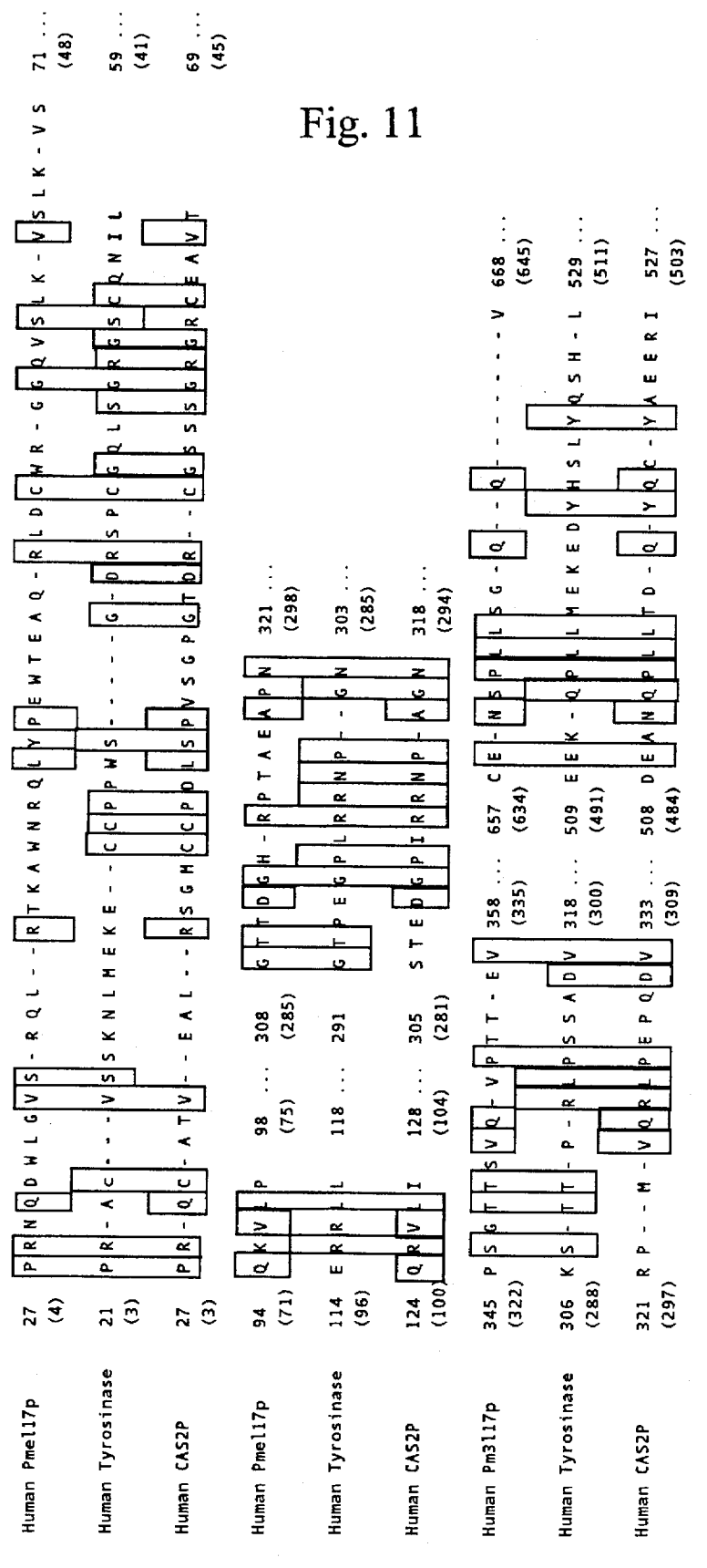

FIG. 11, identified as SEQ ID NO:16, which provides an amino acid comparison of the tyrosinase protein with the amino acid sequence of Pmel-17, shows the alignment of human tyrosinase and Pmel 17 protein (Pmel 17P as shown in SEQ ID NO:1, the numbers corresponding to the position as shown in SEQ ID NO:6) in the homologous regions. The numbers in parenthesis indicate the positions of amino acids from the beginning to end of the homologous region. (•) indicates identical amino acids in these proteins. (+) indicates chemically similar amino acids found in both sequences. Gaps (–) were introduced for a maximum alignment.

Figure 12:
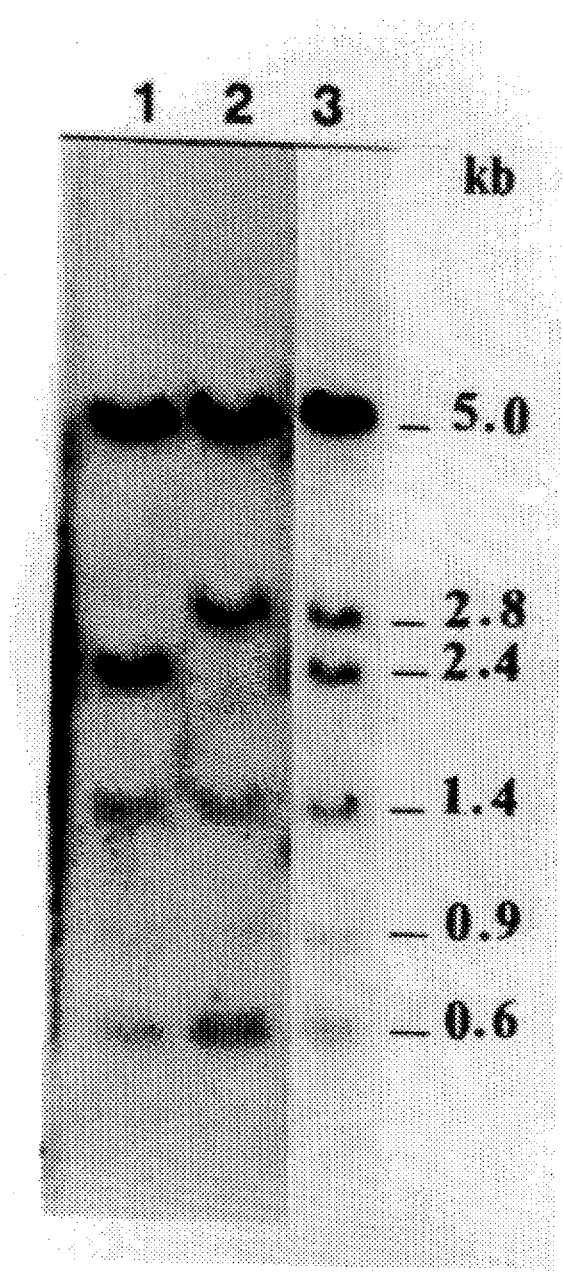

FIG. 12 shows a southern blot analysis of Taq I-digested genomic DNA of a tyrosinase-negative albino proband and his parents. High molecular weight genomic DNA was digested with Taq I, electrophoresed in a 1% agarose gel, transferred to GeneScreenPlus membrane, and hybridized to $3^{32}$P-labeled normal human tyrosinase cDNA Pme134. Lane 1. father; lane 2, mother: and lane 3, proband. Marker sizes are shown in kilobases (kb).

FIG. 13 is a northern blot analysis of poly(A)$^+$ RNA derived from cullures of melanocytic and nonmelanocytic cell lines. (A) Poly(A)+ RNA samples from normal human melanocytes (lane 1), the proband's tyrosinase-negative albino melanocytes (lane 2), human amelanotic melanoma cells (lane 3), human melanotic melanoma cells (lane 4), Jurkat T cells (lane S), and MOLT-3 T cells (lane 6) were fractionated in a formaldehyde/1.4% agarose denaturing gel, blotted onto GeneScreenPlus membrane, and hybridited to $^{32}$P-labeled Pme134. (B) The same blot was stripped and hybridized to nick-transluated human γ-actin cDNA to show the amount of mRNA loaded in each lane. Tyrosinase mRNA was not detected in cells from nonmelanocytic origin (Jurkat and MOLT-3). The difference in the intensity of the tyrosinase bands in A is due to different amounts of poly(A)$^+$ RNA loaded onto the gel as evidenced by subsequent hybridization of the same blot to a γ-actin probe in B.

FIG. 14 shows the sequences shown in SEQ ID NO:7 and SEQ ID NO:8, specifically a nucleotide sequence of normal human tyrosinase cDNA (Pme134A), the deduced amino acid sequence, and the changes predicted on the basis of the identified point mutation in the albino proband as shown in SEQ ID NO:9 and SEQ ID NO:10. Nucleotides are numbered from the first nucleotide of the ATG initiation codon. The deduced amino acids are shown below the nucleotide sequence and are numbered from the amino-terminal amino acid of mature tyrosinase. The amino acid residues of the putative signal peptide are indicated by negative numbers and are heavily underlined. The potential glycosylation sites are underlined in regular print. The putative transmembrane region is doubly underlined. The stop codons are indicated by three dashes. The nucleotide and deduced amino acid sequences downstream from the T insertional mutation (horizontal arrow) in the albino cDNA are shown in italics. The positions of five potentially harmless point mutations are shown by stars, and the nucleotide substitutions and consequent amino acid changes are indicated at fight and are underlined.

Figure 15:
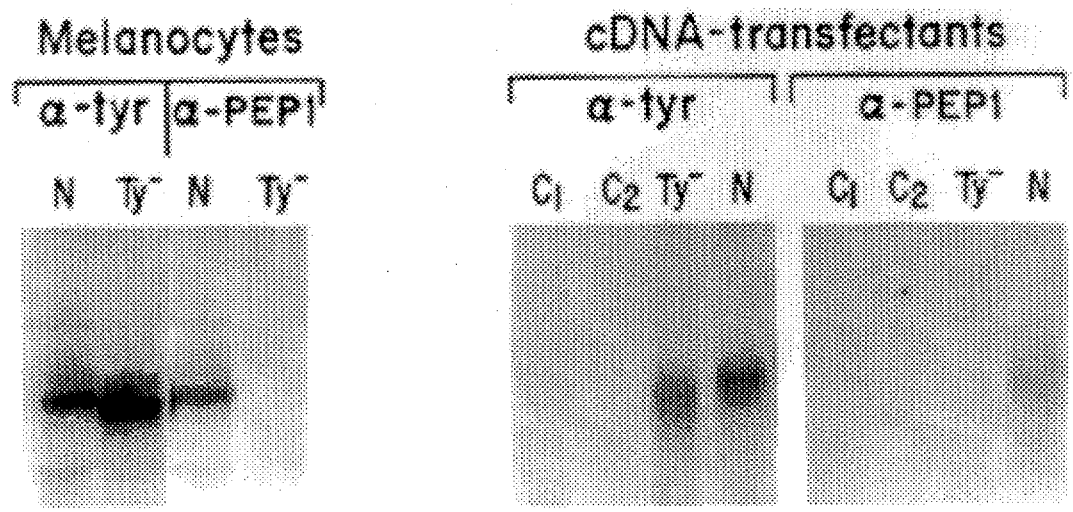

FIG. 15 shows a portion of sequencing gel containing the T insertional mutation. The normal sequence represents Pme134A and the mutant sequence is that of the albino tyrosinase cDNA. The mutation site is indicated by arrows. The sequence is labeled 5' and 3' in reference to the orientation of the tyrosinase gene.

Figure 16:
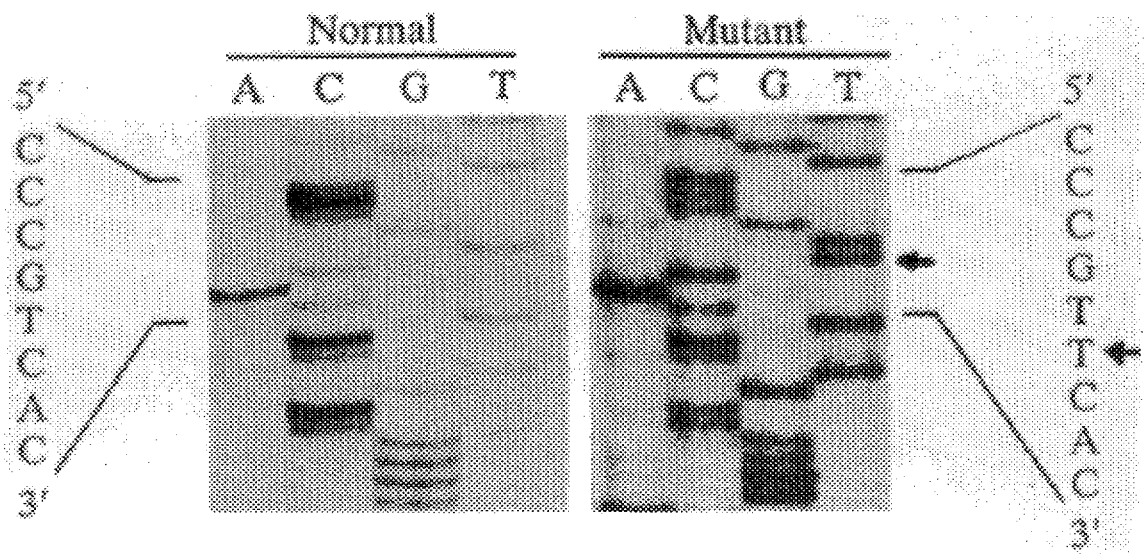

FIG. 16 shows a PAGE analysis of pulse-labeled immunoprecipitated tyrosinase protein. (Left) Tyrosinase from normal (N) and albino (Ty-) melanocytes. (Right) Tyrosinase from normal (N) and albino (Ty-) cDNA-transfected COS-1 cells. Controls: $C_1$, nontransfected; $C_2$, pXM DNA-transfected.

Figure 17:
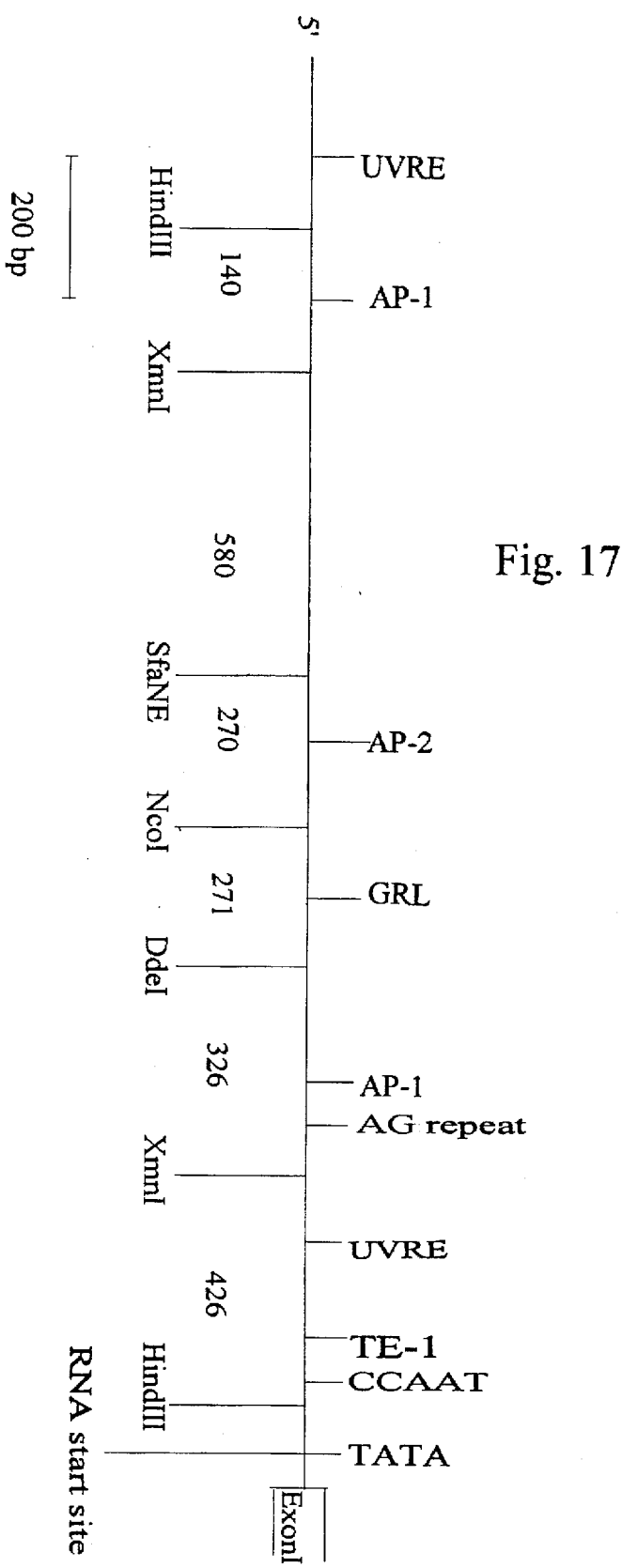

FIG. 17 shows a promoter region of the mouse tyrosinase gene. The restriction sites indicate those used for generating smaller fragments with their lengths in base pairs. The location of cis-acting elements and purine rich domain are shown above.

Figure 18:
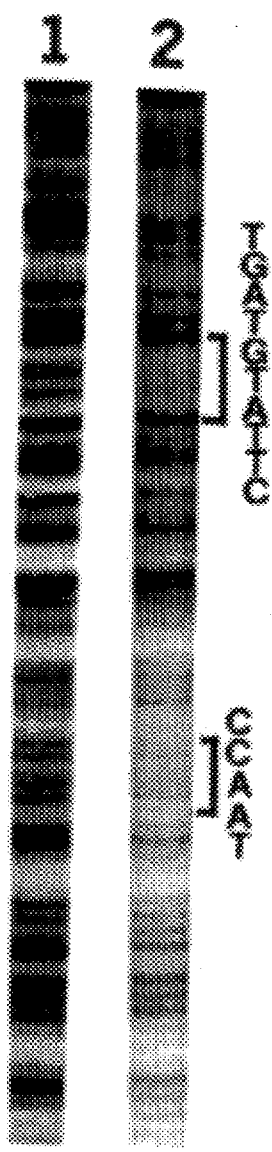

FIG. 18 shows a DNase I footprinting of the 0.4 kb mouse tyrosinase promoter. Lane 1 indicates control pattern of DNase I cleavage with no protein. Lane 2 indicates DNase I protection pattern of B16 melanoma nuclear extract at TE-1 sequence (SEQ ID NO:1) and CCAAT region the relevant sequences being in SEQ ID NO:1.

Figure 19:
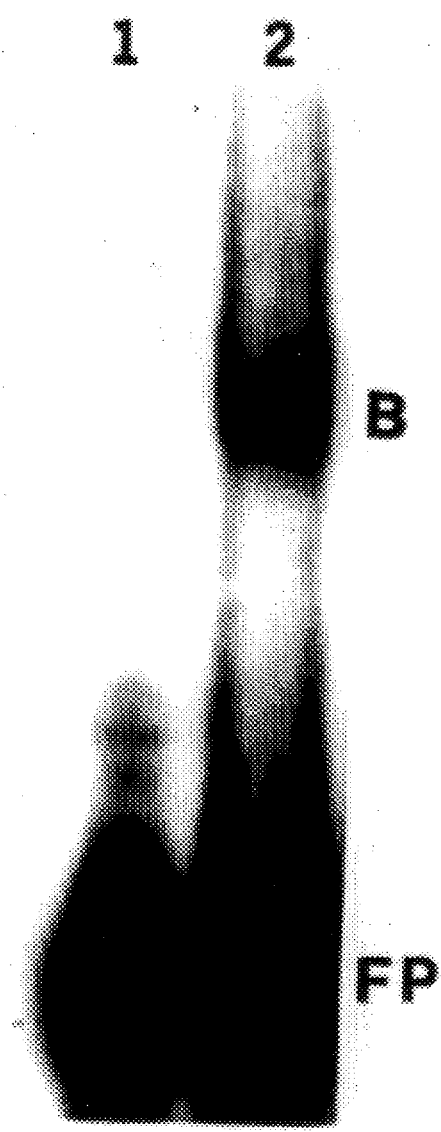

FIG. 19 shows a gel shift assay with affinity purified fraction. 0.2 μg of affinity purified fraction of B16 melanoma nuclear extract using TE-1 sequence was incubated with end labelled TE-1 oligomer and the bound complex resolved on 5% polyacrylamide gels. Lane 1 indicates free probe (F.P) with no protein and Lane 2 indicates binding complex (B) with affinity fraction.

Figure 20:
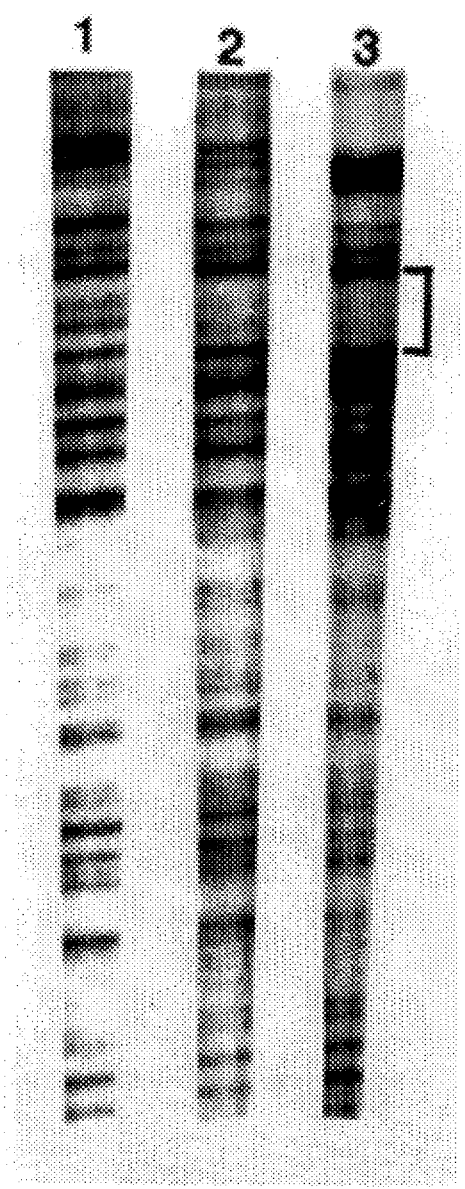

FIG. 20 shows a DNase I footprinting of the 0.4 kb mouse tyrosinase promoter with affinity fraction. 0.2 μg of desalted affinity purified fraction was used in binding reaction followed by DNase I cleavage. Specific protection to TE-1 sequence, indicated in bracket, was observed when affinity fraction was used for binding (Lane 2). Lane 3 shows footprinting with 8 μg of crude nuclear extract of B16 melanoma and Lane 1 indicates control pattern of DNase I digestion of the probe with no protein.

Figure 21:
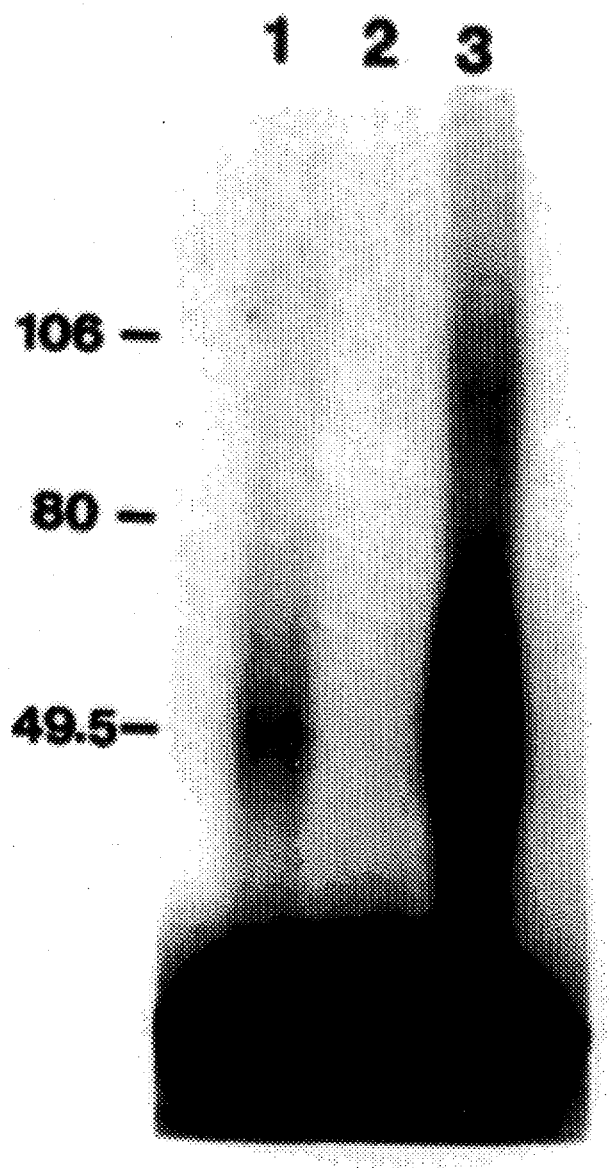

FIG. 21 shows aUV-cross linking of TE-1 oligomer. Both the affinity purified fraction of B16 melanoma nuclear extract with TE-1 sequence and the crude nuclear extract of B16 melanoma exhibit a 49 kD protein binding to TE-1 oligomer as in Lanes 1 and 3 respectively. Affinity purified fraction of B16 melanoma nuclear extract using a non-specific oligomer sequence has not indicated any binding as shown in Lane 2.

Figure 22:
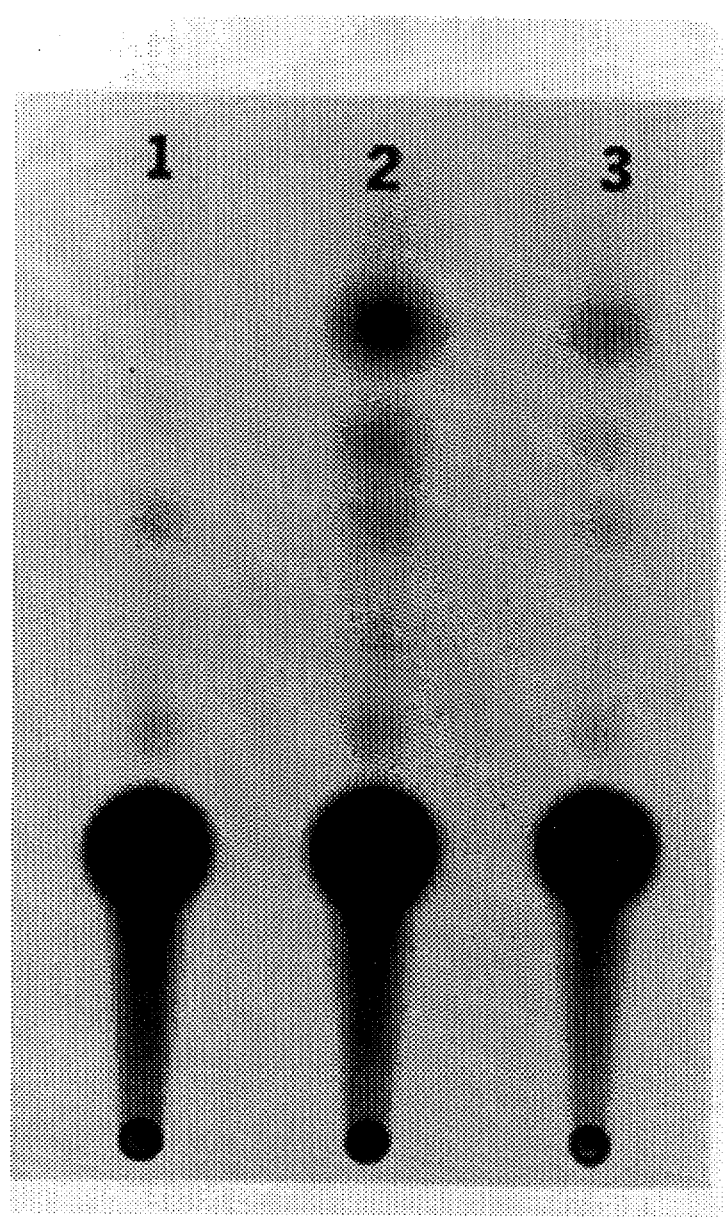

FIG. 22 shows a CAT assay performed with TE-1 sequence in B16 melanoma cells. The double stranded TE-1 oligomer was fused upstream to SV-40 promoter region of a promoter CAT vector and transfected to B16 melanoma cells. The CAT activity indicated a three-fold increase of the reporter gene expression with the construct having TE-1 oligomer (Lane 2) compared to the native plasmid (Lane 3). Lane 1 denotes mock transfection with no plasmid.

Figure 23:
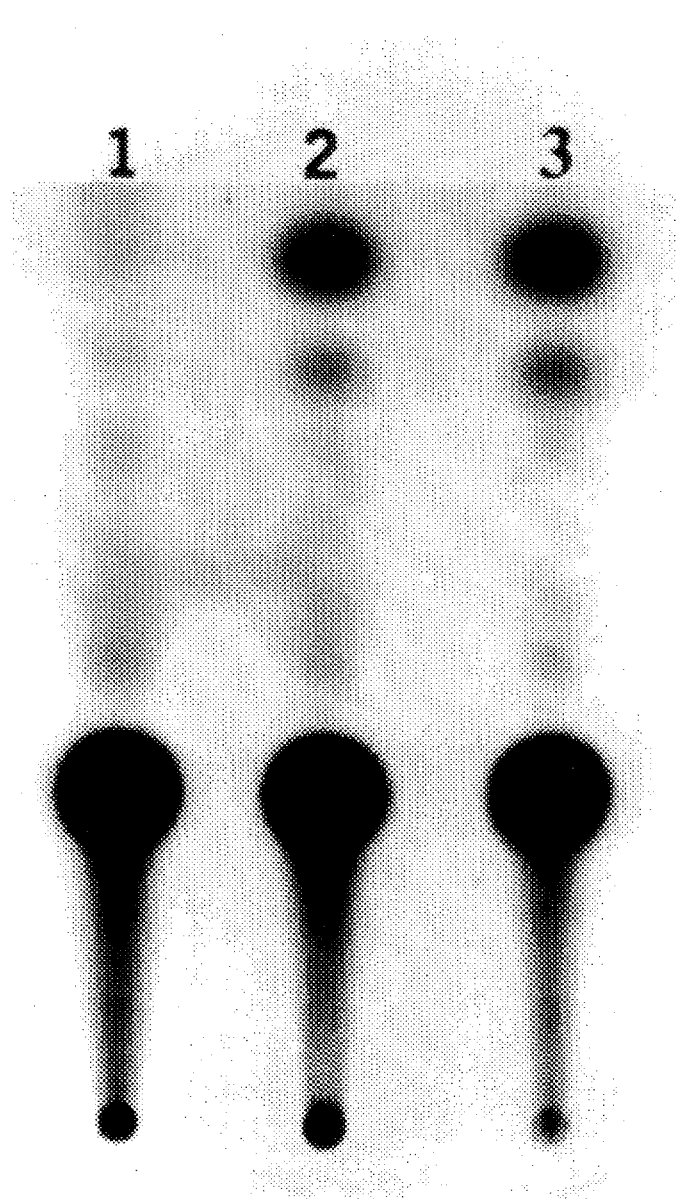

FIG. 23 shows a CAT assay performed with TE-1 sequence in HeLa cells. There was no increase in CAT activity of promoter plasmid construct with TE-1 oligomer (Lane 2) compared to the native plasmid lacking TE-1 sequence (Lane 3) in HeLa cells. Lane 1 indicates mock transfection with no plasmid.

Figure 24:
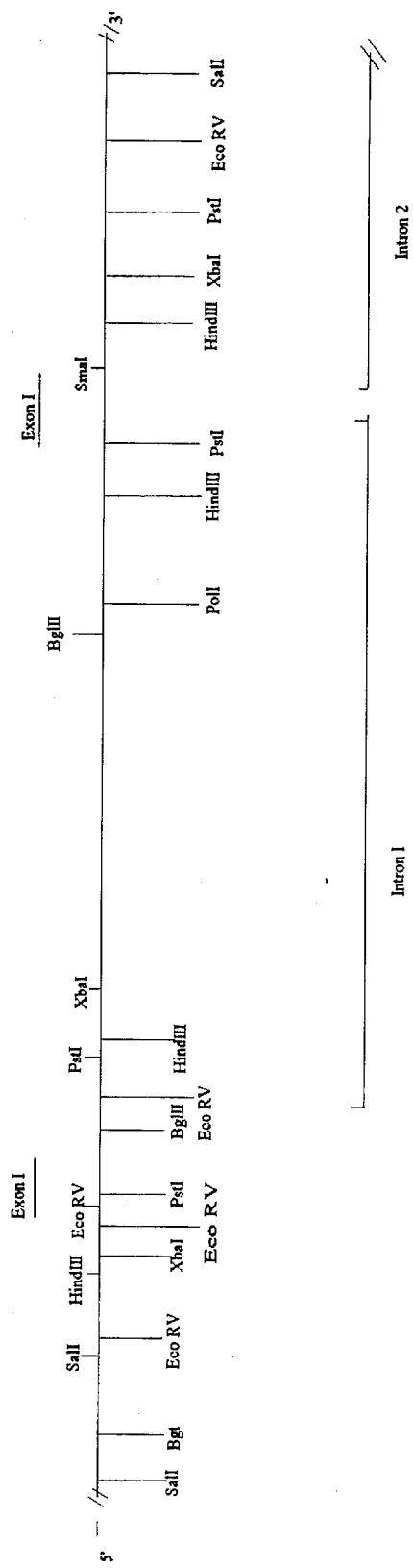

FIG. 24 shows a partial restriction map of cosmid clone (Cos 28A) with a ~40 Kb portion of human tyrosinase gene. The DNA was digested with restriction enzymes indicated in the map and hybridized with oligomer probes representing exons 1, 2 and 3. The relative distance between the enzyme sites and intron exon junctions are as determined by the relative mobilities of fragments.

Figure 25:
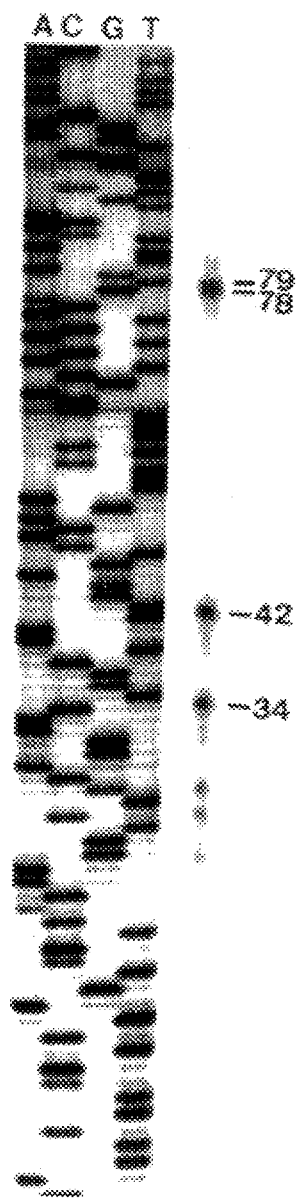

FIG. 25 shows a primer extension analysis to determine the human tyrosinase gene transcriptional initiation site. A 17 base end-labelled oligomer primer, complementary to the coding strand of human tyrosinase gene, 44 bases downstream of ATG, was hybridized with poly(A)+ RNA isolated from Genovese cells and extended using reverse transcriptase. Non-coding strand of the sequencing ladder obtained by extending with the same primer using genomic DNA template is used to locate the precise position of transcriptional start sites.

FIG. 26 shows a nucleotide sequence of the human tyrosinase gene promoter as determined by dideoxy sequencing shown in SEQ ID NO:11. The consensus cis-acting elements are indicated in bold and * denotes transcription start sites as observed by primer extension analysis. ATG codon is indicated by double underline.

Figure 27:
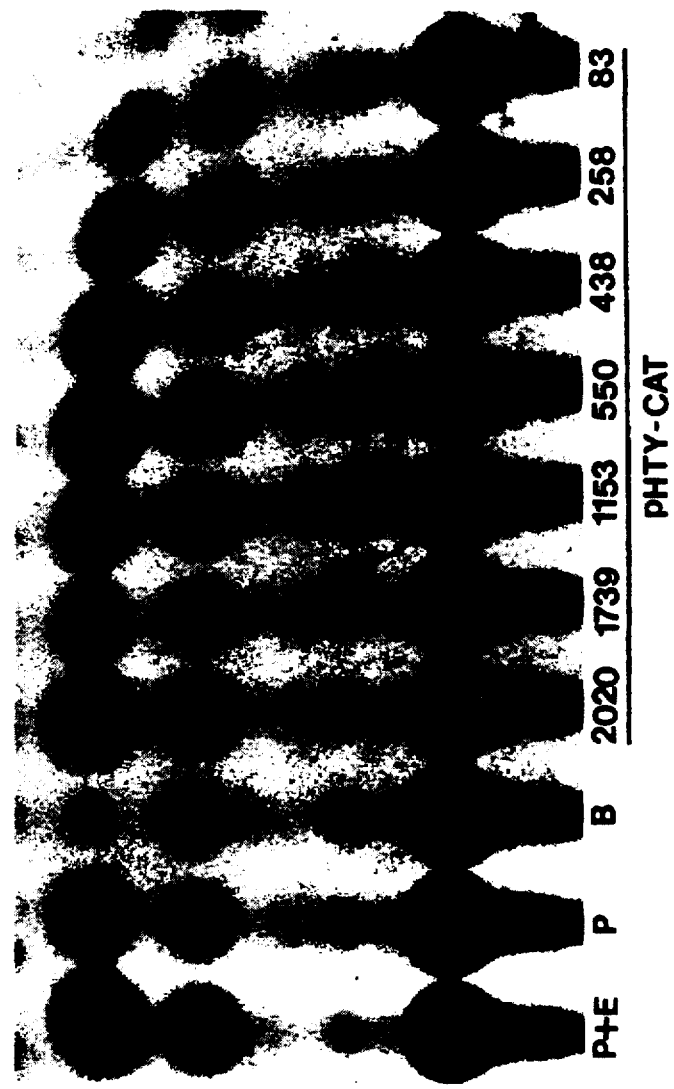

FIG. 27 show a CAT assay of pHTY-CAT reporter gene deletion series in human melanoma cell line. 20 μg of pHTY-CAT plasmids were co-transfected with 2 μg of CMV-β gal DNA on to Stilling cells by electroporation. The cells were cultured for 60 hrs, harvested and cell extracts used for CAT assay. The numbers on each pHTY-CAT plasmid lane denotes the size of the human tyrosinase promoter in kilobase pairs linked to the CAT gene. Transfection with control plasmids pHTY-Promoter and Enhancer (P+E), pHTY-Promoter (P) and pHTY-Basic (B) are indicated in the first three lanes.

FIG. 28 shows a functional analysis of human tyrosinase gene promoter. Plasmids containing different lengths of human tyrosinase promoter fused to the CAT gene were transfected to human (Stilling) melanoma cell line. The relative CAT activities were expressed in terms of percentage. The numbers on the left indicate the length of promoter region linked to the reporter gene.

DETAILED DESCRIPTION OF THE INVENTION

As used herein the following abbreviations are used: Dopa, 3,4-dihydroxyphenylalanie; MSH, melanocyte stimulating hormone; TPA, 12-0-tetradecanoyl-phorbol-13-acetate; IBMX, isobutylmethylxanthien; TBS, 50 m $\underline{M}$ Tris HCL, pH 8.0, 0.15 $\underline{M}$ NaCl; IPTG, isopropyl-beta-D-thiogalactopyranoside; PMSF, phenylmethylsofonyl fluoride; PBS, 0.01 $\underline{M}$ sodium phosphate, pH 7.4, 0.15 $\underline{M}$ NaCl; SDS sodium dedecyl sulfate; PAGE, polyacrylamide gel electrophoresis; SSC, 0.3M sodium chloride, 0.03M sodium citrate; Denhardt, 0.02% Ficoll, 0.02% polyvinylpyrrolidone, 0.02% bovine serum albumin.

Isolation of the λmel 34 cDNA and the λmel 17-1 cDNA

Described herein is the isolation of a cDNA clone for human tyrosinase. Since human tyrosinase has not been sequenced, the following properties of the cDNA lead us to conclude that the mRNA homologous to λmel 34 cDNA encodes authentic human tyrosinase: 1) the protein encoded by the cDNA binds to antityrosinase antibodies; 2) the mRNA corresponding to the cDNA (cRNA) is expressed in melanocytes but not in human neuroblastoma, lymphocytes, fibroblasts or hepatoma cells; 3) the molecular weight of protein encoded by λmel 34 and λmel 34-related cDNA clones is in good agreement with the reported size of de novo form of human tyrosinase (Hermann, W. P and Uhlenbruck, G. (1975) Arch. Dermatol. Res. 254, 275–280., incorporated herein by reference); and 4) the mouse gene corresponding to λ34 cDNA is mapped at the albino locus of the mouse chromosome 7.

The availability of tyrosinase cDNA has opened up a way to investigate the cis-acting regulatory sequence responsible for melanocyte-specific gene expression and the molecular genetic basis of human albinism and the related genetic disorders such as herein discussed (See also: Witkop, C. J., Jr. (1984) In Clinics in Dermatology Vol. 2 (1), pp 70–98, J. B. Lippincott Co., U.S.A., incorporated herein by reference). There are several varieties of human albinism (Witkop, C. J. Jr., Quevodo, W., Jr. and Fitzpatrick, T. B. (1983) In the Metabolic Basis of Inherited Disease. pp 301–346 (Stanbury, J. B., Wyngarden, J. F., Fredrickson, D. S., Goldstein, J. R., Brown, M. S., eds) McGraw-Hill, New York; King, R. A. and Witkop, C. J. Jr. (1976) Nature 263, 69–71; King, R. A., and Witkop, C. J., Jr. (1977) Am. J. Human Genet. 29, 164–168; King, R. A., Olds, D. P., and Witkop, C. J., Jr. (1978) J. Invest, Dermatol. 71, 136–139; King, R. A. and Olds, D. P. (1981) J. Invest. Dermatol. 77, 201–204, each incorporated herein by reference), and in some of them a normal level of hair bulb tyrosinase can be measured. It may be possible, using the cDNA probe, to determine which of the differences are related to mutations in the tyrosinase structural gene and which may be due to mutations which affect synthesis of melanosomes, packaging of enzyme into melanosomes, or degradation of the enzyme. In conjunction with the accumulated genetic information on various mouse mutants affecting coat and eye color, the cDNA probe may be used to classify the molecular genetic nature of the mutations. There are strong indications for the existence of regulatory factors encoded near the mouse albino locus which appear to control various genes that map on other chromosomes, such as liver-specific enzymes and serum proteins (Gluecksohn-Waelsch, S. (1979) Cell 16, 225–237; Schmid, N. Muller, G., Schutz, G. and Gluecksohn-Waelsch, S. (1985) Proc. Natl. Acad. Sci. USA 82, 2866–2869; Loose, D. S., Schaw, P. A., Krauter, K. S., Robinson, D., Englard, S. Hanson, R. W. and Gluecksohn-Waelsch, S. (1986) Pro. Natl. Acad. Sci. USA, 83, 5184–5188, each incorporated herein by reference). Since λmel 34 detects the albino locus in mice this can be a starting material to identify such transacting regulatory genes in mice.

Possession of the cDNA probe for tyrosinase will allow further study of the regulation of tyrosinase synthesis by cAMP, MSH, and other hormones. In those case where mRNA for tyrosinase is increased or decreased, a direct quantitation of mRNA can be made.

Tyrosinase's (EC 1.14.18.1) are copper containing enzymes that catalyze the conversion of tyrosine to dopa to dopaquinone, and thence to melanin (Mason, H. S. (1948) J. Biol. Chem. 172, 83–99, incorporated herein by reference). Several of the mammalian enzymes have been shown to be glycoproteins and to contain sialic acid residues (Miyazaki, K. and Ohtaki, N. (1975) Arch. Derm. Forsch. 252, 211–216; Hermann, W. P. and Uhlenbruck, G. (1975) Arch. Dermatol. Res. 254, 275–280; Nishioka, K. (1978) Eur. J. Biochem. 85, 137–146, each incorporated herein by reference). There are multiple sizes of tyrosinases in all mammalian species which have been studied. These may be caused by differing contents of carbohydrate and as a result of the actions of difference structural genes.

Tyrosinase is an important factor in the development of pigmentation. Oculocutaneous albinism, a group of autosomoal recessive diseases in humans (Witkop, C. J., Jr. Quevedo, W., Jr. and Fitzpatrick, T. B. (1983) In the Metabolic Basis of Inherited Disease. pp 301–346 (Stanbury, J. B., Wyngarden, J. B., Fredrickson, D. S., Goldstein, J. L., Brown, M. S., eds) McGraw-Hill, New York, incorporated herein by reference) and animals, is characterized by reduced or no melanin in skin and eye. However, some people with the condition have as much tyrosinase activity as fully pigmented individuals (King, R. A. and Witkop, C. J., Jr. (1976) Nature 263, 69–71; King, R. A. and Witkop, C. J., Jr. (1977) Am. J. Human Genet. 29, 164–168; King, R. A., Olds, D. P., and Witkop, C. J., Jr. (1978) J. Invest. Dermatol. 71, 136–139, incorporated herein by reference). The albino (C) locus in mice has been mapped to chromosome 7 (Coleman, D. E. (1962) Arch. Biochem. Biophys. 69, 562–568; Gluecksohn-Waelsch, S. (1979) Cell 16, 225–237, incorporated herein by reference).

Studies on the regulation of tyrosinase have focused on the role of MSH in humans and in whole animals (Lerner, A. B. and McGuire, J. S. (1961) Nature 189, 176–179; Pomerantz, S. H. and Chuang, L. (1971) Endocrinol. 87 301–310; Lee, T. H., Lee, M. S., and Lu, M. X. (1972) Endocrinol. 91, 1180–1188, each incorporated herein by reference) and in normal and malignant melanocytes in culture (Halaban, R., Pomerantz, S. H., Marshall, S., Lambert, D. T. and Lerner, A. B. (1983) J. Cell Biol. 97, 480–488; Halaban, R., Pomerantz, S. H., Marshall, S. and Lerner, A. B. (1984) Arch. Biochem. Biophys. 230, 383–387, each incorporated herein by reference). The later studies showed that MSH increased the rate of synthesis of tyrosinase.

A nucleic acid probe for tyrosinase is and will continue to be valuable for a thorough study of the regulation of tyrosinase, the molecular genetic basis of human albinism and of various mouse mutants affecting coat and eye color, and the relationship between melanocyte differentiation and tyrosinase gene expression. Described here is the isolation of a cDNA clone for human tyrosinase which maps at or near the mouse C locus.

EXPERIMENTAL PROCEDURES

Cell culture

Normal human melanocytes were cultured from newborn foreskin by a method modified (Halaban, R. and Alfano, F. C. (1984) In Vitro 20, 447–450, incorporated herein by reference) from that of Eisinger and Marko (Eisinger, M. and Marko, O. (1982) Proc. Natl. Acad. Sci. USA 79, 2018–2022, incorporated herein by reference). The cells were grown in Ham's F-10 medium (American Biorganics) containing 8% fetal calf serum (Gibco), 8% Nu-serum (Collaborative Research), 100 ug/ml penicillin, 200 units/mil streptomycin (Gibco), 85 nM TPA (Consolidated Midland Corp.), 0.1 mM IBMX (Sigma) and 2.5 nM cholera toxin (List Biological Laboratories). In recent experiments cholera toxin was replaced by human placental extract (20 ug/ml) (Halaban, F. Ghosh, S., Duray, P., Kirkwood, J. M and Lerner, A. B. (1986) J. Invest. Dermatol. 87, 95–101, incorporated herein by reference).

Melanoma and neuroblastoma cells were grown in Ham's F-10 medium supplemented with penicillin, streptomycin, 8% fetal calf serum and 8% Nu-serum. The melanoma cell line used was human metastatic LG (melanotic) cultured by us from the brain (Halaban, et al. supra). The human neuroblastoma SK-N-SH (Ross, R. A. and Biedler, J. L. (1985) Adv. Neuroblast. Res. pp. 249–259. (Evans, A. E., D'Ansio. G. J., Seeser, R. D., eds). Raven Press, New York, incorporated herein by reference) was received from Dr. J. L. Biedler, Sloan Kettering Institute, New York, N.Y. The murine neuroblastoma cell line NIE115 was obtained from Dr. X. O. Breakefield, Harvard University, Cambridge, Mass.

To radiolabel proteins of normal melanocytes the cultures were first incubated for 24 hours in methionine-free medium (American Biorganics) supplemented with TPA, cholera toxin, 3% dialyzed calf serum and [$^{35}$S] methionine (Amersham) (100 uCi/ml, 1390 Ci/mole). The cells were lysed with 0.5 ml PBS containing 1% NP-40 (Sigma) and 0.1 mM PMSF (Sigma) and agitated on a vortex mixer. The lysate was centrifuged at 15,000 g for 15 minutes, the specific radioactivity in protein of the supernatant was determined in 5 ul aliquots, and the supernatant was used as a crude radiolabeled tyrosinase preparation.

Preparation of cDNA libraries of normal human melanocytes

Total cellular RNA of normal human melanocytes was prepared by quanidine isothiocyanatecesiumchloride gradient centrifugation essentially as described by Chirgwin et at. (Chirgwin, J. M., Przybyla, A. E., MacDonald, R. J. and Rutter, W. J. (1978) Biochemistry 18, 5194–5299, each incorporated herein by reference). Poly (A)⁺RNA was selected by chromatography on a column of oligo d(T) cellulose (Aviv, H. and Leder, P. (1972) Proc. Natl. Acad. Sci. USA 69, 1408–1412, incorporated herein by reference) (Collaborative Research Type 2). Double stranded cDNAs were prepared from poly (A)⁺ mRNA as previously described (Schwarzbauer, J. E., Tamkun, J. W., Lemischka, I. R. and Hynes, R. O. (1983) Cell 35, 421–431; Land, J., Grez, J., Hauser, H., Lindenmaier, W. and Schutz, G. (1981) Nucleic Acids Res. 9, 2251–2261, each incorporated herein by reference). The cDNA was EcoRI-methylated at internal EcoRI restriction sites with EcoRI methylase (New England Biolabs) (Maniatis, T., Hardison, R. E., Lacy, E., Lauer, J., O'Connel, C., Quon, D., Sim, G. K. and Efstratiadis, A. (1978) Cell, 687–701, incorporated herein by reference) to prevent degradation at the step of EcoRI-linker addition. EcoRI linkers were ligated to both ends of cNDA molecules which were blunt-ended by treating with S1 nuclease followed by E. coli DNA polymerase 1 large fragments. The cDNAs were fractionated on 1 ml columns of Bio-gel A-150m (Bio Rad) and enriched for those composed of over 400 base paris. λgt11 DNA (Young, R. A., and Davis, R. W., (1983) Proc. Natl. Acad. Sci. USA 80, 1194–1198, incorporated herein by reference) was digested with EcoRI and treated with bacterial alkaline phosphatase (Worthington, 0.2u/ug DNA) at 65° for 1 hour to decrease self-ligation. The cDNAs were inserted into the unique EcoRI site of λgt11 cloning vector. The recombinant phage DNA was packaged in vitro as described by Grosveld et al (Grosveld, F. G., Dahl, H. H. M., deBoer, E. and Flavell, R. A. (1981) Gene 13,227–237, incorporated herein by reference). The λgt11 library contained 1.7×10⁶ independent plaques. A pilot experiment showed that 88% of the plaques contained cDNA inserts based on beta-galactosidase activity. The λgt11 cDNA library was amplified in E. coli strain Y1088 (Huynh, R. V., Young, R. A. and Davis, R. W. (1984) In DNA Cloning: A Partical Approach, vol. 1, pp. 49078 (D. Glover, ed.) IRL Press, Arlington, Va., incorporated herein by reference) as a host and stored at 4° C.

Screening for the gene products of the λgt11 melanocyte cDNA library with antityrosinase antibodies The immunobiological screening was carried out as described by Young and Davis (Young, R. A. et al. supra). Recombinant phages were absorbed to bacterial strain Y1090 and plated on 150 mm L-agar plates. The plates were incubated at 42° C. for 3 hours. Nitrocellulose filters, soaked in 50 mM IPTG were placed on the plates and incubated for 3 hours at 37° C. The filters were removed and washed in TBS twice and treated with 20% fetal calf serum in TBS for one hour. The filters were washed with TBS twice and TBS+0.1% NP-40 once. The filters ere incubated with antityrosinase antibodies (available from Dr. Seymour H. Pomerantz, Department of Biological Chemistry, University of Maryland School of Medicine, Baltimore, Md. 21201) in TBS plus 20% fetal calf serum in a sealed plastic bag overnight at 4° C. At the same time another set of IPTG-treated filters were overlayed on plaques and incubated overnight at 37° C. to obtain duplicate filters. The second set of filters were processed the same way as the first set of filters except that the binding period to antityrosinase antibody was two hours at room temperature. Both sets of filters were washed extensively with TBS and TBS plus 0.1% NP-40 at room temperature. [¹²⁵1]protein A (New England Nuclear) was diluted to 1×10⁵ cpm/ml in TBS and incubated with the filters for 1 hour at room temperature with shaking. Filters were washed three times with TBS and blotted dry and autoradiographed with intensifying screen at −70° C.

The duplicate filters were compared to search for positive signals in both filters.

Detection of fusion protein

The lysogens of the recombinant and nonrecombinant λgt11 were prepared employing E. coli strain Y1089 (Huynh, T. V., Young, R. A. and Davis, R. W. (1984) In DNA Cloning: A Practical Approach, vol. 1, pp 49–78 (D. Glover, ed.) IRL Press, Arlington, Va., incorporated herein by reference). The lysogens were grown at 32° C. until they reached logarithmic phase ($OD_{600}$=0.5). Lytic replication was then induced by a temperature shift (42° C., 20 min) and cultures were incubated at 37° for 3 hours in the presence of IPTG at a final concentration of 1 mM. The bacterial cells were suspended in a buffer containing 10 mM Tris HCL pH 7.4, 0.15M NaCl, 1 mM PMSF, 50 ug/ml DNase 1 (sigma) and 50 mg/ml of RHase (Boehringer Mannheim). The soluble fractions of the sonicated bacterial cell suspension were run on a 6% polyacrylamide gel (Laemmli, U. K. (1970) Nature 227, 680–685, incorporated herein by reference).

Immunoprecipitation and competition with antityrosinase antibodies

For competition experiments, antityrosinase antibodies were incubated on ice overnight with bacterial lysates prepare from E. coli Y1089 lysogens of λgt11 or λgt11 plus cDNA. [³⁵S] methionine labeled extract from black foreskin melanocytes (6×10⁶ cpm in protein/assay) was added to each assay tube, followed 15 minutes later by 10 ul of IgGSorb (The Enzyme Center, Inc., 250 mg/ml). At the end of 15 minutes incubation with IgGSorb, the cell lysates were centrifuged at 13,000 g for 0.5 minutes, the pellet of IgGSorb with bound immune complexes washed 3 times with PBS plus 0.1% NP-40 and once with PBS. The immune complexes were eluted from the IgGSorb with sample buffer (Laemmli supra) and subjected to polyacrylamide gel electrophoresis followed by fluorography of the gels as described before (Halaban et al. supra). For quantitation of labeled protein, gel slices were taken from relevant radioactive bands, rehydrated with 25 ul water and digested overnight with 5% Protosol (National Diagnostics) in Econofluor (NEN) at 37° C., and the radioactivity counted.

Northern blot analysis

Poly(A)⁺RNA from normal human melanocytes, melanoma cells, neuroblastoma cell lines, HL-60 (human promyelocytic leukemia cell line) and HepG-2 (human hepatocarcinoma cell line) was fractionated on a 1.2% formaldehyde denaturing gel (Thomas, P. S. (1980) Proc. Natl. Acad. Sci. USA 77, 5201–5205, incorporated herein by reference) and transferred to a nitrocellulose filter or Gene Screen plus membrane (NEN). [³²P] labeled cDNA probes were hybridized overnight to the filter at 42° C. in 5 times concentrated SSC, 50% formaldehyde, 50 mM sodium phosphate buffer pH 6.8, 10% dextran sulfate, Denhardt, 0.1% SDS and 250 ug/ml denatured salmon sperm DNA. Filters were then washed three times for 5 minutes each in 2 times concentrated SSC and 0.1% SDS at room temperature and three times at 42° C. in 5 times concentrated SSC, 5% formaldehyde, 50 MM sodium phosphate buffer pH 6.8, 10% dextran sulfate, Denhardt, 0.1% SDS and 250 ug/ml denatured salmon sperm DNA. Filters were then washed three times for 5 minutes each in 2 times concentrated SSC and 0.1% SDS at room temperature and three times at 42° C. in 0.1 concentrated SSC and 0.1% SDS. The filters were autoradiographed at −70° C. When a Northern blot of Gene Screen plus was used multiple times for hybridization, the previous probe was removed by treating the membrane in 10 mM Tris-HCl pH 7.0 and 0.2% SDS at 85° C. for 1 hour.

Genomic Southern blot analysis

High molecular weight DNAs of murine embryos homozygous for the lethal deletion $c^{3H}/c^{3H}$, heterozygous for the deletion, ($c^{3H}/c^{ch}$) and of normal homozygote chinchilla ($c^{ch}/c^{ch}$), were prepared as described previously (Grass-Bellard, M., Oudet, P. and Chambon, P. (1973) Eur. J. Biochem. 36, 32–38, incorporated herein by reference). $C^{3H}/C^{3H}$ and $c^{3H}/c^{ch}$ mice were obtained from Dr. Gluecksohn-Waelsch at the Albert Einstein College of Medicine and may be purchased from Johnson Laboratories, In., Bar Harbor, Me. Restriction endonuclease digests of DNA were electrophoresed in a 0.8% agarose gel at 4° C. The gel was denatured with 0.5M NaOH/1M NaCl and neutralized with 1M Tris HCl pH 8.0/1M NaCl. The DNA in the gel was transferred to Gene Screen plus as described by Southern (Southern, E. (1975) J. Mol. Biol. 98, 503–517, incorporated herein by reference). For a low stringent hybridization and washing the blot was hybridized with the [$^{32}$P] labeled cDNA in 6 times concentrated SSC, 5 times concentrated Denhardt solution, 0.5% SDS and 100 ug/ml denatured salmon sperm DNA for 24 hours at 58° C. The filters were then washed two time at room temperature for 10 minutes each in 2 times concentrated SSC, 0.1% SDS and two times at 55° C. for 30 minutes each in 2 times concentrated SSC and 0.1% SDS, and two times at room temperature for 30 minutes in SSC.

Isolation of λphage DNA and preparation of inserted DNA

Recombinant phage DNA was prepared as described by Davis et al (Davis, R. W., Botestein, D. and Roth, J. R. (1980) Advanced Bacterial Genetics, pp. 106–107, Cold Spring Harbor Laboratory, Cold Spring Harbor, N.Y., incorporated herein by reference). The recombinant DNA was cut with EcoRI, and the cDNA inserts were separated from λphage arms by 1% agarose gel. The cDNA bands were cut out of the agarose gels, run on 5% polyacrylamide gels, eluted from the gels in 0.1 SSC, and precipitated with ethanol.

DNA Sequencing

DNA restriction fragments, subcloned in M13 vectors (Messing, J., Crea, R. and Seeburg, P. H. (1981) Nucleic Acids Res. 9, 309–322, incorporated herein by reference), were sequenced by the dideoxy chain termination technique (Sanger, F., Nicklen, S. and Coulson, A. R. (1977) Proc. Nat. Acad. Sci. USA 74, 5463–5467, incorporated herein by reference), with modifications made to accommodate 2'-deoxy-adenosine 5'-[alpha-[$^{35}$S] thio]triphosphate (Biggin, M., Gibson, T. and Hung, G. (1983) Proc. Natl. Acad. Sci. USA 80, 3963–3965, incorporated herein by reference).

RESULTS

Isolation of cDNA clones from human melanocyte λgt11 library which react with antityrosinase antibodies A λgt11 cDNA library of normal human melanocytes was screened with rabbit antityrosinase antibodies raised against purified hamster tyrosinase. The antityrosinase antibodies have been shown to cross react with human, murine and avian tyrosinase (Halaban, R., et al. (1983) supra; Halaban, R. et al. (1984) supra). The antibodies immunoprecipitated newly-synthesized as well as processed tyrosinase and were absorbed completely by extracts from melanocytes but not from fibroblasts.

Figure 1:
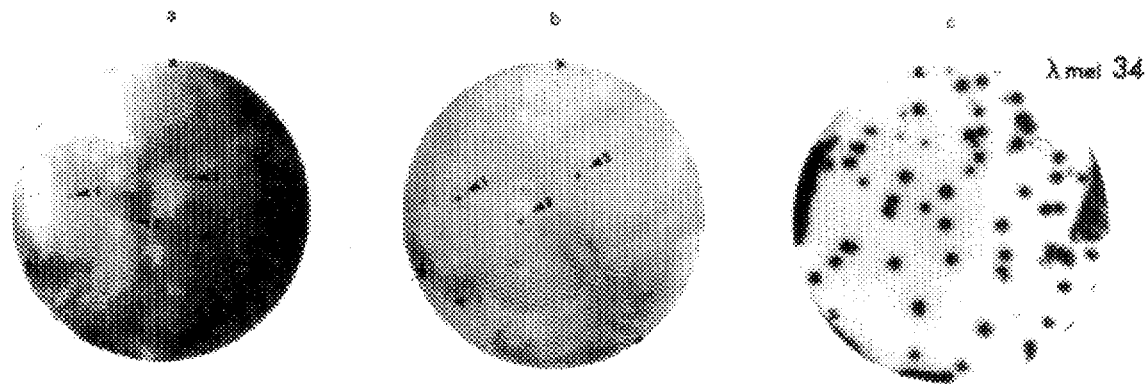
FIG. 1 in three panels depicts the isolation of human tyrosinase cDNA by antibody screening.

Initial screening of approximately 500,000 recombinant phages with rabbit antityrosinase antibodies identified sixteen independent clones which gave positive signals. These clones were consistently reactive with antityrosinase antibodies but not with nonimmune rabbit serum during several rounds of screening for plaques-purification. FIG. 1 shows an example of duplicate primary (a and b) and the third round (c) of screening. FIG. 1 depicts the isolation of human tyrosinase cDNA by antibody screening. A λgt11 cDNA library of human melanocytes was screened with antityrosinase antibody directed against hamster tyrosinase and $^{125}$I-labeled protein A (NEN). Filter panels a and b represent duplicate filters prepared from the same plate of λgt11 cDNA library. Signals in filter a (1, 2 and 3) correspond to those in filter b. It was found that the duplicate screening method was helpful in discriminating false-positive signals. Filter panel c shows the third round of screening during the plaque purification of λmel 34.

Recombinant phage DNAs from each of the 16 clones were prepared, digested with EcoRI to excise the cDNA insert and fractionated on a 1% agarose gel. Sizes of the cDNA inserts varied from 0.2 to 1.6 kb. The longest cDNA insert (§1.6)kb) from λmel 34 was hybridized to 12 other cDNA inserts and shared an overlapping restriction pattern. The other three cDNA inserts were not related to the thirteen cDNA clones. The thirteen cDNA inserts were partially overlapping but none of them were the same clone. The fact that overlapping sequences were found repeatedly indicates that the antibody reacted to the peptides encoded by specific sequences present in the cDNA species. The 1.6 kb cDNA insert of λmel 34 was subcloned into PBR322 to yield pmel 34 and used to amplify the cDNA insert.

mRNA homologous to λmel 34 is expressed preferentially in melanocytes

Figure 2:
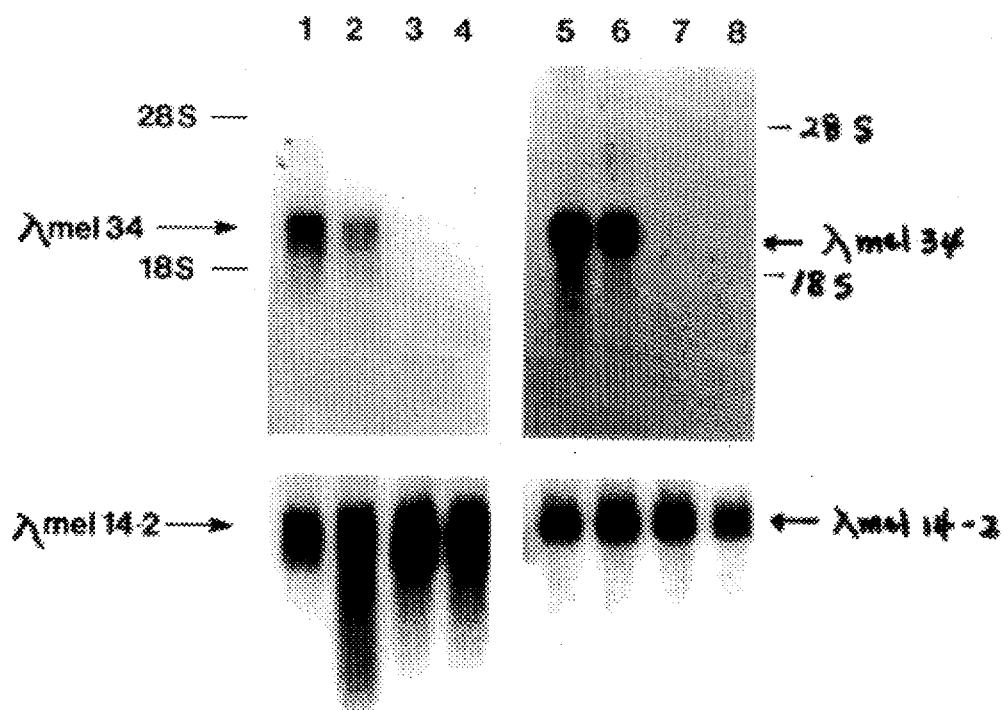
FIG. 2 shows a northern blot analysis of poly(A)$^+$ RNA derived from normal melanocyte, human melanotic melanoma (LC), HePG-2, HL-60, human and mouse neuroblastoma. Blot analysis of poly(A) RNA derived from cultures of melanocytic and nonmelanocytic lineage. Four micrograms of poly(A)$^+$ RNA or normal human melanocyte (lane 1), LG (lane 2), HepG2 (lane 3), and HL-60 (lane 4) cells, and 10 μg of poly (A)$^+$ RNA of normal human melanocytes (lane 5), LG (lane 6), human neuroblastoma (lane 7), and murine neuroblastoma cells (lane 8) were fractionated on a 1.2% (wt/vol) formaldehyde denaturing agarose gel blotted and hybridized with $^{32}$P-labeled Pmel 34. The same filter was used to hybridized to $^{32}$P-labeled Pmel 14-2 to show that each lane contained RNA as indicated above and that the RNA was related.

Tyrosinase is presumed to be expressed only in pigment cells. To examine whether λmel 34 homologous mRNA is expressed only in melanocytes, Northern blot analysis of poly (A)$^+$ mRNA from normal human melanocytes, human melanotic melanoma cells (LG), human neuroblastoma, murine neuroblastoma, HePG-2 (human hepatoma cell line) and HL-60 (human promyelocytic leukemia cell line) was performed using [$^{32}$P] labeled λmel 34 cDNA as a probe. FIG. 2 is a Northern blot analysis of poly (A)$^+$RNA (a) of normal human melanocyte (lane 1), LG (land 2), HepG-2 (lane 3) and HL-60 (lane 4) cells, and 10 ug of poly (A)$^+$ RNA (b) of normal human melanocyte (lane 5), LG (lane 6), human neuroblastoma (lane 7) and mouse neuroblastoma cells (lane 8) were fractionated on 1.2% formaldehyde denaturing agarose gel, blotted and hybridized with [$^{32}$P]-labeled λmel 34 cDNA (upper arrow). The same filter was used to hybridize to [32]-labeled λmel 14-2 (bottom arrow) to show that each lane contained RNA as indicated above and the RNA was relatively intact. λmel 14-2 is a cDNA clone which was isolated from human melanocyte cDNA library and has been used as a control probe because the corresponding RNA was detectable in similar amounts from all human and mouse cells tested. As shown in FIGS. 2a and b, λmel 34 hybridized to 21S (_2.4 kb) mRNA species of normal human melanocytes and human melanotic melanoma cells but not to HePG-2, HL-60, human or murine neuroblastoma mRNA. A cDNA fragment (λmel 14-2) is isolated from melanocyte cDNA library was used as a control probe to show that a similar amount of mRNA was loaded in each lane (FIG. 2a and b). In addition, λmel 34 cRNA was not expressed in other human and mouse fibroblasts and lymphocytes (data not shown). Further studies showed that λmel 34 cRNA expression was correlated with tyrosinase activity and melanin content in human melanoma cells. Amelanotic melanoma cells (no or little melanin-containing cells) expressed far less λmel 34 cRNA than normal or melanotic melanoma cells.

Fusion protein of λmel 34-related clone, λmel 16

Figure 3:
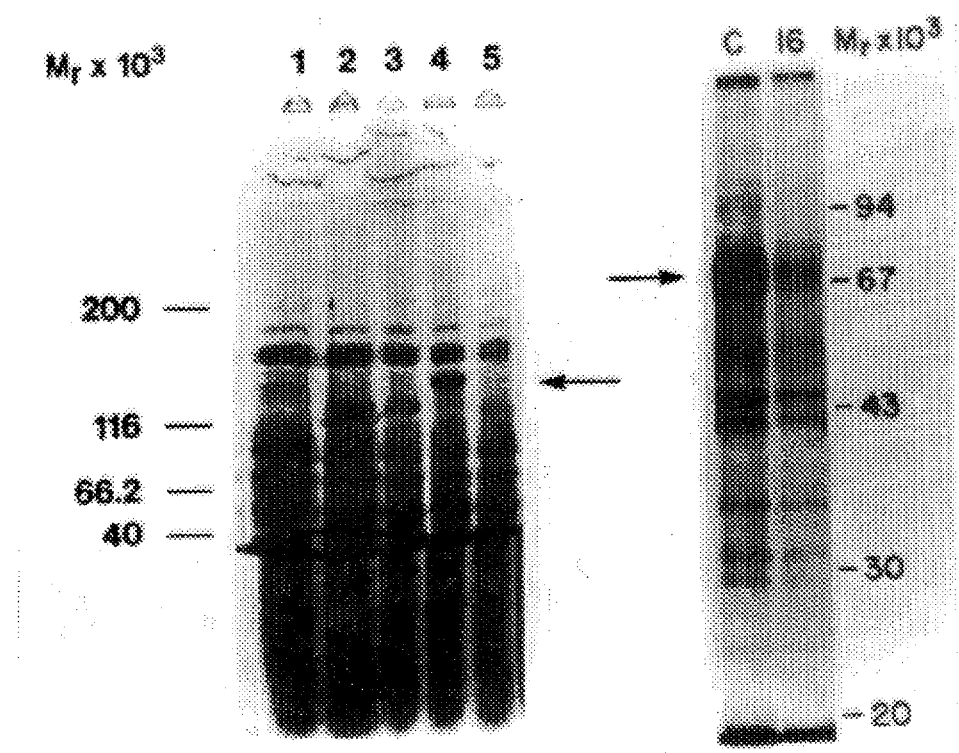
FIG. 3 shows a SDS PAGE presentation of the detection of λmel 16 beta-galactosidase tyrosinase fusion protein. Left: Analysis of lacZ-cDNA fusion proteins. Bacterial lysates were prepared from the lysogens of Y1089/λgt11 (lanes 1 and 2) and Y1089/λmel16 (lanes 3 and 4) and Y1089 alone (lane 5), that were cultured in the absence (lanes 1 and 3) or presence (lanes 2, 4 and 5) of isopropyl β-D-thiogalactopyranoside. Samples were electrophoreses on a 6% NaDodSO$_4$/polyacrylamide gel and stained with Coomassie brilliant blue. The isopropyl β-D-thiogalactopyranoside-dependent production of β-galactosidase (lane 2) and a ~140-kDa λmel16 fusion protein (lane 4, arrow) was noted. Proteins sizes in kDa (Kd) are at the left. Right: Competition immunoprecipitation assay. The lysate of λmel16 or gt11 lysogen was used to compete with metabolically labeled human melanocyte cell extract for anti-tyrosinase antibodies. Equal amounts of lysates of λgt11 lysogen and λmel16 lysogen (~2×10$^7$ bacterial cells in 100-μl volume) were incubated with 5 μl of a 1:100 dilution of anti-tyrosinase antibodies. The respective supernatants were used to immunoprecipitate [$^{35}$S] methionine-labeled human melanocyte extract (6×10$^4$ cpm in protein per tube). The eluted immune complexes were separated on 8.5% NaDodSO$_4$/polyacrylamide gel. In lanes 6 and 15, the antibody preparation was preabsorbed with lysogens λgt11 and λmel16, respectively.

To characterize the fusion protein further, lysogens of λgt11 and λmel 16 (§0.7 kb), which were isolated at an earlier state of this work and which cross hybridized to λmel 34, were prepared and analyzed by 6% SDS PAGE and competitive immunoprecipitation assay. FIG. 3 depicts the detection of λmel 16 beta-galactosidase-tyrosinase fusion protein. Panel a: Bacterial lysates were prepared from the lysogens Y1089/λgt11 (lanes 1 and 2), Y1089/λmel 19 (lanes 3) and Y1089/λmel 16 (lanes 4 and 5) following inactivation of the temperature-sensitive repressor at 42° C. and subsequent incubation in the absence (lanes 1 and 5) or presence (lanes 2, 3 and 4) of IPTG. λmel 16 and λmel 19 were λmel 34-related clones which were isolated in the early phase of this work. Reduced samples were run on a 6% SDS-polyacrylamide gel, and stained with Coomassi-blue. The IPTG-dependent production of beta-galactosidase (lane 2) and ~140 kd λmel 16 fusion protein (lane 5, arrow) was noted. Protein sizes in kilodaltons are marked left. Panel b: The lysate of λmel 16 or λgt11 lysogen was used to compete with metabolically labeled human melanocyte cell extract for antityrosinase antibodies. Constant amounts of lysates of λgt11 or λmel 16 lysogens (~2×10$^7$ cells in 100 ul volume) were incubated with 5 ul of 1:100 dilute of antityrosinase antibodies. The absorbed antibodies were used to immunoprecipitate the [$^{35}$S] labeled human melanocyte extract (6×10$^6$ cpm in protein/tube). The eluted immune complexes were analyzed on an 8.5% polyacrylamide gel. There were 3,780 cpm in control lane and 1,186 cpm in λmel 16 lane, in the gel slices taken from the tyrosinase bands (arrow). As shown in FIG. 3a, a fusion protein was produced in Y1089 (λmel 16) which had a relative size of approximately 140,000 daltons. This was approximately 25,000 daltons larger than that of E. coli beta-galactosidase. This indicates that the cDNA in λmel 16 is fused to beta-galactosidase gene in frame, producing an almost entire protein encoded by the cDNA. Synthesis of both betagalactosidase and the fusion protein was dependent on induction of IPTG. The lysate of λmel 16 lysogen was used to compete with metabolically labeled melanocyte cell extract for antityrosinase antibodies. A typical experiment is shown in FIG. 3B. When bacterial lysates of λgt11 or λmel 16 lysogens (approximately 2×10$^7$ cells in 100 ul volume) were incubated with 1 ul of 1:100 dilution of antityrosinase antibodies, approximately 70% of antityrosinase activity was absorbed by λmel 16 lysate compared with λgt11 control lysates based upon the intensity of tyrosinase bands and radioactivity count of the gel slices taken from tyrosinase bands. Since the antibody preparation if poly-clonal the λmel 16 encoding protein, containing only a partial sequence of tyrosinase, may not bind all of the antityrosinase antibodies.

Gene for λmel 34 is deleted in chromosome of albino locus-deleted mouse, $c^{3H}/c^{3H}$ Earlier studies showed that the skin of mice carrying the albino locus deleted mutant $C^{3H}/C^{3H}$ has no tyrosinase activity (Gluecksohn-Waelsch, S. (1979) supra). However, the tyrosinase activity levels in the skin of mice heterozygous to lethal albino deletions and chinchilla ($c^{3H}/c^{ch}$) were shown to be intermediate between normal ($c^{ch}/c^{ch}$) and mutant ($c^{3H}/c^{3H}$) homozygotes, confirming that the albino locus of mice encodes the structural gene of tyrosinase.

Because the deletion around the albino locus in $c^{3H}/c^{3H}$ mice is large enough to cover the tyrosinase gene (Gluecsolh-Waelsch, S. (1979) supra), authentic tyrosinase cDNA should not detect any band ($c^{3H}/c^{3H}$) mice DNA but should detect hybridizing bands of half normal intensity of the homozygote ($C^{ch}/c^{ch}$) in the heterozygous litter mate ($c^{3H}/c^{ch}$). To test this prediction, genomic DNAs from ($c^{3H}/c^{3H}$), ($c^{3H}/c^{ch}$) and ($c^{ch}/c^{ch}$) were digested with EcoRI and the fragments were separated on 0.8% agarose gel, transferred to Gene Screen Plus, and probed with the [$^{32}$] P-labeled λmel 34 cDNA. After autoradiograph, the λmel 34 cDNA probe was stripped and the same filter was probed $^{32}$P-labeled λmel 17-1 cDNA. λmel 17-1 is one of the three cDNA clones among the initial 16 clones which is unrelated to λmel 34.

Figure 4:
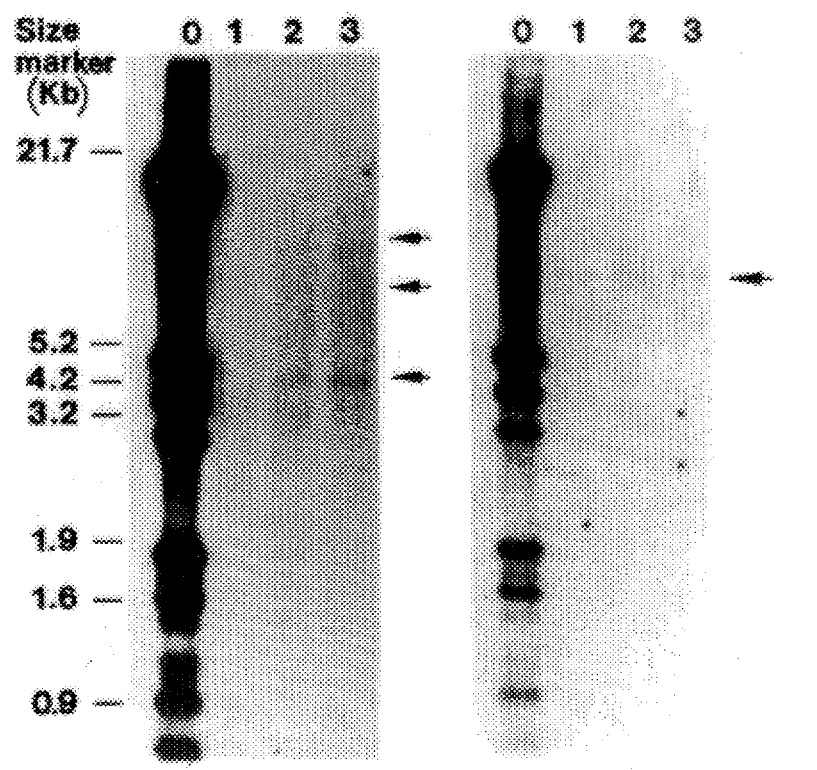
FIG. 4 shows a southern blot analysis of genomic DNA of deletion homozygous (c$^{3H}$/c$^{3H}$) in newborn mice. Genomic DNA from c$^{3H}$/c$^{3H}$ (lane 1), C$^{3H}$/C3h (lane 2) and c$^{cH}$/c$^{ch}$ (lane 3) mice was digested with EcoRI, run on a 0.8% agarose gel, transferred to Gene Screen Plus and hybridized to Pmel 34 (a). The same filter was probed with Pmel 17-1 after stripping Pmel 34 probe (b). Size markers are Hind III fragments of λphage DNA (lane 0).

As shown in FIG. 4a, λmel 34 detected three hybridizing fragments whose sizes were approximately 4.5 kb, 12.0 kb and 14.5 kb in ($c^{ch}/c^{ch}$) DNA. According to the hybridization conditions the mouse tyrosinase gene. Those three bands were also detected in ($c^{3H}/c^{ch}$) at approximately half the intensity of that with ($c^{ch}/c^{ch}$) DNA. No hybridizing fragment was detected in ($c^{3H}/c^{3H}$) DNA even after longer exposure. Therefore, the mouse genes whose sequences are homologous to cDNA contained in λmel 34 are located at or near the albino locus. FIG. 4 is a Southern blot analysis of genomic DNA of deletion homozygous ($c^{3H}/c^{3H}$) (lane 1), ($c^{3H}/c^{ch}$) (lane 2) and ($c^{ch}/c^{ch}$) (lane 3) mice was digested with EcoRI, run on a 0.8% agarose gel, transferred to Gene Screen Plus and hybridized to λmel 34 cDNA (a). The same filter was probed with mel 17-1 after stripping λmel 34 cDNA probe (b). λmel 17-1 is one of the sixteen colones which were initially isolated and proved not to be related to λmel 34. Size markers are Hind III fragments of λphage DNA. As shown in FIG. 4b, λmel 17-1, one of the three other clones initially isolated, detected a 13.0 kb band in all three mouse DNAs at relatively similar intensities. Therefore λmel 17-1 clone is unrelated to the albino locus.

Nucleotide sequence analysis

The entire nucleotide sequence of three overlapping cDNA clones (λmel 34, λmel 16 and λmel 40) was determined according to the strategy shown in FIG. 5. FIG. 5 shows partial restriction map and sequencing strategy for human tyrosinase cDNA. The protein-coding region is indicated by an open box and a putative signal peptide is represented by a shaded box. Horizontal arrows under the 3 inserts show the direction and extent of sequencing used to generate the sequence presented in FIG. 6. Restriction sites used for sequencing are indicated. The scale at the top indicates the nucleotide number. The 5' sides of the other 10 clones were also sequenced. The nucleotide sequence of tyrosinase cDNA revealed a single long open reading frame, beginning with the first nucleotide after the EcoRI linker. This open reading frame is in frame with the lacZ gene of the λgt11 vector. It was found that the other 10 clones are also fused in frame with lacZ gene. This property was helpful in assigning the open reading frame even though the cDNAs did not start the first ATG codon. This reading frame codes for a polypeptide of 560 amino acids with a molecular weight of 63,549 (FIG. 6). FIG. 6 lists nucleotide sequence of cDNA encoding human tyrosinase and its deduced amino acid sequence shown in SEQ ID NO:4 and SEQ ID NO:5 respectively. The nucleotide sequence of message strand is numbered in the 5' and 3' direction. Numbers above each line refer to nucleotide position. Nucleotide residue 1 is the T of the first codon TTC of putative mature protein, and the nucleotides of a portion of putative signal peptide are indicated by negative numbers. The predicted amino acid sequence is shown below the nucleotide sequence. Numbers below the amino acid sequence refer to amino acid position, beginning with the amino-terminal residue of the mature tyrosinase. The preceding residues of a portion of putative signal peptide are indicated by negative numbers. Potential glycosylation signals and potential polyadenylation signals are underlines. - - - indicates stop codon. The codon specifying carboxy-terminal leucine is followed by the translation termination codon TAA (Nucleotide residue, 1645–1647).

No nucleotide differences were observed among the three cDNA clones except that they differ in length. The 3'-untranslated sequence determined from λmel 34, λmel 16 and λmel 40 does not extend as far as the poly(A)$^+$ tail. However λmel 40 contains a potential polyadenylation signal of ATTAAA (Goeddel, D. F., Leung, D. W., Dull, T. J., Gross, M., Lawn, R. M., McCandliss, R., Seeburg, P. H., Ullrich, A., Yelverton, E. and Gray, P. W. (1981) Nature 290, 20–26, incorporated herein by reference) (nucleotide residues, 1822–1827).

Amino acid sequence

The sequence of the first eleven amino acid residues exhibits a feature characteristic of the signal peptide of secretary and membrane-associated proteins (Blobel, G. and Dobberstein, B. (1975) J. Cell Biol. 67, 852–862, incorporated herein by reference), which mainly contains hydrophobic amino acide (9 out of 11) and terminate with serine having a small side chain (Steiner, D. F., Quinn, P. S., Chan, S. J., Marsh, J. and Tager, H. S. (1980) Ann. N.Y. Acid. Sci. 343, 1–16, incorporated herein by reference) (FIG. 6). Therefore, a possible site for cleavage of the signal peptide of putative tyrosinase precursor is after the serine residue at position 1 of phenylalanine (FIG. 6). This prepeptide is probably involved in the transfer of tyrosinase into the melanosome. Thus, mature tyrosinase is composed of 548 amino acids with a molecular weight of 62,160. As tyrosinase is a glycoprotein, the possible N-glycosylation sites were examined. There are five potential aspargine-linked glycosylation signals, Ans-X-Ser-S or Thr, where X is any amino acid except proline (Marshall, R. D. (1974) Biochem. Soc. Symp. 40, 17–26; Bause, E. (1983) Biochem. J. 209, 331–336, incorporated herein by reference). The possible glycosylation sites are the asparagine residues at positions 73, 98, 148, 217 and 324 as underlined in FIG. 6. Tyrosinases contain two copper atoms per enzyme molecule (Nishioka, K. (1978) Eur. J. Biochem. 85, 136–146; Lerch, K. (1976) FEBS Letters 69, 157–160, incorporated herein by reference). Therefore, the possible copper-binding sites were examined by comparison with human (Jabusch, J. F., Farb, D. L., Kerschensteiner, D. A. and Deutsch, H. F. (1980) Biochemistry 19, 2310–2316) and bovine (Richardson, J. S., Thomas, K. A., Rubin, B. H. and Richarson, D. C. (1975) Proc. Natl. Acad. Sci. USA 72, 1349–1353, each incorporated herein by reference) superoxide dismutase. Crystallographic study of bovine superoxide dismutase (Richardson, J. S. et al. (1975) supra) has shown that His-44, His-46, and His-61 are ligands to copper. There are 15 histidine residues in the deduced amino acid sequence of human tyrosinase. Histidine residues at positions 350, 354, 360 and 377 showed a similar arrangement to bovine superoxide dismutase. By analyzing albino and normal human DNA using λ mel 34 as a probe the genetic defect of tyrosinase gene in human albinism will be established. The cDNA contained λmel 34 will be further used to analyze amniotic cell DNA of suspected individuals for prenatal diagnosis of albinism. The cDNA (λmel 34) will be used to produce a pure human tyrosinase by recombinant DNA technology in Bacteria. This will facilitate obtaining a large quantity of pure human tyrosinase. Obtaining a large quantity of pure human tyrosinase is essential to study of the three dimensional structure of the enzyme. Clarification of the tyrosinase structure will lead to establishment of the rational for chemotherapy against malignant melanoma because precursors to melanin is toxic to melanotic melanoma cells.

To produce the tyrosinase in E. coli, λmel 34 cDNA will be fused to an expression vector (Tac) which as T rp and 1 ac promoter together. Tac, the expression vector is available communally through suppliers such as U.S. Pharmacia, Inc. The construct will be expressed in E. coli strain MM294. Subsequently the tyrosinase will be purified by affinity column chromatography.

Subsequently it was found that the cDNA inserts of the three clones which were not related to λmel 34 were cross-hybridized to each other and expressed specifically in melanocytes. This indicates that they were not isolated spuriously, rather that the protein encoded by the cDNAs were reactive to the antityrosinase antibody and had melanocyto-specific functions.

The representative clone ), mel 17-1 detected approximately 2.5 kb mRNA species in only melanocytes. The gene for λmel 17-1 cDNA was not mapped at the albino locus, but it was detected as a single hybridizing restriction fragment in human and mouse DNA, and was highly conserved from mouse to human. The abundance of λmel 17-1 cRNA paralleled the melanin content in human and mouse melanocytes. The expression of λmel 17-1 cRNA was elevated after stimulation of mouse and human melanoma cells with MSH or/and IBMX, and U-V light (such as suntan). This was also closely correlated with the elevation of melanin content. The fact that the λmel 17-1 gene is conserved evolutionarily indicates that the molecule encoded by the λmel 17-1 has biologically important functions. The expression of the gene is controlled by hormones (MSH) or U-V light and positively correlated with the melanin content. These data indicate that the gene is involved in melanin biosynthesis in addition to tyrosinase. Current studies suggest that λmel 17-1 gene product act on melanin biosynthesis's pathway distal to tyrosinase.

Bacteriophage λmel 34 cDNA has been deposited at the America Type Culture Collection under ATC No. 40265 and will be available after this Patent Application issues.

Bacteriophage λmel 17-1 cDNA has been deposited at the American Type Culture Collection under ATC No. 40264 and will be available after this Patent Application issues.

A melanocyte-specific gene, Pmel 17, maps near the silver Coat Color locus on mouse Chromosome 10 and is a syntenic region on human Chromosome 12

METHODS AND MATERIALS

Isolation of cDNA Clones

Because the initial isolate of Pmel 17-1/Pmel 14 was only 1.0 Kb which was clearly not full-length, the human melanocyte cDNA library was rescreened using a cDNA insert of clone Pmel 17-1 to obtain a longer cDNA. Nine overlapping cDNA clones were isolated, and the nucleotide sequences of all of them were determined. The full-length cDNA of Pmel 17-1 is referred to as Pmel 17.

DNA Sequencing Restriction fragments of DNA subcloned in M13 vectors were sequenced by the dideoxy chain termination technique. A forward primer (New England Biolabs) complementary to the lacZ sequence adjacent to the 5' side of the EcoR I site in λgt11 was used for the direct sequencing of the end point of the cDNA insert in λgt11.

Probes

Probes for Pmel 17-1/Pmel 14 were described previously. Probes for the Gli, Ifg, Pah, Igf-1, pg and Sl loci have been described previously (Kinzler, K. W., Ruppert, J. M., Bigner, S. H. & Vogelstein, B. (1988) Nature 332, 371–374; Kozak, C. A., Peyser, M., Krall, M., Mariano, R. M., Kumar, C. S., Pestka, S. & Mock, B. A.(1990) Genomics, 8,519–524; Copeland, N. G., Gilbert, D. J., Cho, B. C., Donovan, P. J., Jenkins, N. A., Cosman, D., Anderson, D., Lyman, S. D. & Williams, D. E. (1990) Cell 63, 175–183, each incorporated herein by reference).

Human/Hamster Somatic Cell Hybrids and Filter Hybridization

The primary chromosome assignment of Pmel 17-1 in the human was carried out with 16 hybrid clones that were derived from eight independent fusion experiments between Chinese hamster (CH) cell lines and human diploid fibroblasts or lymphocytes. The origin and characterization of these hybrids have been summarized (Francke, U., Yang-Feng, T. L., Brissenden, J. E. & Ulrich, A. (1986) Cold Spring Harbor Symposia on Quantitative Biology 51, 855–866; Yang-Feng, T. L., DeGennaro, L. J. & Francke, U. (1986) Proc. Natl. Acad. Sci. USA 83, 8679–8683, each incorporated herein by reference). For regional mapping of Pmel 17-1, a Chinese hamster×human hybrid clone was used with a spontaneous deletion of the distal long arm of human Chromosome 12. The remaining region is 12pter-q21. Genomic DNA was extracted from cultured hybrid cells by routine procedures. Ten micrograms of hybrid and eachparental control cell DNA was digested with a 4-fold excess of Hind III in conditions recommended by the manufacturer.

DNA fragments were separated by agarose gel electrophoresis and transferred to Hybond-N membranes (Amersham) by standard methods. Probes were labeled with $^{32}$P-dCTP by random hexamer priming (Feinbert, A. & Vogelstein, B. (1983) Anal. Biochem. 132, 6–13, incorporated herein by reference). Following the hybridization procedure the filters were washed and autoradiographed as described previously (Barton, D. E., Arquint, M., Roder, J., Dunn, R. & Francke, U. (1987) Genomics 1, 107–112, incorporated herein by reference).

Mouse Gene Mapping and Filter Hybridization

Southern blot analysis was used to type the DNAs from a panel of Chinese hamster and mouse somatic cell hybrids (Hoggan, M. D., Haldon, N. F., Buckler, D. C. & Kozak, C. A. (1988) J. Virol. 62, 1055–1056, incorporated herein by reference) and from the progeny of the intersubspecies backcross [(NFS/N or C58/J×*M. m musculus*) F1×*M. m musculus*]. DNAs were digested by restriction endonucleases, electrophoresed on 0.4% agarose gels, transferred to nylon membranes, hybridized with [$^{32}$P]-labeled probes, and washed as described previously (Jenkins, N. A., Copeland, N. G., Taylor, B. A., Brownell, E., Ihle, J. N., Nagata, S., Jenkins, N. A. & Copeland, N. G. (1988) oncogene Res. 2, 149–165, incorporated herein by reference), and the interspecific backcross [(C57BL/6J×*M. spretus*) F1×C57BL/6J].

Recombination distances were calculated as described by Green (Green, E. L. (1981) in Genetics and Probability in Animal Breeding Experiments (New York: MacMillan), pp. 77–113, incorporated herein by reference) using the computer program SPRETUS MADNESS developed by D. Dave (Data Management Services, Inc., Frederick, Md.) and A. M. Buchberg (NCI-FCRDC, ABLE-BRP, Frederick, Md.). Gene order was determined by minimizing the number of recombination events required to explain the allele distribution patterns.

RESULTS

Sequence Analysis of Pmel 17

FIG. 7A shows the amino acid sequence deduced from the longest open reading frame of Pmel 17 shown in SEQ ID NO:6. The open reading frame codes for 668 amino acids with an Mr of 70,944. The first 23 amino acids are a characteristics of a signal peptide of secretory or membrane-associated proteins and fit the −1, −3 rule (Von Heijne, G. (1983) Eur. J. Biochem. 133, 17–21, incorporated herein by reference) (FIG. 7A, B, and C). Inclusion of a histidine in a signal peptide is unusual, but not unknown. Thus, the protein backbone of processed Pmel 17 would be composed of 645 amino acids with an Mr of 68,600.

Five potential asparagine-linked glycosylation sites are located at amino acid positions 81, 106, 111, 321 and 568 as indicated in FIG. 7A and C. There is a stretch of 26 amino acids that constitutes a hydrophobic domain toward the carboxy terminus of the protein (amino acids 598–623) (FIG. 7A, B, and C). This hydrophobic region is bordered by charged residues at either end ($Glu^{597}$ and $Arg^{624-626}$), consistent with a transmembrane segment that makes a single helical span. One of the striking features of the protein is the relatively high percentage of serines (9.3%) and threonines (9.3%) and their peculiar arrangements. Although serine/threonine residues appear throughout the protein, two sets of His-Ser-Ser-Ser (amino acids 202–205 and 639–642), one Gly-Ser-Ser (amino acids 302–304), four sets of Asp (Asn, Glu)-Thr/Ser-Thr/Ser (amino acids 264–266, 321–323, 370–372, and 425–427), six sets of Leu (Ile, Val, Ala)-Thr/Ser-Thr/Ser (amino acids 298–300, 359–360, 418–420, 441–443, 528–530 and 580–582), five sets of Gly-Thr-Thr (amino acids 308–310, 334–336, 347–349, 386–388 and 412–414), two sets of Pro-Thr-Thr (amino acids 328–330 and 354–356), and two sets of Met-Ser-Thr (amino acids 392–394 and 445–447) were observed. The positions of the above two or three contiguous Ser/Thr-Ser/Thr sequences are indicated in FIG. 7C by asterisks with numbers. In addition, leucine, valine, and glycine are other amino acid residues which are present at high levels in this protein (11.9%, 10.0% and 9.3%, respectively). There are three sets of 26 amino acid motifs in the middle of the molecule (amino acids 315–392) (FIG. 7A and C). Each starts with four identical amino acids (Pro-Thr-Ala-Glu) and has a hydrophobicity pattern (FIG. 7B) similar to the others. The first two sets contain three Thr-Thr or Ser-Thr sequences. The third one contains one Ser-Thr and one Thr-Thr sequence. There is a histidine-rich region in front of the three 26 amino acid repeats and a cysteine-rich region following the repeat motif near the transmembrane domain (FIG. 7C). The significance of such an arrangement of amino acids in this protein remains to be determined. Finally, the relatively short carboxy-terminal putative cytoplasmic domain contains a sequence Cys-X-Cys-Pro (FIG. 7A), which is a binding site of protein tyrosine kinase $p56^{lck}$ (Shaw, A. G., Chalupny, J., Whitney, J. A. Hammond, C., Amrein, K. E., Kavathas, P., Sefton, B. A. & Rose, J. K. (1990) Mol. Cell. Biol. 10, 1853–1862, incorporated herein by reference). It will be interesting to determine whether Pmel 17 protein can bind to protein tyrosine kinases.

Human gene mapping

The human gene was mapped with a panel of Chinese hamster x human somatic cell hybrids which contained different human chromosomes. After hybridization of the $^{32}$P-labeled human Pmel 17-1 cDNA probe to Hind III-digested genomic DNA, a major 3 Kb fragment was seen in human control DNA (FIG. 8, lane HSA), and a larger fragment in Chinese hamster control DNA (FIG. 8, lane CH). In hybrids which contained human Chromosome 12, a 3 Kb band was observed in addition to the Chinese hamster band (FIG. 8, lanes 4, 6, and 8). This band was absent in hybrids not containing human Chromosome 12 (FIG. 9, lane 1–4, 5, 7, and 9). Thus, the presence of the 3 Kb Pmel 17-1 sequence was completely concordant with the presence of human Chromosome 12 in the 16 hybrid cell lines tested. All other chromosomes were excluded by at least two discordant hybrids. The number of discordant hybrids for each human chromosome is listed in parentheses after the chromosome number: 1(2), 2(3), 3(6), 4(4), 5(7), 6(3), 7(5),8(5), 9(5), 10(5), 11(5), 12(0), 13(11), 14(8), 15(5), 16(4), 17(7), 18(6), 19(6), 20(6), 21(3), 22(6), X(2). These results assign the human gene for Pmel 17, termed D12S53E, to human Chromosome 12.

In hopes of localizing this gene more precisely on Chromosome 12, Southern blot analysis was used to examine a hybrid with a Chromosome 12 deletion. The human 3 Kb Hind III fragment was present in this hybrid. This hybrid retains only region 12pter-q21, placing the gene in this region. This hybrid is negative for the human IGF1 locus at region 12q22-q24.1 (Morton, C. C., Byers, M. G., Nakai, H., Bell, G. I. & Shows, T. B. (1986) Cytogenet. Cell Genet. 41, 245–249, incorporated herein by reference).

Mouse Gene Mapping

The Pmel 17-1 clone was used as an hybridization probe to map the murine gene, designated D12S53Eh, in the mouse by analysis of a panel of 25 mouse-hamster somatic cell hybrids. Only two hybrids contained the 8.6 Kb EcoR I fragment of the gene, and these were the only two hybrids in the panel which retained mouse Chromosome 10 (data not shown). Since all other chromosomes were clearly discordant for Pmel 17-1, these data indicate that the murine counterpart of Pmel 17-1, termed D12S53Eh, is on Chromosome 10.

To define a more precise location of D12S53Eh on mouse Chromosome 10, the progeny of an intersubspecies backcross and an interspecies backcross for restriction enzyme polymorphisms were examined using Pmel 17-1 as a hybridization probe as well as other markers on Chromosome 10. Pmel 17-1 identified an EcoR I fragment of 8.6 Kb in the inbred strain parents of the cross between NFS/N and C58/J and 9.0 Kb in the wild mouse-derived *M.m musculus* (Skive) parent (FIG. 9). Thirty-eight of 90 backcross progeny inherited the inbred strain fragment consistent with the expected 1:1 segregation ratio for a single gene. Comparison with the other markers previously mapped on Chromosome 10 indicates that the mouse homologue of this gene is at the distal end of Chromosome 10 with gene order Ifg-Gli-D12S53Eh (Table 1).

TABLE 1

Segregation of the Pmel 17 hybridizing restriction fragment with alleles of Ifg and Gli in 90 progeny of an inter subspecies backcross.

| Mice | Inheritance of the NFS/N allele | | | |
|---|---|---|---|---|
| | Ifg | Gli | Mel | No. of Mice |
| Parental | + | + | + | 32 |
| | − | − | − | 51 |
| Single recombinant | + | + | − | 1 |
| | − | − | + | 2 |
| | + | − | − | 0 |
| | − | + | + | 4 |

| Locus pairs | Recombination | |
|---|---|---|
| | r/n | % recombination ± SE |
| Ifg, Gli | 4/90 | 4.4 ± 2.2 |
| Gli, Mel 17 | 3/90 | 3.3 ± 1.9 |

Percentage recombination between restriction fragments and SE were calculated according to Green (1981) from the number of recombinants (r) in a sample size of n.

Analysis of interspecies backcross progeny derived from the cross [(C57BL/6J×*Mus spretus*) F1×C57BL/6J] confirmed the Chromosome 10 localization of Pmel 17-1. Pmel 17-1 detected 6.6 and 3.7 Kb Bgl I fragments in C57BL/6J DNA and 14.0 and 2.4 Kb Bgl I fragments in *M. spretus* DNA. The *M. spretus* Bgl I RFLPs were used to follow the segregation of the D12S53Eh locus in backcross mice. In order to position Pmel 17-1 on the linkage map, 167 backcross mice randomly selected from 205 progeny were typed for three additional loci. These three additional flanking loci were insulin-like growth factor 1(Igf-1), steel (Sl), and pygmy (pg). The positions of these flanking loci on the interspecific linkage map have been determined previously. In addition to the 167 backcross animals typed for all six loci, up to 191 mice were typed for some pairs of loci. Each locus was analyzed in pairwise combinations for recombination frequencies using the additional data as shown in FIG. 10.

The ratios of the total number of mice exhibiting recombinant chromosomes to the total number of mice analyzed for each pair of loci and the most likely gene order are: centromere-Igf-1 (insulin-like growth factor-1)-29/184-Sl (steel)-14/185-Ifg (interferon gamma)-1/191-pg (pygmy)-4/188-Gli (glioblastoma oncogene)-1/183-D12S53Eh (Pmel 17-1). The recombination frequencies expressed as genetic distances in centimorgans (cM)±the standard errors are Igf-1-(15.8±2.7)-S1-(7.6±1.9)-Ifg-(0.5±0.5)-pg-(2.1±1.1)-Gli-(0.6±0.5)-D12S53Eh. There is a known locus distal to the Gli locus which affects mouse coat color and is called si or silver locus. The data indicate the possible localization of D12S53Eh near the si locus (Green, M. S., (1989) in Genetic Variants and Strains of the Laboratory Mouse, eds. Lyon, M. F., & Searle, A. G. (Oxford University Press, Oxford), pp. 12–403, incorporated herein by reference).

DISCUSSION

The overall makeup of the Pmel 17 protein is similar to tyrosinase, in that it has a signal sequence at the amino terminus and a transmembrane domain toward the carboxy terminus. A limited amino acid homology was found between the Pmel 17 protein and tyrosinase. As shown in FIG. 11, identified as SEQ ID NO:16, there are two regions of homology in the two proteins; one in the amino-terminal portion and the other in the middle of both molecules. Comparatively, the amino acid identity of the homologous regions is 41% in the amino-terminal portion and 38% in the mid-portion. Taking into account discrepancies between chemically similar amino acids, the homology is 63–64% in both regions. Direct sequence analysis with a λgt11 forward primer revealed that the open reading frame of Pmel 17-1 (a partial cDNA clone used for mapping) was in the frame with the lacZ gene of the λgt11 vector. This open reading frame of Pmel 17-1 spans from amino acid 141 to amino acid 435 of the Pmel 17 protein. The homology in the middle of the proteins might explain why polyclonal anti-tyrosinase antibodies recognized the Pmel 17-1 protein.

The significance of the peculiar appearance of the serines and threonines is not known. It is possible that the serine/threonine residues might be sites for phosphorylation, which would be a potential means for the regulation of the activity of this protein, or might be sites for O-glycosylation.

A short stretch of amino acids can mediate certain functions of a protein such as Arg-Gly-Asp in osteopontin which represents a cell attachment site (Oldberg, A., Franzen, A. & Sakakura, R., Tager, C., Chaudhuri, B. & Muller, R. (1986) Proc. Natl. Acad. Sci. USA 83, 8819–8823, incorporated herein by reference). The Pmel 17 protein contains the 4 amino acids Arg-Ala-Leu-Asp (amino acids 223–226). An identical series is also present in the mouse b-protein encoded by the murine brown locus (amino acids 146–149) and in the human gp75 protein encoded by CAS2 locus (amino acids 146–149) (Cohen, T., Muller, R., Tomita, Y. &

Shibahara, S. (1990) Nucl. Acids Res. 18, 2807–2808, incorporated herein by reference, unpublished observation). Apart from the parallel of the short stretch of identical amino acids, the Pmel 17 and brown-locus protein are different. The fact that the 4 amino acids are found in an identical pattern in these proteins may indicate that they have certain properties in common and may ultimately provide a clue to determining their function.

Previous studies showed that the Pmel 17 gene expression is more closely correlated with the level of melanin content than is tyrosinase expression. This suggests that Pmel 17 protein may function as a catalyst of melanin biosynthesis at a step distal to tyrosinase. It has been suggested that there are several steps at which enzymes other than tyrosinase could be involved; for example, dopachrome isomerase has been demonstrated to be involved in catalyzing dopachrome to 5,6-dihydroxyindole (Korner, A. M. & Pawelek, J. (1980) J. Invest. Dermatol. 75, 192–195, incorporated herein by reference). The dopachrome isomerase is known to be inducible by β-melanotropin and IBMX, and the molecular size has been determined to be 81 kD (John Pawelek, personal communication). The Pmel 17-deduced protein could be 81 kD taking into account that the glycosylation and the Pmel 17 mRNA are inducible by β-melanotropin and IBMX. Such properties are similar to those of dopachrome isomerase. The most frequent form of oculocutaneous albinism is the tyrosinase-positive form. Since tyrosinase is active, there must be other factors affected. A gene involved in melanogenesis distal to tyrosinase could be a candidate gene for a defect involved in tyrosinase-positive albinism.

Human Chromosome 12 is known to contain a region of linkage homology (12p11-qter) to the distal region of mouse Chromosome 10 (Nadeau, J. H. (1989) Trends Genet. 5, 82–86, incorporated herein by reference). The human homologues of the mouse markers used to position D12S53Eh in the mouse PAH, IGF 1, IFG, and GLI are conserved in a syntenic group on human Chromosome 12q. In humans, PAH maps to 12q22-q24, IGF 1 to 12q22-q24.1, IFG to 12q24, and GLI to 12q13-q14 (Lidsky, A. S., Law, M. L., Morse, H. G., Kaw, F. T., Rabin, M., Ruddle, F. H. & Woo, S. L. C. (1985) Proc. Natl. Acad. Sci. USA 82, 6221–6225; Arheden, K., Ronne, M., Mandahl, N., Helm, S., Kinzler, K. W., Vogelstein, B. & Mitelman, F. (1989) Hum. Genet. 82, 1–2, each incorporated herein by reference). The assignment of D12S53Eh distal to these markers extends this region of known homology on mouse Chromosome 10.

In FIG. 10, the interspecific linkage map is aligned with the composite linkage map (provided from GBASE, a computerized database maintained at The Jackson Laboratory, Bar Harbor, Me.) using the pg locus as an anchor. This alignment places D12S53Eh near the si (silver) coat color locus that has been mapped to the distal region of Chromosome 10 by conventional intraspecific crosses (FIG. 10). Nonagouti hairs of homozygous silver mice may be all white, all black, black with white tips, or white with gray or black bands. Silvering results from a reduction in the number of pigment granules (Dunn, L. D. & Thigpen, L. W. (1930) J. Hered. 21, 495–498, incorporated herein by reference). The phenotype of si would be consistent with a defect in a melanocyte-specific gene such as D12S53Eh. Whether the si locus encodes the mouse homologue of Pmel 17 and, therefore, the mouse Pmel 17 protein represents the si protein remains to be determined.

The DNA sequence ceding for the protein Pmel 17 and fragments and derivatives thereof: 1) can be used as a probe for similar ceding sequences; 2) can be used as a probe for genetic analysis of human albinism; 3) can be used as a probe for the diagnostics of prenatel albinism; 4) can be used as a probe for carder detection of albinism; 5) can be used as a probe to develop systems which can find chemicals or factors regulating skin coloration; 6) can be used to control production or regulation of human melanin; 7) can be used to prevent hypopigmentation in hair; or 8) can be used to prevent hair loss.

A Single Base Insertion in the Putative Transmembrane domain of the Tyrosinase Gene as a Cause for Tyrosinase-Negative Oculocutaneous Albinism

MATERIALS AND METHODS

Cell Cultures

Tyrosinase-negative albino melanocytes from the proband and normal human control melanocytes were cultured from shaved skin biopsy samples. The melanocytes were grown in Ham's F-10 medium (American Biorganics, North Tonawanda, N.Y.) supplemented with penicillin (200 units/ml), streptomycin (100 μg/ml), L-glutamine (1 mM), newborn calf serum (2.5%), and calf serum (2.5%) (both from GIBCO), phorbol 12-myristate 13-acetate (85 nM, Chemsyn Science Laboratories, Lenexa, Kans.), 3-isobutyl-1-methylxanthine (0. 1 mM, Sigma), insulin (5 μg/ml), and bovine pituitary extract (40 μg/ml). Jurkat and MOLT-3 are T-cell leukemia lines and were cultured in RPMI 1640 medium supplemented with fetal bovine serum (10%) streptomycin (100 μg/ml), and penicillin (100 units/ml). COS-1 cells were grown in Dulbecco's modified Eagle's medium containing fetal bovine serum (10%), penicillin (100 units/ml), and streptomycin (100 μg/ml).

Southern Blot Hybridization

High molecular weight human genomic DNA was prepared. DNA digested with Taq I restriction endonuclease was electrophoresed in 1% agarose gels at 4° C., transferred to GeneScreenPlus membrane (DuPont/NEN) as described by Southern, and hybridized to $^{32}$P-labeled normal human tyrosinase cDNA Pme134 at 65° C. The blot was then washed twice in 2× standard saline citrate (SSC) for 5 min at room temperature, twice at 65° C. in 2× SSC/1% SDS for 30 min, and twice with 0.1× SSC for 30 min at room temperature. The blot was autoradiographed for 2 days at −80° C.

RNA Blot Analysis

Poly(A)$^+$ RNA samples from normal human melanocytes, the proband tyrosinase-negative albino melanocytes, human melanotic and amelanotic melanoma cells, and Jurkat and MOLT-3 were fractionated in formaldehyde/1.4% agarose denaturing gels and transferred to GeneScreenPlus membrane. The blot was hybridized to nick-translated normal human tyrosinase cDNA Pme134 in 50% (vol/vol) formamide/10% (wt/vol) dextran sulfate/1M sodium chloride/1% (wt/vol) SDS containing 100 μg of sheared salmon sperm DNA per milliliter.

Construction and Screening of cDNA Library

The normal tyrosinase cDNA library was constructed and screened. A cDNA library was also prepared from poly(A)$^+$ RNA derived from the proband's tyrosinase negative albino melanocytes and cloned in a λgt11 cloning vector. The latter library was screened with two different $^{32}$p,labeled oligomers, which represented the 5' and 3' ends of normal tyrosinase cDNA.

DNA Sequencing

Restriction fragments of cDNA from normal human melanocytes were subcloned into a M13 vector for sequence determination by the dideoxy chain-termination method. The albino tyrosinase cDNAs were sequenced by the double-stranded sequencing method (Chen, E. Y. & Seeburg, P. H. (1985) DNA 4, 165–170, incorporated herein by reference.) using various oligonucleotides corresponding to different regions of the tyrosinase cDNA. The 3' region of the Bgl II-EcoRI fragment of the albino tyrosinase cDNA was subcloned into the M13mpB BamHI/EcoRI site and sequenced by the dideoxy chain-termination method.

Tyrosinase Assay

Tyrosinase activity was determined in anagen hair bulbs as described by King and Witkop (King, R. A. & Witkop, C. J., Jr. (1976) Nature (London) 362, 69–71, incorporated herein by reference.). Tyrosinase activity in melanocyte extracts was measured by the method of Pomerantz (Pomerantz, S. H. (1969) Science 164, 838–839, incorporated herein by reference.); 1 unit of enzymes defined as the activity that catalyzes the oxidation of 1 μmol of tyrosine per minute.

Immunoprecipitation

Melanocytes in culture were deprived of methionine and cysteine for 4 hr and pulsed for 15 min with Trans$^{35}$S-label (500 μCi/ml; ICN). The cells were lysed in phosphate-buffered saline (PBS: pH 7.4)/1% (vol/vol) Nonidet P-40/0.1% (wt/vol) SDS/0.1 mM phenylmethylsulfonyl fluoride and subjected to immunoprecipitation with either polyclonal anti-tyrosinase antibodies raised in rabbits against hamster tyrosinase (α-tyr) or with antibodies raised against a synthetic peptide spanning the carboxyl-terminal 15 amino acids of mouse tyrosinase (α-PEP7, a gift from V. J. Hearing, National Cancer Institute, Bethesda, Md.; Jimenez, M., Tsukamoto, K. & Hearing, V. J. (1991) J. Biol. Chem. 266, 1147–1155, incorporated herein by reference.). Twelve of these 15 amino acids are identical in murine and human tyrosinase. Immune complexes were resolved by PAGE and fluorographed at −75° C. for 1 or 2 days (α-tyr, (r-PEP7, respectively).

Transfection of COS-1 Cells with Normal and Albino Tyrosinase cDNA

COS-1 cells were grown to 30–50% confluency in Dulbecco's modified Eagle's medium as described above and transfected by the DEAE-dextran method (Selden, R. F. (1989) in Current Protocols in Molecular Biology, eds. Ausubel, F. M., Brent, R., Kingston, R. E., Moore, D. D., Seidman, J. G., Smith, J. A. & Struhl, K. (Wiley, New York), Vol. 1, pp. 9.0.1–9.9.6, incorporated herein by reference.) with 4 μg of plasmid DNA containing normal and albino tyrosinase cDNA inserts. Normal tyrosinase cDNA clone Pme134 lacks nucleotide A of the first ATG codon. Therefore, a new clone, Pme134A, was constructed which contained the initiation ATG codon, by replacing the 5'-end EcoRI-HgiAI fragment of Pme134 with the corresponding fragment containing the first ATG codon. This construct and the albino cDNA were ligated to expression vector pXM (Yang, Y. C., Cirlelta, A. B., Temple, P. A., Chung, M. P., Kovacic, S., Witek-Giannolti, J. A., Leary, A. C., Kriz, R., Donahue, R. E., Won, G. G. & Clark, S. C. (1986) Cell 47, 3–10, incorporated herein by reference.) and used in the transfection of COS-1 cells.

Forty-four hours after transfection, the cells were incubated for 4 hr in methionine/cysteine-free medium and pulsed with Trans$^{32}$S-label (500 μCi/ml) for 15 min. The cultures were washed twice with PBS, harvested by scraping, and lysed in PBS/1.0% Nonidet P-40/0.1% SDS with protease inhibitors (phenylmethylsulfonyl fluoride, 1 mM; leupeptin, pepstatin, chymostatin, and bestatin, each 1 μg/ml) for 2 hr on ice. The lysates were centrifuged at 10,000× g for 10 min. The supernatants were used for immunoprecipitation as described above.

RESULTS

Taq I Restriction Fragment Length Polymorphism of the Proband and His Parents

The proband is a 1.5-year-old Caucasian boy with tyrosinase-negative OCA. His parents, both Caucasians of Irish descent, are of normal phenotype but are heterozygotes with respect to tyrosinase activity as determined by the hair-bulb tyrosinase assay (22). Southern blot analysis of the genomic DNA of this family revealed Taq I polymorphic fragments of either 2.4 kb (father and child) or 2.8 kb (mother and child) and four nonpolymorphic fragments of 0.6, 0.9, 1.4, and 5.0 kb (all three).

FIG. 12 shows a southern blot analysis of Taq I-digested genomic DNA of a tyrosinase-negative albino proband and his parents. High molecular weight genomic DNA was digested with Taq I, electrophoresed in a 1% agarose gel, transferred to GeneScreenPlus membrane, and hybridized to 3$^{32}$P-labeled normal human tyrosinase cDNA Pme134. Lane 1. father; lane 2, mother: and lane 3, proband. Marker sizes are shown in kilobases (kb).

This polymorphism does not correlate with OCA, since unrelated normal individuals have the same frequency of polymorphism at these two alleles (unpublished data and Spritz, R., Strunk, K., Oetting, W. & King, R. (1989) Nucleic Acids Res. 16, 9890, incorporated herein by reference.). However, this analysis indicates that the tyrosinase gene of the proband is not associated with deletions or rearrangements detectable at this level.

RNA Blot Analysis

To determine whether tyrosinase was transcribed normally, Northern blots of poly(A)$^+$ RNA from the proband melanocytes were compared with those from normal melanocytes. FIG. 13 shows a northern blot analysis of poly(A)$^+$ RNA derived from cullures of melanocytic and nonmelanocytic cell lines. (A) Poly(A)+RNA samples from normal human melanocytes (lane 1), the proband's tyrosinase-negative albino melanocytes (lane 2), human amelanotic melanoma cells (lane 3), human melanotic melanoma cells (lane 4), Jurkat T cells (lane S), and MOLT-3 T cells (lane 6) were fractionated in a formaldehyde/1.4% agarose denaturing gel, blotted onto GeneScreenPlus membrane, and hybridited to $^{32}$P-labeled Pme134. (B) The same blot was stripped and hybridized to nick-transluated human γ-actin cDNA to show the amount of mRNA loaded in each lane. Tyrosinase mRNA was not detected in cells from nonmelanocytic origin (Jurkat and MOLT-3). The difference in the intensity of the tyrosinase bands in A is due to different amounts of poly(A)$^+$ RNA loaded onto the gel as evidenced by subsequent hybridization of the same blot to a γ-actin probe in B. There was no difference in size or abundance of the proband tyrosinase mRNA relative to the tyrosinase mRNA from normal melanocytes or melanoma cells, which suggests that at this level as well there were no major defects of transcription.

Isolation and Sequencing of Albino Tyrosinase cDNA Clones

The melanocytes of the proband were amelanotic but had residual tyrosinase activity, 5.7 microunits/mg of protein in comparison with 1673 microunits/mg in neonatal melanocytes pooled from normal donors, as measured in vitro by the method of Pomerantz. Since there was no decrease in the amount or size of the tyrosinase mRNA or major deletion in the tyrosinase gene, the possibility of a pathogenic point mutation was investigated. A cDNA library from the poly (A)$^+$ RNA of the cultured albino melanocytes in the λgt11 cloning vector was constructed. The cDNA library was screened with two oligonucleotide probes, representing the first and fourth exons of the tyrosinase gene to avoid isolating cDNAs of alternatively spliced RNA (Ruppert, S., Mueller, G., Kwon, B. S. & Schuetz, G. (1988) EMBO J. 7, 2715–2722, incorporated herein by reference.). From 300,000 plaques of recombinant phages screened, 8 independent clones hybridized to both probes. The cDNA inserts varied in size from 1.4 to 2 kb. Sequencing of five of these clones by a double-stranded-DNA sequencing method, using various oligonucleotide primers spanning different regions of the tyrosinase cDNA, showed that the clones were full-length. The albino nucleotide sequence was compared to that of Pme134 and to other cDNAs spanning the 5' and 3' portions of tyrosinase. FIG. 14 presents the sequence of Pme134A, the corrected version of tyrosinase cDNA Pme 134.

FIG. 14 shows the sequences shown in SEQ ID NO:7 and SEQ ID NO:8, specifically a nucleotide sequence of normal human tyrosinase cDNA (Pme134A), the deduced amino acid sequence, and the changes predicted on the basis of the identified point mutation in the albino proband as shown in shown in SEQ ID NO:9 and SEQ ID NO:10. Nucleotides are numbered from the first nucleotide of the ATG initiation codon. The deduced amino acids are shown below the nucleotide sequence and are numbered from the amino-terminal amino acid of mature tyrosinase. The amino acid residues of the putative signal peptide are indicated by negative numbers and are heavily underlined. The potential glycosylation sites are underlined in regular print. The putative transmembrane region is doubly underlined. The stop codons are indicated by three dashes. The nucleotide and deduced amino acid sequences downstream from the T insertional mutation (horizontal arrow) in the albino cDNA are shown in italics. The positions of five potentially harmless point mutations are shown by stars, and the nucleotide substitutions and consequent amino acid changes are indicated at right and are underlined.

The assignment of the signal sequence is based on tyrosinase protein sequence information (Wittbjer, A., Dahlback, B., Odh, G., Rosengren, A. M., Rosengten, E. & Rossman, H. (1989) Acra Derm. Venerol. 69, 125–131, incorporated herein by reference.). The mature tyrosinase is composed of 511 amino acids with seven potential glycosylation sites. The albino tyrosinase sequence differs from Pme134A by five nucleotide substitutions and one insertion. The substitutions were detected at Ruelestide positions 498, 575, 923, 1205, and 1484, counted from the A of the initiation codon ATG. These substitutions would result in amino acid changes indicated at positions 148, 174, 290, 384, and 477. They can be regarded as polymorphism. However, an insertion occurred at the putative transmembrane region, where a T residue was found between nucleotides 1467 and 1468 after codon 471. This mutation alters the reading frame and introduces a premature termination signal, TGA (nucleotide positions 1528–1530) after amino acid 490. This mutation would be expected to result in tyrosinase that differs from the normal enzyme in the 19 amino acids at its carboxyl terminus and that lacks 21 carboxyl-terminal amino acids.

FIG. 15 shows a portion of sequencing gel containing the T insertional mutation. The normal sequence represents Pme134A and the mutant sequence is that of the albino tyrosinase cDNA. The mutation site is indicated by arrows. The sequence is labeled 5' and 3' in reference to the orientation of the tyrosinase gene.

Immunoprecipitation of Tyrosinase with Anti-Tyrosinase Antibodies

The predicted structural alteration due to the T insertional mutation was corroborated by immunoprecipitation studies. The albino tyrosinase immunoprecipitated with antityrosinase antibodies (α-tyr) had faster electrophoretic mobility in polyacrylamide gels, with an estimated size 3 kDa smaller than the normal tyrosinase (FIG. 16 Left). Antibodies that recognize the carboxyl terminus of tyrosinase (α-PEP7) did not immunoprecipitate the albino tyrosinase (FIG. 16 Left). These results indicate that the tyrosinase of the proband has a major defect at the carboxyl terminus. The same results were obtained with tyrosinase immunoprecipitated from COS-1 cells transiently expressing normal or albino tyrosinase cDNA. Anti-tyrosinase antibodies immunoprecipitated tyrosinase from both normal and albino cDNA-transfected cells, with the albino tyrosinase again displaying faster mobility, and (α-PEP7 failed to immunoprecipitate the albino tyrosinase (FIG. 16 Right). Untransfected and pXM (vector)-transfected COS-1 cells did not produce immunoreactive tyrosinase (FIG. 16 Right, lanes $C^1$ and $C^2$, respectively).

DISCUSSION

The observations support the conclusion that the single base insertion in the putative transmembrane region of this albino tyrosinase produces a protein that is altered in its carboxyl terminus and renders the enzyme inactive. The eight isolated tyrosinase cDNA clones have the same T insertion, α-PEP7-immunoprecipitable tyrosinase could not be detected even after long fluorographic exposure (5 days, data not shown). If the proband were heterozygous for the T insertion, one should detect ~50% of the tyrosinase with the α-PEP7 antibodies. This result may indicate that both alleles of the proband harbor the same mutation. The other alternative is that one allele produces no mRNA or an unstable mRNA, since the parents were unrelated. No differences in the mRNA levels of the albino and normal controls were found. However, tyrosinase is an inducible enzyme (Kwon, B. S., Halaban. R., Kim, G. S., Usack, L., Pomerantz, S. & Haq, A. K. (1987) Mol. Biol. Med. 4, 339–355, incorporated herein by reference.), and the components of the medium, such as phorbol ester, alter the level of tyrosinase. Therefore, the level of expression of tyrosinase in the cultured melanocytes does not necessarily reflect the situation in vivo.

The mutation observed is different from the mutation reported by Tomita et at., where a single base C insertion in exon 2 of an OCA individual caused a shift of the reading frame and introduced a premature termination signal after amino acid 298. In that case, it was not demonstrated that the albino melanocytes produced the predicted truncated tyrosinase. Another tyrosinase gene mutation was reported by Giebel et at. in 6 out of 30 unrelated tyrosinase-negative albinos, where a change from C to T (CCT→CTT) at codon 81 (codon 63 of the Pme134A sequence, FIG. 3) would result in a substitution of leucine for proline. This Pro→Leu mutation is not at any of the putative functional domains such as the transmembrane, copper binding, or elycosylation sequences. Nevertheless, the proline and the five amino acids preceding it are conserved in both tyrosinase and the melanocyte-specific b-locus protein catalase B (Halaban, R. & Moellmann, G. (1990) Proc. Natl. Acad. Sci. USA 87, 4809–4813, incorporated herein by reference.), which indicates an important function for this domain. Spritz et al. also reported two missense substitutions in an albino: one in one of the two putative copper binding sites and the other in a potential slycosylation site. Whether these mutations can be held responsible for the inactivity of the enzyme(s) remains to be validated at the protein level.

The nucleotide substitutions detected at positions 498, 575, 923, 1205, and 1484 in albino tyrosinase cDNA putatively alter the amino acids at positions 148, 174, 290, 384, and 477. Four of these substitutions are also seen in other normal tyrosinase sequences (unpublished data and Shibahara, S., Tomita, Y., Tagami, H., Mueller, R. M. & Cohen, T. (1988) Tohoku J. Exp. Med. 156, 403–414; Bouchard, B., Fuller, B. B., Vijayasaradhi, S. & Houghton, A. N. (1989) J. Exp. Med. 169, 2029–2042, each incorporated herein by reference). The fifth, a Met→Ile change at position 148, was not reported before; but because of the conservative nature of the substitution, it may represent another site of polymorphism.

The mutation observed in the proband in the putative transmembrane domain would cause, in addition to truncation, a reduction in hydrophobicity due to the introduction of arginine and glutamic residues and, therefore, would interfere with the insertion of the protein into the melanosomal membrane. Several peroxisomal enzymes have been shown to have a targeting signal at the carboxyl terminus. Melanosomes are considered by some investigators to be modified peroxisomes. Tyrosinase shares the carboxyl-terminal Ser-His-Leu peroxisomal targeting sequence with some peroxisomal enzymes (Gould, J. J., Keller, G. A. & Subramani, S. (1988) J. Cell Biol. 107, 897–905, incorporated herein by reference.). Therefore, if tyrosinase uses the carboxyl-terminal Ser-His-Leu as the melanosomal targeting signal, the truncation would abolish the signal.

The results show several kinds of mutations that can produce tyrosinase-negative OCA. The heterogeneity of mutations at the TYR locus make efficient prenatal diagnosis and carder detection dependent on the availability of a panel of probes.

A cis-acting element involved in mouse tyrosinase gene expression

MATERIALS AND METHODS

Cell culture and nuclear extract

B16 melanoma cells were grown in DMEM supplemented with 10% fetal calf serum. Nuclear extract was prepared essentially following the method of Dignam et al (Dignam, J. D., Lebovitz, R. M., and R. G. Roeder (1983) Accurate transcription initiation by RNA polymerase II in a soluble extract from isolated mammalian nuclei. Nucleic. Acids. Res., 11:1475–1489 incorporated herein by reference) using HEPES buffer. Usually, 4 to 6 mg/ml protein was obtained from $10^8$ cells.

Promoter fragment

A 0.42 kb HindIII—XmnI fragment of mouse tyrosinase (−80 to −509 bp relative to the transcription start site) was isolated from a 2.2 kb HindIII fragment and subcloned in SmaI—HindIII sites of pGEM7 vector (Promega; Madison, Wis.). This fragment was isolated, end labeled selectively at the HindIII end and used for DNase I protection assays.

Gel Shift assay

Gel shift assay was performed based on the method of Carthew et al (Carthew, R. W., Chodosh, L. A., and P. A. Sharp (1985) An RNA polymerase II transcription factor binds to an upstream element in the adenovirus major late promoter. Cell., 43:439–448 incorporated herein by reference). DNA binding reactions were performed in a volume of 25 µl with 1 µg of poly dI-dC, 2 µg BSA and 12% glycerol in HEPES buffer (pH 7.9). Two µg of nuclear extract or 0.2 µg of affinity purified fraction was pre-incubated for 10 minutes at 30° C. and 10,000 cpm of end labeled probe was added to the mixture. The binding reaction was allowed to proceed for 30 minutes at 30° C. and the bound complex separated from unbound probe on 5% low ionic strength polyacrylamide gels with recirculating TAE buffer.

DNase I protection analysis

The 0.42 kb promoter fragment of mouse tyrosinase was excised from the vector and labeled with [α-$^{32}$P]-dATP at one end (HindIII end) with klenow fragment of E. coli polymerase I. The labeled probe was ethanol precipitated and further purified by DEAE membrane (Schleicher & Schuell) on agarose gel. For each footprint reaction, 50,000 cpm (<1ng DNA) of end labeled probe was used. Binding reactions were carried out in HEPES buffer, pH 7.9 (Emerson, B. M., Lewis, C. D., and G. Felsenfeld (1985) Interaction of specific nuclear factors with the nuclease-hypersensitive region of the chicken adult β-globin gene. Cell., 41:21–30 incorporated herein by reference), along with 1 µg of poly dI-dC and 1 µg of BSA. 8 to 10 µg of crude nuclear extract or 0.2 µg of desalted affinity purified fraction was added and the mixture pre-incubated for 10 minutes at 30° C. before adding probe. Following the addition of probe, the reaction was allowed to proceed for 30 minutes at 300° C. prior to DNase I treatment. DNase I (BRL, Gaithersburg, Md.) was added to a final concentration of 0.05 µg/ml and the incubation was further continued for 2 minutes at 30° C. before adding DNase stop solution containing ammonium acetate in ethanol. The DNA was ethanol precipitated and purified by phenol extraction. Following another round of ethanol precipitation, DNA was dissolved in formamide loading buffer, heat denatured and separated on 8% urea-polyacrylamide sequencing gels. Control reactions with no nuclear extract and Maxam-Gilbert sequence ladders of the same probe were prepared and subjected to gel electrophoresis adjacent to footprint reactions to localize binding-site sequences. The gels were dried and exposed at −70° C. with intensifying screen.

Oligomers

Two 27 bp complementary oligomers with sequences a) SEQ ID NO:2 5'AGCTTGATGTATTCTTGATACTACTTA 3' and b) SEQ ID NO:3 5'AGCTTAAGTAGTATCAA-GAATACATCA 3' were synthesized. HindIII restriction sequences were added at both ends to facilitate cloning. The oligomers were annealed, kinased, and ligated to form multimers. The catenated oligomers were gel purified, and the tetramer sequence was subcloned at HindIII site of pBluescript II KS vector (Stratagene; La Jolla, Calif.).

Affinity purification

Biotin-cellulose affinity purification was carried out following the method of Kadonaga (Kadonaga, J. T., and R. Tijan (1986) Affinity purification of sequence-specific DNA binding proteins. Proc. Natl. Acad. Sci. USA., 83:5889–5893 incorporated herein by reference. The tetramer probe was excised from the pBluescript vector at ClaI and EcoRI sites and end labeled by klenow. Thymidine nucleotides were substituted by biotin-UTP and [α-$^{32}$P]-dATP was used to monitor the binding stability of probe to cellulose. 1.5 mg of crude nuclear extract from B16 melanoma was incubated in HEPES buffer with 10% glycerol, 0.1 mg/ml calf thymus DNA and 0.1 mg/ml BSA at 30° C. for 10 minutes prior to the addition of the probe. 0.5 µg of biotin labeled tetramer probe was then added to the mixture and binding reaction continued for 30 minutes. Following binding, 50 µg of streptavidin was added and incubated for 5 more minutes. Biotin-cellulose, pretreated with calf thymus DNA and BSA, was added and allowed to couple with streptavidin-biotin-protein complex at 4° C. for 90 minutes with gentle agitation. After this binding, the mixture was spun briefly in microcentrifuge and unbound protein removed from cellulose. The resin with probe and protein complex was washed five times with biotin-cellulose binding buffer (12 mM HEPES, pH 7.9, 4 mM Tris-Cl, 60 mM KCl, 1 mM EDTA, 1 mM DTT and 12% glycerol) to remove unbound protein and the bound protein was later eluted in 50 µl elution buffer (20 mM Tris-Cl, pH6.8, 1M KCl, 5mM MgCl$_2$%, 1 mM EDTA, 1 mM DTT, 200 µg/ml BSA and 12% glycerol). The eluents were tested on 10% SDS-denaturing PAGE.

UV-cross linking

The DNA binding reaction was essentially the same as one described in gel shift assay. Following binding reactions, the bound complex was cross-linked under UV irradiation for 5 minutes at 254 nm. The complex was later denatured and resolved on 8% SDS-polyacrylamide gel (Chodosh, L. A., Carthew, R. W., and P. A. Sharp (1986) A single polypeptide possesses the binding and transcription activities of the adenovirus major late transcription factor. Mol. Cell. Biol., 6:4723-4733 incorporated herein by reference).

Transfection and CAT assay

The double stranded oligomer was ligated upstream of the CAT reporter gene in a plasmid vector, pCAT™-promoter plasmid (Progema, Wis.), containing the CAT gene with the SV-40 promoter. Twenty micrograms of CsCl purified DNA was electroporated into B16 mouse melanoma and HeLa cells. Electroporation was performed at 390V and 980 µF. Control experiments with no plasmid DNA and with promoter plasmid lacking oligomer insert were performed simultaneously. One microgram of reference plasmid with β-galactosidase (β-gal) gene was also co-transfected as an internal control. The cells were harvested 60 hrs after transfection and activities of CAT and β-gal determined as described (Maniatis, T., Fritsch, E. F., and J. Sambrook (1989) Molecular Cloning—A Laboratory Manual. Second Edition, Cold Spring Harbor Laboratory, Cold Spring Harbor, N.Y. incorporated herein by reference).

RESULTS

A 2.2 kb HindIII fragment of the mouse tyrosinase gene promoter was digested sequentially with XmnI, SfaNI, NcoI and DdeI to generate six smaller fragments. The sizes of the fragments were 140 bp, 580 bp, 270 bp, 271 bp, 326 bp and 426 bp from 5' to 3' direction.

FIG. 17 shows a promoter region of the mouse tyrosinase gene. The restriction sites indicate those used for generating smaller fragments with their lengths in base pairs. The location of cis-acting elements and purine rich domain are shown above.

Each fragment was end labeled and tested for protein binding with nuclear extracts from B16 melanoma cells. Of the six fragments, protein binding was observed with 580 bp and 426 bp fragments. The 426 bp fragment lies immediately upstream to the initiation codon and contains the CCAAT sequences. The 580 bp lies near the 5' end of the 2.2 kb fragment. The 426 bp fragment was chosen for further analysis because this fragment is adjacent to the transcription start site. DNase I protection assay was performed to test whether the proximal 0.42 kb fragment interacts with crude nuclear extracts from B16 melanoma cells. The footprinting revealed that the nuclear extract protected a ten base pair region situated -236 bp upstream to the RNA start site in addition to the CCAAT box sequence. There was no protection to this area by a non-pigment cell nuclear extract (EL-4). The sequence of the protected region was TGATG-TATTC and is referred to as tyrosinase element-1 (TE-1) shown in SEQ ID NO:1. With different batches of B16 melanoma nuclear extracts, the protected area extended downstream. The entire sequence protected was TGATG-TATTCTTGATACTACT shown in SEQ ID NO:12.

FIG. 18 shows a DNase I footprinting of the 0.4 kb mouse tyrosinase promoter. Lane 1 indicates control pattern of DNase I cleavage with no protein. Lane 2 indicates DNase I protection pattern of B16 melanoma nuclear extract at TE-1 sequence and CCAAT region.

To determine the nature of the protein that binds to this region, the TE-1 binding protein (TEBP-1) was purified with a 27 bp double stranded oligomer. The oligomer was catenated and the tetramer probe was labeled with biotinylated TTP by Klenow fragment of E. coli polymerase I. The end labeled probe was incubated with crude B16 melanoma nuclear extract in microfuge tubes. Following binding and washing of the unbound protein, the bound material was separated from the probe using elution buffer containing 1M KCl. The affinity purified fraction was later desalted through Sephadex G25 column.

To determine whether the affinity purified proteins bound to the TE-1 element, both gel shift and footprint assays were performed. The gel shift assay was performed by incubating the affinity purified fraction with end labeled double stranded oligomer corresponding to the TE-1 sequence at 30° C. for 30 minutes and the binding complex resolved on 5% low ionic strength polyacrylamide gel. The results of gel shift assay indicated a single strong binding complex.

FIG. 19 shows a gel shift assay with affinity purified fraction. 0.2 µg of affinity purified fraction of B16 melanoma nuclear extract using TE-1 sequence was incubated with end labelled TE-1 oligomer and the bound complex resolved on 5% polyacrylamide gels. Lane 1 indicates free probe (F.P) with no protein and Lane 2 indicates binding complex (B) with affinity fraction.

In order to determine the size of the TEBP-1, the affinity-purified proteins were fractionated using Sephacryl-400 column. The eluent containing 49 kD fraction contained TEBP-1 when the column eluents were tested individually for binding on gel shift assay with the TE-1 oligomer.

To confirm the sequence-specific binding of the affinity purified fraction on the 0.42 kb promoter fragment of mouse tyrosinase, a footprint assay was performed. The 0.42 kb promoter fragment was end labeled and incubated with 0.2 µg of desalted affinity-purified proteins under conditions described in Materials and Methods for 30 minutes at 30° C. Following DNase I treatment, the products were resolved on sequencing gel. The footprint assay showed that the affinity fraction protected specifically the TE-1 element in the promoter fragment.

FIG. 20 shows a DNase I footprinting of the 0.4 kb mouse tyrosinase promoter with affinity fraction. 0.2 µg of desalted affinity purified fraction was used in binding reaction followed by DNase I cleavage. Specific protection to TE-1 sequence, indicated in bracket, was observed when affinity fraction was used for binding (Lane 2). Lane 3 shows footprinting with 8 µg of crude nuclear extract of B16 melanoma and Lane 1 indicates control pattern of DNase I digestion of the probe with no protein.

Further, to determine the molecular weight of the TEBP-1, UV-cross linking experiments were performed with the TE-1 probe. The labeled-TE-1 probe was incubated with 0.2 µg of affinity-purified protein or 2 µg of crude nuclear extract of B16 melanoma cells at 30° C. for 30 minutes. Following binding, the DNA-protein complex was covalently cross linked by UV-illumination at 254 nm for 10 minutes. The bound complex was later denatured and run on 10% SDS-PAGE. The UV-cross linking indicated that a protein fraction of approximately 49 kD bound to the TE-1. Similarly, identical binding of a fraction with the same molecular size was also observed with the B16 melanoma nuclear extract, confirming that the TEBP-1 in affinity fraction is the same as the one from the crude nuclear extract. When the TE-1 oligomer was tested for binding with affinity fraction purified using a non-specific sequence, there was no binding following UV-cross linking.

FIG. 21 shows a UV-cross linking of TE-1 oligomer. Both the affinity purified fraction of B16 melanoma nuclear extract with TE-1 sequence and the crude nuclear extract of B16 melanoma exhibit a 49 kD protein binding to TE-1 oligomer as in Lanes 1 and 3 respectively. Affinity purified fraction of B16 melanoma nuclear extract using a non-specific oligomer sequence has not indicated any binding as shown in Lane 2.

Following these observations, the enhancer property of the TE-1 sequence was tested by transient expression system in B16 melanoma and HeLa cells. For this, the oligomer containing TE-1 sequence was ligated upstream to SV-40 promoter sequence of a Promoter CAT plasmid and transfected to B16 melanoma and HeLa cells. Similar transfections were also done with plasmid bearing SV-40 promoter alone without the TE-1 oligomer. The results of CAT assay indicated a three-fold increase in CAT activity in plasmid constructs with the TE-1 sequence only in B-16 melanoma cells and not in HeLa cells.

FIG. 22 shows a CAT assay performed with TE-1 sequence in B16 melanoma cells. The double stranded TE-1 oligomer was fused upstream to SV-40 promoter region of a promoter CAT vector and transfected to B16 melanoma cells. The CAT activity indicated a three-fold increase of the reporter gene expression with the construct having TE-1 oligomer (Lane 2) compared to the native plasmid (Lane 3). Lane 1 denotes mock transfection with no plasmid.

FIG. 23 shows a CAT assay performed with TE-1 sequence in HeLa cells. There was no increase in CAT activity of promoter plasmid construct with TE-1 oligomer (Lane 2) compared to the native plasmid lacking TE-1 sequence (Lane 3) in HeLa cells. Lane 1 indicates mock transfection with no plasmid.

DISCUSSION

The tissue specific expression of tyrosinase gene favors the presence of a putative cis-acting element and trans-acting factor regulating its transcription. Sequence analysis of the promoter of mouse tyrosinase gene reveals the presence of cis-acting elements such as AP-1, AP-2, glucocorticoid responsive element and UV-responsive element upstream to the CAT and TATA boxes. These transcriptional control elements were also revealed in the human tyrosinase gene promoter. Apart from these ubiquitous elements, an unique homology of about 120 bases containing a purine rich sequence consisting of AG repeat has also been found in both the mouse tyrosinase gene promoter between −662 and −542 bases upstream and in the human tyrosinase gene promoter between −780 and −657 bases upstream. The localization of these sequences in mouse tyrosinase promoter is indicated in FIG. 17.

In order to identify a potential cis-acting element of the mouse tyrosinase gene, portions of 2.2 kb promoter region were analysed upstream of the transcription start site by gel shift assay. Smaller fragments of the promoter region were generated using restriction sites and binding experiments were performed with nuclear extracts of B16 mouse melanoma cells. The restriction sites and fragments used are also depicted in FIG. 17. The gel shift assay indicated binding of the B16 nuclear extract to two of the fragments; a 580 bp fragment situated −1370 bases upstream and a 426 bp fragment situated −80 bases upstream of transcription initiation site. Sequence analysis of both the fragments indicated the presence of TATA and CCAAT like sequences. A 326 base pair fragment which includes the 120 base long purine rich domain did not show any specific binding on gel shift indicating that it may be represented in both mouse and human tyrosinase promoters only as a conserved region without any functional significance.

With this initial observation, footprint analysis of the 426 bp promoter fragment was performed using B16 melanoma nuclear extract. The results of this investigations indicate a potential cis-acting element, TE-1, of the mouse tyrosinase gene located −236 base pairs upstream from the transcription initiation site. Nuclear extract from a non-pigment cell line however did not protect this region indicating a probable tissue specificity. The location of this sequence in mouse tyrosinase promoter also confirms the earlier report of Kluppel et al (1991) that the region −270 bp upstream is enough for the tissue specific expression of this gene in transgenic mice. A recent report on a mouse tyrosinase-related protein-1 gene promoter indicated an eleven base pair sequence sharing homology with mouse and human tyrosinase promoters (Jackson, I. J., Chambers, D. M., Budd, P. S., and R. Johnson (1991) The tyrosinase-related protein-1 gene has a structure and promoter sequence very different from tyrosinase. Nucleic. Acids. Res., 14:3799–3804 incorporated herein by reference. However, DNA binding with nuclear extract of B16 melanoma to this region was not observed. The DNase I footprint data indicated a 10 bp region situated −236 bp upstream of the initiation codon showing consistent protection apart from the CCAAT box region. The sequence of the protected region is 5'-TGATGTATTC-3' shown in SEQ ID NO:1. With different batches of nuclear extracts of B16 melanoma cells, the protected region extended further downstream by 21 bases. This domain lies upstream of the CCAAT, and TATA boxes of mouse tyrosinase promoter.

Further, the potential trans-acting factor was characterized by biotin-cellulose affinity purification method. The affinity fraction that was separated from the rest of the unbound protein from B16 melanoma nuclear extract showed strong binding ability with the TE-1 oligomer. The affinity material was size fractionated and the fraction containing 49 kD protein bound to TE-1. UV-cross linking studies also demonstrated that TEBP-1 is a 49 kD protein. Comparison of the affinity purified fraction along with the nuclear extract of B16 melanoma cell on UV-cross linking also confirmed that the protein species that bound to TE-1 was one and the same. However, the affinity of binding was found to be stronger in the crude nuclear extract than the affinity purified materia.

This could probably be either due to the requirement of other nuclear protein for efficient binding or the affinity purification steps could have reduced the binding affinity of TEBP-1. When a non-specific oligomer was used to test the binding ability of the affinity purified fraction by UV-cross linking, there was no binding indicating the sequence specificity of TEBP-1. Further, the affinity purified fraction also exhibited specific protection to TE-1 sequence on footprint assay with the promoter fragment much as the crude nuclear extract. These observations suggest that a probable factor of 49 kD molecular weight might be involved in the regulation of the tissue specific expression of mouse tyrosinase gene.

CAT assay was used to attempt to demonstrate if the sequence observed has a significant role in enhancing transcriptional rate. For this the double stranded oligomer was fused upstream to the SV-40 promoter region of pCAT™-promoter vector. The native vector lacks any enhancer region and allows to monitor the enhancer properties of DNA sequences when fused upstream to the SV-40 promoter. The results on transfection assay also showed a three-fold increase in CAT activity based on quantitation of the acetylated chloramphenicol only in plasmid constructs with the oligomer fused upstream of the CAT gene only in B16 melanoma cells and not in HeLa cells. The experiments collectively suggest that a probable cis-acting element located −236 bp upstream of the transcription initiation site could play an important role in tyrosinase gene expression. Sequence Analysis and Characterization of the Human Tyrosinase Gene Promoter

MATERIALS AND METHODS

Cell culture

Human melanoma cell line, Stilling (YUSIT 1), was cultured in F10 medium (Gibco Laboratories, Grand Island; N.Y.) supplemented with 10% fetal calf serum and 50 U/ml of penicillin and streptomycin and Genovese cells were grown in RPMI (Gibco) medium with 10% fetal calf serum and antibiotics, as above. HeLa cells were cultured in DMEM with 10% new-born calf serum and antibiotics as above.

Restriction mapping

A recombinant cosmid clone (Cos 28A), containing a portion of the human tyrosinase gene in cosmid pJB8 was isolated by screening human genomic library with human tyrosinase cDNA probe, Pmel 34 (Kwon et al, 1987). DNA of this clone was digested with restriction enzymes BamHI, BglII, EcoRI, EcoRV, HindIII, PstI, SalI and XbaI in both single and double digestions overnight. The digested products were separated on 0.5% agarose gels and transferred to Gene Screen plus. Eighteen base long synthetic oligonucleotide probes representing regions of exon 1, exon 2 and exon 3 sequences of human tyrosinase gene and twelve base long cos-arm probe of the vector were end labeled by polynucleotide kinase (NEB) and used to hybridize the filters. Hybridizations were carried out overnight at 42° C. in solution containing 6× SSC, 5× Denhardt reagent, 0.5% SDS, 100 µg/ml denatured fragmented salmon sperm DNA and $1\times10^6$ cpm probe/ml solution. The filters were washed in solution containing 0.1× SSC and 0.5% SDS two degrees below the hybridization temperature and exposed. The relative mobilities of the hybridized bands were determined and a partial restriction map of the recombinant cosmid clone constructed.

Promoter sequencing

A 6 Kb BglII fragment containing the 5' flanking region and the first exon was subcloned in pGEM3 (Promega, Madison, Wis.). The 6 Kb fragment also contained two EcoRI sites which were exploited for generating fragments of smaller length. Each smaller EcoRI fragment was subcloned in pGEM 7 vector (Promega, Madison, Wis.). Nucleotide sequence of the 2.2 Kb 5' flanking region from the ATG codon was determined by dideoxy chain termination sequencing using sequenase (United States Biochemicals Corporation, Ohio). T7 and SP6 primers of polymerase initiation region of the vector and two other synthetic oligonucleotide primers, each of 16 bp lengths, corresponding to the antisense strand of human tyrosinase gene at different lengths of the promoter region were used for sequencing. The sequences of the primers used were 1) SEQ ID NO:13 5' GCTGTAGCCATATTGT 3' and 2) SEQ ID NO:14 5'TGGTGGGCTGATATTA 3', located at −963 and −1254 bases respectively upstream of the ATG codon of human tyrosinase gene.

Sequence analysis

Computer analysis of the 2.2 Kb 5' flanking sequence of the promoter was performed using Pustell sequence analysis program (IBI, New Haven, Conn.) for homology search with reported sequences of different cis-acting elements of transcription regulation. The human tyrosinase sequence was also compared with 5' flanking sequences of mouse promoter using sequence match program.

Primer extension analysis

2 µg of poly(A)⁺ RNA from Genovese melanoma cells were annealed with $5\times10^5$ cpm kinased oligonucleotide primer at 20° C. overnight in a buffer containing 0.4M NaCl, 40 mM Pipes (pH 7.0), 1 mM EDTA (pH 8.0) and 80% formamide. The primer was a 17 mer corresponding to the antisense strand of human tyrosinase with sequence 5'GAAAT-GGCCAGGGGAGG 3' located 44 bp downstream of ATG codon and shown in SEQ ID NO:15. The mixture was precipitated with ethanol and suspended in reaction buffer containing 50 mM Tris-Cl (pH 7.6), 60 mM KCl, 10 mM $MgCl_2$, 1 mM DTT, 1 mM each dATP, dCTP, dGTT and dTTP, 1000 U/ml RNAsin (Promega Biotech) and 50 U AMV reverse transcriptase (BRL). Extension reaction was performed at 37° C. for 2 hrs followed by the addition of 50 µg/ml RNase and incubation continued for another 30 minutes. The DNA was extracted with phenol chloroform and precipitated with ethanol. The precipitate was dissolved in formamide buffer, heat denatured and analysed on sequencing gel.

Construction of promoter plasmids

From the 6 Kb BglII fragment containing the promoter region and exon 1, a 2.02 Kb portion was excised using XmnI and PstI enzymes. The XmnI site lies at 5' end of the 2.02 Kb fragment and PstI site, at 13 bases downstream of the major transcription start site. This 2.02 Kb fragment was initially subcloned in pBluescript II KS vector and isolated from pBluescript using SalI and XbaI sites to facilitate direct cloning at SalI-XbaI sites of CAT vector. This fragment was subcloned in SalI-XbaI (5' and 3' direction respectively) sites upstream to the CAT gene of a pCAT-Basic vector (Promega, Madison, Wis.) to yield pHTY-CAT plasmid.

Deletion mutants

Deletion mutants from the 5' end of the 2.02 Kb tyrosinase promoter of pHTY-CAT plasmid were generated by treatment with exonuclease III using Erase-a-base system (Promega). 10 µg of the plasmid DNA was first cut with SphI that generates a 3'-overhang followed by digestion with SalI which generates a 5'-overhang and which can lead to the exonuclease III digestion towards the 3'sequences of promoter region. Following the double digestion, the linear plasmid was purified by phenol extraction and dissolved in 50 µg exonuclease III buffer (66 mM Tris-Cl, pH 8.0 and 0.66 mM $MgCl_2$) and incubated at 30° C. prior to the addition of exonuclease III enzyme. 250 units of exonuclease III was added to the DNA, mixed quickly, placed in 30° C. and aliquots were removed at regular intervals of 60 seconds. The aliquots were mixed with 20 µl of S1 mix containing S1 buffer (30 mM potassium acetate pH 4.6, 0.25M NaCl, 1 mM $ZnSO_4$ and 5% glycerol) and 300 U/ml S1 nuclease on ice. The samples were then incubated for 30 minutes at room temperature followed by the addition of 1 µl of S1 stop buffer (0.3M Tris and 0.05M EDTA) and heating at 70° C. for 10 minutes to inactivate S1. The samples were transferred to 37° C. and 1 µl of Klenow mix (20 mM Tris-Cl, pH 8.0, 100 mM $MgCl_2$ and 0.1 U/ml Klenow polymerase) was added and incubated for 15 minutes. The products were separated on 1% agarose gel and the DNAs isolated using Geneclean (LaJolla, Calif.). The samples were ligated overnight at 15° C., transformed to *E. coli* and grown on ampicillin plates. Clones containing suitable deletions were identified by performing restriction enzyme digestion on plasmid DNA prepared from 5 ml cultures and the exact length of deletion determined later by dideoxy sequencing of each clone using a pCAT plasmid primer.

Transfection and enzyme assays pHTY-CAT plasmids were transfected into HeLa cells by DEAE-dextran method (Lopata, M. A., Cleveland, D. W. and Sollner-Webb, B. (1984). High level transient expression of a chloramphenicol acetyl transferase gene by DEAE-dextran mediated DNA transfection coupled with a dimethyl sulfoxide or glycerol shock treatment. *Nucleic. Acids. Res.* 12, 5707–5717 incorporated herein by reference) and into melanoma cells by electroporation (Neumann, E., Schaefer-Ridder, M., Wang, Y. and Hofschneider, P. H. (1982). Gene transfer into mouse lyoma cells by electroporation in high electric fields. *EMBO J.* 1, 841–845 incorporated herein by reference). For DEAE dextran transfection, cells were grown to a density of $0.5 \times 10^6$ cells/100 mm culture dish. Prior to the addition of DNA in DEAE-dextran, cells were washed in DMEM medium without serum followed by the addition of 4 ml DMEM with 10% fetal calf serum. 20 µg of cesium chloride purified pHTY-CAT plasmid DNA and 2 µg of CMV-β-galactosidase (β-gal) internal control plasmid were made in 40 µl TBS (25 mM Tris, 135 mM NaCl and 2.5 mM KCl) and mixed with 80 µl sterile 10 mg/ml DEAE-dextran solution (Pharmacia). The DNA in DEAE solution was slowly spread on HeLa cells in DMEM, swirled gently and incubated for 4 hrs at 37° C. After 4 hrs of incubation, the medium with DEAE dextran was removed from the dishes and DMSO (10% in PBS) shock was given for 1 min. The DMSO was removed immediately with excess PBS. The cells were then subjected to chloroquine (0.1 mM in DMEM) treatment for 90 minutes and later grown in fresh DMEM with fetal calf serum at 37° C. for 60 hrs before harvesting.

For transfection by electroporation, cells were harvested from culture dishes and resuspended in F10 medium at a concentration of $2 \times 10^6$ cells/ml. For each transfection $1 \times 10^6$ cells were aliquoted to individual cuvettes, 20 µg of pHTY-CAT plasmid and 2 µg of β-gal internal control plasmid were added and chilled on ice for 10 min. Electroporation was carried out at 380 volts and 980 µF capacitance using a Hoefer Scientific, Progenitor II pulsar. Cells were then incubated on ice for 10 minutes, transferred to culture dishes with 10 ml of medium and grown at 37° C. for 60 hrs prior to harvesting.

Cells were harvested by scrapping and washed two times with PBS. The cell pellet was suspended in 100 µl 0.25M Tris,pH 8.0, and lysed by three cycles of freeze-thawing. Cell extracts were collected after centrifugation at 12,000 rpm for 10 min at 4° C. Activities of β-gal and CAT were determined following standard methods (Maniatis et al., 1989). Volumes of cell extract used for CAT assay were normalized based on β-gal activities in each sample.

RESULTS

Restriction mapping

The recombinant cosmid clone, Cos 28A, was found to contain a ~40 Kb insert of a portion of human tyrosinase gene. The portion of the human tyrosinase gene included 7 Kb of the 5' flanking sequence, first and second exons, entire first intron and a 10 Kb portion of the second intron.

FIG. 24 shows a partial restriction map of cosmid clone (Cos 28A) with a ~40 Kb portion of human tyrosinase gene.

The DNA was digested with restriction enzymes indicated in the map and hybridized with oligomer probes representing exons 1, 2 and 3. The relative distance between the enzyme sites and intron exon junctions are as determined by the relative mobilities of fragments.

Hybridization of the filters with oligomer for exon 3 did not produce any signal indicating that the recombinant clone does not include the third exon. The approximate positions of the restriction sites of Cos 28A were determined and the length of the first intron was identified to be approximately 22 Kb. The second intron has also been ascertained to extend beyond 10 Kb in length. Based on the restriction mapping information, a 6 Kb BglII fragment was isolated that contained a 5 Kb promoter region, entire exon 1 and ~0.2 Kb intron 1.

Identification of transcription start site

To determine the transcription initiation site, a 17 base long synthetic oligomer complementary to the non-coding strand was end-labelled, hybridized with poly(A)$^+$ RNA isolated from Genovese cells and extended with reverse transcriptase. The extension product was analyzed on a sequencing gel and the precise size of the transcripts determined by comparing to a corresponding genomic DNA sequence ladder generated alongside with the same primer that was used for primer extension. The results of the primer extension analysis indicated a major transcriptional start site situated 42 bases upstream to the ATG codon and three minor transcriptional mRNA sites at 34, 78 and 79 bases upstream of ATG. Three of the four transcription sites started at A preceded by C.

FIG. 25 shows a primer extension analysis to determine the human tyrosinase gene transcriptional initiation site. A 17 base end-labelled oligomer primer, complementary to the coding strand of human tyrosinase gene, 44 bases downstream of ATG, was hybridized with poly(A)$^+$ RNA isolated from Genovese cells and extended using reverse transcriptase. Non-coding strand of the sequencing ladder obtained by extending with the same primer using genomic DNA template is used to locate the precise position of transcriptional start sites.

5' Flanking sequence analysis

To characterize the promoter region of the human tyrosinase gene, a 2.2 Kb DNA sequence of the 5' flanking region was determined. FIG. 26 shows a nucleotide sequence of the human tyrosinase gene promoter as determined by dideoxy sequencing shown in SEQ ID NO:11. The consensus cis-acting elements are indicated in bold and * denotes transcription start sites as observed by primer extension analysis. ATG codon is indicated by double underline.

Sequence analysis of the promoter indicated the presence of initiator and enhancer sequences. A TATA box was identified at −27 bp upstream to transcription start site. A CAAT box was found at −128 bp upstream to the transcription start site. In addition to these, there were also five canonical AP-1, two AP-2, two glucocorticoid responsive elements (GRE), three Oct-1 and two UV-responsive elements found at different regions of the human tyrosinase promoter. Apart from these transcription regulatory elements, there was also a unique 230 base long purine rich domain present at −634 bases upstream to transcription start site.

Functional analysis of tyrosinase promoter

Earlier experiments in mouse tyrosinase gene promoter indicated that a 2.1 Kb portion of the promoter was sufficient for producing pigmentation in transgenic mice (Yokoyama et al., 1990). With this observation the promoter function of a 2.02 Kb 5' flanking region of human tyrosinase gene was studied. To determine the promoter region that controls human tyrosinase gene expression, a series of 5' deletion mutants of the 2.02 Kb promoter was generated. The deleted constructs fused upstream to CAT gene of a reporter plasmid were transfected onto melanoma cells for transient expression analysis.

Results of CAT assays in human melanoma cells indicated highest activity in pHTY-CAT plasmid construct containing the entire −2020 bp region of the human tyrosinase promoter. All other CAT activities are expressed as percentage of this value. Plasmid constructs with −1739 bp and −1153 bp promoter sequences showed 43 and 59% CAT activity while the construct with −550 bp and −438 bp had relative CAT activities of 91 and 76% respectively. The plasmid construct with −258 bp had 48% CAT activity and one with −83 bp promoter indicated 20% activity. The native plasmid pCAT-Basic when transiently transfected into melanoma cells resulted in CAT activity of 4% and positive control plasmid with SV40 promoter and enhancer sequences upstream yielded 169% CAT activity relative to the construct with −2020 bp human tyrosinase promoter.

FIG. 27 show a CAT assay of pHTY-CAT reporter gene deletion series in human melanoma cell line. 20 μg of pHTY-CAT plasmids were co-transfected with 2 μg of CMV-β gal DNA on to Stilling cells by electroporation. The cells were cultured for 60 hrs, harvested and cell extracts used for CAT assay. The numbers on each pHTY-CAT plasmid lane denotes the size of the human tyrosinase promoter in kilobase pairs linked to the CAT gene. Transfection with control plasmids pHTY-Promoter and Enhancer (P+E), pHTY-Promoter (P) and pHTY-Basic (B) are indicated in the first three lanes.

DISCUSSION

Partial restriction mapping studies on Cos 28A indicate the widely spaced genomic organizations of exons 1, 2 and 3 of human tyrosinase gene. Primer extension analysis indicated a major transcription start site at 42 bases upstream of the ATG codon. Apart from this, there were also three minor transcription initiation sites at regions 34, 78 and 79 bases upstream from the ATG codon. This observation differs from the earlier reports of Takeda et at. (Takeda, A., Tomita, Y., Okinaga, S., Tagami, H. and Shibahara, S. (1989). Functional analysis of the cDNA encoding human tyrosinase precursor. *Biochem. Biophys. Res. Commun.* 162, 984–990 incorporated herein by reference) and Giebel et al., (1991). Neither of these investigators observed three minor transcription sites and positioning of the start site in their experiments were not ascertained using genomic DNA sequences along with the primer extension products. The transcription initiation sites of this investigation started with an A preceded by C at position −1 as is commonly observed in other eukaryotic genes (Bucher, P. and Trifonov, E. N. (1986). Compilation and analysis of eukaryotic POL II promoter sequences. *Nucleic. Acids. Res.* 14, 10009–10026 incorporated herein by reference. Unlike the earlier reports, the experiments disclosed herein indicate the precise positioning of mRNA start site of human tyrosinase gene. The discrepancies in the mRNA start site determination could also be due to the different cell lines used in each of them. Similar differences in transcriptional start sites were also observed in mouse tyrosinase gene with different pigment cell lines (Ruppert et al., 1988; Yamamoto et al., 1989).

Analysis of the nucleotide sequences of the 5' flanking region of human tyrosinase gene indicates the presence of several transcription initiator and enhancer elements. The most common motifs TATA box and CCAAT were found at regions −27 and −128 bp upstream of the transcription initiation site. Apart from this, there was a core AP-1 site with sequence TGAGCTCA (Lee, W., Haslinger, A., Karin, M. and Tijan, R. (1987). Activation of transcription by two factors that bind promoter and enhancer sequences of the human metallothionein gene and SV40. *Nature.* 325, 368–372 incorporated herein by reference) found at −1297 bases upstream and five other close consensus for AP-1 were found at regions −103, −971, −1135, −1297 and −1673 bases upstream of the transcription initiation site. Two close consensus sequences for AP-2 element (Imagawa, M., Chiu, R. and Karin, M. (1987). Transcription factor AP-2 mediates induction by two different signal-transduction pathways: Protein kinase C and cAMP. *Cell.* 51,251–260 incorporated herein by reference) were found far upstream from the initiation site at −1856 and −1865 bp. Sequences similar to glucocorticoid responsive element (Beato, M. (1989). Gene regulation by steroid hormones. *Cell.* 56, 335–344. incorporated herein by reference) were found at −1379 and −1679 bases upstream. Oct-1, an apparently ubiquitous element in most mammalian cells (Strun, R., Das, G. and Herr, W. (1988). The ubiquitous octamer-binding protein Oct-1 contains POU domain with a homeo box subdomain. *Genes Dev.* 2, 1582–1599 incorporated herein by reference) was found at three regions −293, −1209 and −1737 bases upstream. Sequences resembling core UV responsive element (Ronai, Z. and Weinstein, I. B. (1990). Identification of ultraviolet-inducible proteins that bind to a TGACAACA sequence in the polyoma virus regulatory region. *Cancer Res.* 50, 5374–5381 incorporated herein by reference) were found at −1216 and −1894 bases upstream. The effect of UV-radiation on pigmentation has been well established earlier (Friedmann, P. S. and Gilchrest, B. A. (1987). Ultraviolet radiation directly induces pigment production by cultured human melanocytes. *J. Cell. Physiol.* 133, 88–94. incorporated herein by reference; Libow, L. F., Scheide, S., and DeLeo, V. A. (1988). Ultraviolet radiation acts as an independent mitogen for normal human melanocytes in culture. *Pigment Cell. Res.* 1, 397–401 incorporated herein by reference. Exposure to UV-radiation results in increased melanin content of human skin. Identification of UV-inducible proteins which bind specifically to octamer sequences of DNA suggest that these proteins may in concert with other cellular components could play a role in mediating cellular response to DNA damage (Ronai and Weinstein, 1990). Tyrosinase expression is induced in vivo by several factors such as isobutylmethylzanthine, melanocyte stimulating hormone (MSH) and phorbol esters (Halaban, R. and Lerner, A. B. (1977). The dual effect of melanocyte-stimulating hormone (MSH) on the growth of cultured mouse melanoma cells. *Exp. Cell. Res.* 108, 111–117 incorporated herein by reference; Halaban, R., Pomerantz, S. H. Marshall, S., Lambert, D. T. and Lerner, A. B. (1983). Regulation of tyrosinase in human melanocytes grown in culture. *J. Cell. Biol.* 97, 480–488. incorporated herein by reference; Halaban, R., Pomerantz, S. H., Marshall, S. and Lerner, A. B. (1984). Tyrosinase activity and abundance in cloudman melanoma cells. *Arch. Biochem. Biophys.* 230, 383–387 incorporated herein by reference). UV induced melanogenesis has also been suggested to be mediated by MSH. The presence of various cis-acting elements in the promoter region of the human tyrosinase gene probably indicate that tyrosinase gene transcription is mediated by multiple regulatory elements.

Promoter analysis of the 5' flanking region of the human tyrosinase gene was performed using transient expression system. Maximal CAT activity was observed in plasmid construct containing the entire 2.02 Kb promoter region in human melanoma cells. FIG. 28 shows a functional analysis of human tyrosinase gene promoter. Plasmids containing different lengths of human tyrosinase promoter fused to the CAT gene were transfected to human (Stilling) melanoma cell line. The relative CAT activities were expressed in terms of percentage. The numbers on the left indicate the length of promoter region linked to the reporter gene.

However, 91% of activity was also observed in plasmid construct bearing only −550 bp of the 5' flanking region. This observation suggests that potential regulatory elements governing tyrosinase gene expression lie within this region. Plasmid constructs having as little as 83 bases of the tyrosinase promoter showed 20% of CAT activity. This relative activity could probably reflect the basal level transcription involving the TATA box contained within this region. 48% and 76% CAT activity was observed in plasmid constructs with −258 bp and −438 bp of the promoter sequences. This region also contains a CAT box and canonical AP-1 and Oct-1 sequences. These results suggest that important cis-acting elements must be present between −83 and −550 bases upstream of human tyrosinase gene. The results on regions between −550 bp and −1739 bp of the 5' flanking sequence also indicate that human tyrosinase gene expression is controlled by multiple regulatory elements. CAT activities of plasmid construct with −1153 and −1739 bp promoter region indicated only 59% and 43% activity when compared to the −2020 bp promoter while 91% activity was retained in 5' flanking sequences covering up to −550 bp. This observation suggests that silencer elements should be present in the region between −550 and −1739 bp of the human tyrosinase promoter. The presence of other ubiquitous cis-acting elements in this region also suggests that repression and derepression of transcription in human tyrosinase gene is governed by selective interplay of the silencer and enhancer elements in overall transcriptional rate. The background CAT activity observed as 4% in native plasmid lacking tyrosinase promoter sequence (pCAT-Basic) is most likely due to bacterial vector sequences with fortuitous eukaryotic promoter activity as suggested earlier (Lopata, M. A., Sollner-Webb, B. and Cleveland, D. W. (1985). Surprising S1-resistant trimolecular hybrids.: Potential complication in interpretation of S1 mapping analyses. *Mol. Cell. Biol.* 5, 2842–2846., 1985 incorporated herein by reference; Kadesh, T. and Berg, P. (1986). Effect of the position of the simian virus 40 enhancer on expression of multiple transcription units in a single plasmid. *Mol. Cell. Biol.* 6, 2593–2601 incorporated herein by reference; Langner, K. D., Weyer, U. and Doerfler, W. (1986). Trans effect of the E1 region of adenoviruses on the expression of a prokaryotic gene in mammalian cells: Resistance to 5'-CCGG-3' methylation. *Proc. Natl. Acad. Sci. U.S.A.* 83, 1598–1602 incorporated herein by reference; de Wet, J. R., Wodd, K. V., DeLuca, M., Helinski, D. R. and Subramani, S. (1987). Firefly luciferase gene: structure and expression in mammalian cells. *Mol. Cell. Biol.* 7, 725–737 incorporated herein by reference). No CAT activity was observed when human tyrosinase promoter constructs were transfected in HeLa cells confirming their tissue specific expression.

The presence of an unique purine rich AG repeat domain at −634 bases upstream of transcription start site does not indicate any functional significance in transcription control of human tyrosinase gene since sequences within −550 bp bases of the 5' flanking sequence appears sufficient for reporter gene expression. Similar AG rich sequences are also found in mouse tyrosinase promoter but it was reported earlier that in mouse promoter as little as −270 bases was sufficient to induce tissue specific expression (Kluppel et al., 1991). Hence the presence of the purine rich domain is a mere indication of evolutionary conservation.

The promoter DNA sequence for the human tyrosinase gene and fragments and derivatives thereof: 1) can be used as a probe for similar coding sequences; 2) can be used as a probe for genetic analysis of human albinism; 3) can be used as a probe to develop systems which can find chemicals or factors regulating skin coloration; and 4) can be used to control production or regulation of human melanin.

The foregoing description has been directed to particular embodiments of the invention in accordance with the requirements of the Patent Statutes for the purposes of illustration and explanation. It will be apparent, however, to those skilled in this art that many modifications and changes will be possible without department from the scope and spirit of the invention. It is intended that the following claims be interpreted to embrace all such modifications.

---

I claim:

1. The cDNA gene comprising the cDNA isolated from the λmel 17-1 cDNA as deposited at the American Type Culture Collection at 12301 Parklawn Drive, Rockville, Md. 20852 under ATCC No. 40264.

2. A bacteriophage vector for use as a probe for melanin biosynthesis comprising a bacteriophage vector containing λmel 17-1 cDNA and on deposit at the American Type Culture Collection at 12301 Parklawn Drive, Rockville, Md. 20852 under ATCC No. 40264.

3. A method of detecting the degree of melanization in a human melanocyte, comprising the steps of:

a) subjecting human melanocyte RNA to a Northern blot analysis using cDNA isolated from the λmel 17-1 cDNA as deposited at the American Type Culture Collection under ATCC No. 40264 as a probe; and b) measuring the presence of said melanin therein by the amount of said probe that hybridizes during said Northern Blot analysis.

4. An isolated protein, Pmel 17, having an amino acid sequence as shown in SEQ ID NO:6.

5. A DNA selected from the group consisting of:

a) a purified and isolated DNA which encodes the protein shown in SEQ ID NO:6;

b) a purified and isolated DNA which encodes amino acids residues 24–668 shown in SEQ ID NO:6;

c) a purified and isolated DNA which encodes amino acids residues 315–394 shown in SEQ ID NO:6;

d) a purified and isolated DNA which encodes amino acids residues 315–340 shown in SEQ ID NO:6;

e) a purified and isolated DNA which encodes amino acids residues 341–366 shown in SEQ ID NO:6;

f) a purified and isolated DNA which encodes amino acids residues 367–392 shown in SEQ ID NO:6;

g) a purified and isolated DNA which encodes amino acids residues 598–623 shown in SEQ ID NO:6;

h) a purified and isolated DNA which encodes amino acids residues 141–435 shown in SEQ ID NO:6;

h) a purified and isolated DNA which encodes amino acids residues 598–623 shown in SEQ ID NO:6.

6. The DNA sequence of claim 5 which encodes the protein shown in SEQ ID NO:6.

* * * * *

UNITED STATES PATENT AND TRADEMARK OFFICE
CERTIFICATE OF CORRECTION

PATENT NO. : 5,679,511
DATED : Oct. 21, 1997
INVENTOR(S) : Byoung Se Kwon

It is certified that error appears in the above-identified patent and that said Letters Patent is hereby corrected as shown below:

Delete the text in Column 12, lines 12 – 18.

In the drawings substitute the page numbering on the 26 sheets of drawings to read:

1/26 - 2/26 - 3/26 - 4/26 - 5/26 - 6/26 - 7/26 - 8/26 - 9/26 - 10/26 - 11/26 -

12/26 - 13/26 - 14/26 - 15/26 - 16/26 - 17/26 - 18/28 - 19/26 - 20/26 - 21/26

22/26 - 23/26 - 24/26 - 25/26 - 26/26

The drawing sheet, consisting of Fig. 27, should be added as shown on the attached page.

Signed and Sealed this

Twenty-fourth Day of February, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligo fragment"

( x i ) SEQUENCE DESCRIPTION: SEQ ID NO:1:

TGATGTATTC          10

( 2 ) INFORMATION FOR SEQ ID NO:2:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="oligo fragment"

(xi) SEQUENCE DESCRIPTION: SEQ ID NO:2:

```
AGCTTGATGT ATTCTTGATA CTACTTA                                          27
```

(2) INFORMATION FOR SEQ ID NO:3:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="oligo fragment"

(xi) SEQUENCE DESCRIPTION: SEQ ID NO:3:

```
AGCTTAAGTA GTATCAAGAA TACATCA                                          27
```

(2) INFORMATION FOR SEQ ID NO:4:

(i) SEQUENCE CHARACTERISTICS:
(A) LENGTH: 1886 base pairs
(B) TYPE: nucleic acid
(C) STRANDEDNESS: double
(D) TOPOLOGY: linear (ii) MOLECULE TYPE: cDNA to mRNA (ix) FEATURE:
(A) NAME/KEY: CDS
(B) LOCATION: 7..1689

(ix) FEATURE:
(A) NAME/KEY: mat_peptide
(B) LOCATION: 43..1686

(ix) FEATURE:
(A) NAME/KEY: sig_peptide
(B) LOCATION: 7..42

(x) PUBLICATION INFORMATION:
(A) AUTHORS: Kwon, Byoung Se
            Haq, Asifa K
            Pomerantz, Seymour H
            Halaban, Ruth
(B) TITLE: Isolation and sequence of a cDNA clone for
           human tyrosinase that maps at the mouse c-albino
           locus
(C) JOURNAL: Proc. Natl. Acad. Sci. U.S.A.
(D) VOLUME: 84
(F) PAGES: 7473-7477
(G) DATE: November-1987
(K) RELEVANT RESIDUES IN SEQ ID NO:4: FROM 1 TO 1886

(xi) SEQUENCE DESCRIPTION: SEQ ID NO:4:

```
GAATTC CTG CTC CTG GCT GTT TTG TAC TGC CTG CTG TGG AGT TTC CAG         48
       Leu Leu Leu Ala Val Leu Tyr Cys Leu Leu Trp Ser Phe Gln
       -12     -10             -5                          1

ACC TCC GCT GGC CAT TTC CCT AGA GCC TGT GTC TCC TCT AAG AAC CTG        96
Thr Ser Ala Gly His Phe Pro Arg Ala Cys Val Ser Ser Lys Asn Leu
            5                   10                  15

ATG GAG AAG GAA TGC TGT CCA CCG TGG AGC GGG ACA GGA GTC TGT GGC       144
Met Glu Lys Glu Cys Cys Pro Pro Trp Ser Gly Thr Gly Val Cys Gly
        20                  25                  30
```

| | | | | | | | | | | | | | | | | |
|---|---|---|---|---|---|---|---|---|---|---|---|---|---|---|---|---|
| CAG | CTT | TCA | GGC | AGA | GGT | TCC | TGT | CAG | AAT | ATC | CTT | CTG | TCC | AAT | GCA | 192 |
| Gln | Leu | Ser | Gly | Arg | Gly | Ser | Cys | Gln | Asn | Ile | Leu | Leu | Ser | Asn | Ala | |
| 35 | | | | 40 | | | | | 45 | | | | | | 50 | |
| CCA | CTT | GGG | CCT | CAA | TTT | CCC | TTC | ACA | GGG | GTG | GAT | GAC | CGG | GAG | TCG | 240 |
| Pro | Leu | Gly | Pro | Gln | Phe | Pro | Phe | Thr | Gly | Val | Asp | Asp | Arg | Glu | Ser | |
| | | | | 55 | | | | | 60 | | | | | 65 | | |
| TGG | CCT | TCC | GTC | TTT | TAT | AAT | AGG | ACC | TGC | CAG | TGC | TCT | GGC | AAC | TTC | 288 |
| Trp | Pro | Ser | Val | Phe | Tyr | Asn | Arg | Thr | Cys | Gln | Cys | Ser | Gly | Asn | Phe | |
| | | | 70 | | | | | 75 | | | | | 80 | | | |
| ATG | GGA | TTC | AAC | TGT | GGA | AAC | TGC | AAG | TTT | GGC | TTT | TGG | GGA | CCA | AAC | 336 |
| Met | Gly | Phe | Asn | Cys | Gly | Asn | Cys | Lys | Phe | Gly | Phe | Trp | Gly | Pro | Asn | |
| | | | 85 | | | | 90 | | | | | 95 | | | | |
| TGC | ACA | GAG | AGA | CGA | CTC | TTG | GTG | AGA | AGA | AAC | ATC | TTC | GAT | TTG | AGT | 384 |
| Cys | Thr | Glu | Arg | Arg | Leu | Leu | Val | Arg | Arg | Asn | Ile | Phe | Asp | Leu | Ser | |
| 100 | | | | | 105 | | | | | | 110 | | | | | |
| GCC | CCA | GAG | AAG | GAC | AAA | TTT | TTT | GCC | TAC | CTC | ACT | TTA | GCA | AAG | CAT | 432 |
| Ala | Pro | Glu | Lys | Asp | Lys | Phe | Phe | Ala | Tyr | Leu | Thr | Leu | Ala | Lys | His | |
| 115 | | | | 120 | | | | | 125 | | | | | 130 | | |
| ACC | ATC | AGC | TCA | GAC | TAT | GTC | ATC | CCC | ATA | GGG | ACC | TAT | GGC | CAA | ATG | 480 |
| Thr | Ile | Ser | Ser | Asp | Tyr | Val | Ile | Pro | Ile | Gly | Thr | Tyr | Gly | Gln | Met | |
| | | | | 135 | | | | 140 | | | | | 145 | | | |
| AAA | AAT | GGA | TCA | ACA | CCC | ATG | TTT | AAC | GAC | ATC | AAT | ATT | TAT | GAC | CTC | 528 |
| Lys | Asn | Gly | Ser | Thr | Pro | Met | Phe | Asn | Asp | Ile | Asn | Ile | Tyr | Asp | Leu | |
| | | | 150 | | | | | 155 | | | | | 160 | | | |
| TTT | GTC | TGG | ATG | CAT | TAT | TAT | GTG | TCA | ATG | GAT | GCA | CTG | CTT | GGG | GGA | 576 |
| Phe | Val | Trp | Met | His | Tyr | Tyr | Val | Ser | Met | Asp | Ala | Leu | Leu | Gly | Gly | |
| | | 165 | | | | | 170 | | | | | 175 | | | | |
| TAT | GAA | ATC | TGG | AGA | GAC | ATT | GAT | TTT | GCC | CAT | GAA | GCA | CCA | GCT | TTT | 624 |
| Tyr | Glu | Ile | Trp | Arg | Asp | Ile | Asp | Phe | Ala | His | Glu | Ala | Pro | Ala | Phe | |
| | 180 | | | | | 185 | | | | | 190 | | | | | |
| CTG | CCT | TGG | CAT | AGA | CTC | TTC | TTG | TTG | CGG | TGG | GAA | CAA | GAA | ATC | CAG | 672 |
| Leu | Pro | Trp | His | Arg | Leu | Phe | Leu | Leu | Arg | Trp | Glu | Gln | Glu | Ile | Gln | |
| 195 | | | | | 200 | | | | | 205 | | | | | 210 | |
| AAG | CTG | ACA | GGA | GAT | GAA | AAC | TTC | ACT | ATT | CCA | TAT | TGG | GAC | TGG | CGG | 720 |
| Lys | Leu | Thr | Gly | Asp | Glu | Asn | Phe | Thr | Ile | Pro | Tyr | Trp | Asp | Trp | Arg | |
| | | | | 215 | | | | | 220 | | | | | 225 | | |
| GAT | GCA | GAA | AAG | TGT | GAC | ATT | TGC | ACA | GAT | GAG | TAC | ATG | GGA | GGT | CAG | 768 |
| Asp | Ala | Glu | Lys | Cys | Asp | Ile | Cys | Thr | Asp | Glu | Tyr | Met | Gly | Gly | Gln | |
| | | | 230 | | | | | 235 | | | | | 240 | | | |
| CAC | CCC | ACA | AAT | CCT | AGC | TTA | CTC | AGC | CCA | GCA | TCA | TTC | TTC | TCC | TCT | 816 |
| His | Pro | Thr | Asn | Pro | Ser | Leu | Leu | Ser | Pro | Ala | Ser | Phe | Phe | Ser | Ser | |
| | | 245 | | | | | 250 | | | | | 255 | | | | |
| TGG | CAG | ATT | GTC | TGT | ACC | CGA | TTG | GAG | GAG | TAC | AAC | AGC | CAT | CAG | TCT | 864 |
| Trp | Gln | Ile | Val | Cys | Thr | Arg | Leu | Glu | Glu | Tyr | Asn | Ser | His | Gln | Ser | |
| 260 | | | | | 265 | | | | | 270 | | | | | | |
| TTA | TGC | AAT | GGA | ACG | CCC | GAG | GGA | CCT | TTA | CGG | CGT | AAT | CCT | GGA | AAC | 912 |
| Leu | Cys | Asn | Gly | Thr | Pro | Glu | Gly | Pro | Leu | Arg | Arg | Asn | Pro | Gly | Asn | |
| 275 | | | | 280 | | | | | 285 | | | | | 290 | | |
| CAT | GAC | AAA | TCC | ACA | ACC | CCA | AGG | CTC | CCC | TCT | TCA | GCT | GAT | GTA | GAA | 960 |
| His | Asp | Lys | Ser | Thr | Thr | Pro | Arg | Leu | Pro | Ser | Ser | Ala | Asp | Val | Glu | |
| | | | | 295 | | | | 300 | | | | | 305 | | | |
| TTT | TGC | CTG | AGT | TTG | ACC | CAA | TAT | GAA | TCT | GGT | TCC | ATG | GAT | AAA | GCT | 1008 |
| Phe | Cys | Leu | Ser | Leu | Thr | Gln | Tyr | Glu | Ser | Gly | Ser | Met | Asp | Lys | Ala | |
| | | | 310 | | | | | 315 | | | | | 320 | | | |
| GCC | AAT | TTC | AGC | TTT | AGA | AAT | ACA | CTG | GAA | GGA | TTT | GCT | AGT | CCA | CTT | 1056 |
| Ala | Asn | Phe | Ser | Phe | Arg | Asn | Thr | Leu | Glu | Gly | Phe | Ala | Ser | Pro | Leu | |
| | | 325 | | | | | 330 | | | | | 335 | | | | |
| ACT | GGG | ATA | GCG | GAT | GCC | TCT | CAA | AGC | AGC | ATG | CAC | AAT | GCC | TTG | CAC | 1104 |
| Thr | Gly | Ile | Ala | Asp | Ala | Ser | Gln | Ser | Ser | Met | His | Asn | Ala | Leu | His | |
| 340 | | | | | 345 | | | | | 350 | | | | | | |

| | | | | | | | | | | | | | | | | |
|---|---|---|---|---|---|---|---|---|---|---|---|---|---|---|---|---|
|ATC|TAT|ATG|AAT|GGA|CAT|GTC|CCA|GGT|ACA|GGA|TCT|GCC|AAC|GAT|CCT|1152|
|Ile|Tyr|Met|Asn|Gly|His|Val|Pro|Gly|Thr|Gly|Ser|Ala|Asn|Asp|Pro||
|355| | | |360| | | |365| | | | | |370| | |
|ATC|TTC|CTT|CTT|CAC|CAT|GCA|TTT|GTT|GAC|AGT|ATT|TTT|GAG|CAG|TGG|1200|
|Ile|Phe|Leu|Leu|His|His|Ala|Phe|Val|Asp|Ser|Ile|Phe|Glu|Gln|Trp||
| | | | |375| | | |380| | | |385| | | | |
|CTC|CAA|AGG|CAC|CGT|CCT|CTT|CAA|GAA|GTT|TAT|CCA|GAA|GCC|AAT|GCA|1248|
|Leu|Gln|Arg|His|Arg|Pro|Leu|Gln|Glu|Val|Tyr|Pro|Glu|Ala|Asn|Ala||
| | |390| | | | |395| | | | |400| | | | |
|CCC|ATT|GGA|CAT|AAC|CGG|GAA|TCC|TAC|ATG|GTT|CCT|TTT|ATA|CCA|CTG|1296|
|Pro|Ile|Gly|His|Asn|Arg|Glu|Ser|Tyr|Met|Val|Pro|Phe|Ile|Pro|Leu||
| | |405| | | |410| | | | |415| | | | | |
|TAC|AGA|AAT|GGT|GAT|TTC|TTT|ATT|TCA|TCC|AAA|GAT|CTG|GGC|TAT|GAC|1344|
|Tyr|Arg|Asn|Gly|Asp|Phe|Phe|Ile|Ser|Ser|Lys|Asp|Leu|Gly|Tyr|Asp||
| |420| | | |425| | | | |430| | | | | | |
|TAT|AGC|TAT|CTA|CAA|GAT|TCA|GAC|CCA|GAC|TCT|TTT|CAA|GAC|TAC|ATT|1392|
|Tyr|Ser|Tyr|Leu|Gln|Asp|Ser|Asp|Pro|Asp|Ser|Phe|Gln|Asp|Tyr|Ile||
|435| | | |440| | | |445| | | |450| | | | |
|AAG|TCC|TAT|TTG|GAA|CAA|GCG|AGT|CGG|ATC|TGG|TCA|TGG|CTC|CTT|GGG|1440|
|Lys|Ser|Tyr|Leu|Glu|Gln|Ala|Ser|Arg|Ile|Trp|Ser|Trp|Leu|Leu|Gly||
| | | |455| | | |460| | | | |465| | | | |
|GCG|GCG|ATG|GTA|GGG|GCC|GTC|CTC|ACT|GCC|CTG|CTG|GCA|GGG|CCT|GTG|1488|
|Ala|Ala|Met|Val|Gly|Ala|Val|Leu|Thr|Ala|Leu|Leu|Ala|Gly|Pro|Val||
| | |470| | | |475| | | | |480| | | | | |
|AGC|TTG|CTG|TGT|CGT|CAC|AAG|AGA|AAG|CAG|CTT|CCT|GAA|GAA|AAG|CAG|1536|
|Ser|Leu|Leu|Cys|Arg|His|Lys|Arg|Lys|Gln|Leu|Pro|Glu|Glu|Lys|Gln||
| |485| | | | |490| | | | |495| | | | | |
|CCA|CTC|CTC|ATG|GAG|AAA|GAA|GGA|TTA|CCA|CAG|CTT|GTA|TCA|GAG|CCA|1584|
|Pro|Leu|Leu|Met|Glu|Lys|Glu|Gly|Leu|Pro|Gln|Leu|Val|Ser|Glu|Pro||
|500| | | | |505| | | | |510| | | | | | |
|TTT|ATA|AAA|GGC|TTA|GGC|AAT|AGA|GTA|GGG|CCA|AAA|AGC|CCT|GAC|CTC|1632|
|Phe|Ile|Lys|Gly|Leu|Gly|Asn|Arg|Val|Gly|Pro|Lys|Ser|Pro|Asp|Leu||
|515| | | |520| | | |525| | | |530| | | | |
|ACT|CTA|ACT|CAA|AGT|AAT|GTC|CAG|GTT|CCA|GAG|AAT|ATC|TGC|TGG|TAT|1680|
|Thr|Leu|Thr|Gln|Ser|Asn|Val|Gln|Val|Pro|Glu|Asn|Ile|Cys|Trp|Tyr||
| | | |535| | | |540| | | |545| | | | | |

| | | | | | |
|---|---|---|---|---|---|
|TTT|CTG|TAA|AGACCATTTG|CAAAATTGTA|ACCTAATACA AAGTGTAGCC|1729|
|Phe|Leu|*| | | |

TTCTTCCAAC TCAGGTAGAA CACACCTGTC TTTGTCTTGC TGTTTTCACT CAGCCCTTTT    1789

AACATTTTCC CCTAAGCCCA TATGTCTAAG GAAAGGATGC TATTTGGTAA TGAGGAACTG    1849

TTATTTGTAT GTGAATTAAA AGTGCTCTTA GGAATTC    1886

( 2 ) INFORMATION FOR SEQ ID NO:5:

( i ) SEQUENCE CHARACTERISTICS:
        ( A ) LENGTH: 560 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| | | | | | | | | | | | | | |
|---|---|---|---|---|---|---|---|---|---|---|---|---|---|
|Leu|Leu|Leu|Ala|Val|Leu|Tyr|Cys|Leu|Leu|Trp|Ser|Phe|Gln|Thr|Ser|
|-12| |-10| | | | |-5| | | | |1| | |
|Ala|Gly|His|Phe|Pro|Arg|Ala|Cys|Val|Ser|Ser|Lys|Asn|Leu|Met|Glu|
|5| | | |10| | | |15| | | |20| | | |
|Lys|Glu|Cys|Cys|Pro|Pro|Trp|Ser|Gly|Thr|Gly|Val|Cys|Gly|Gln|Leu|
| | |25| | | | |30| | | | |35| | | |
|Ser|Gly|Arg|Gly|Ser|Cys|Gln|Asn|Ile|Leu|Leu|Ser|Asn|Ala|Pro|Leu|

-continued

|  |  |  | 40 |  |  |  |  |  | 45 |  |  |  |  | 50 |  |  |
|---|---|---|---|---|---|---|---|---|---|---|---|---|---|---|---|---|
| Gly | Pro | Gln | Phe | Pro | Phe | Thr | Gly | Val | Asp | Asp | Arg | Glu | Ser | Trp | Pro |
|  |  | 55 |  |  |  |  | 60 |  |  |  |  | 65 |  |  |  |
| Ser | Val | Phe | Tyr | Asn | Arg | Thr | Cys | Gln | Cys | Ser | Gly | Asn | Phe | Met | Gly |
|  | 70 |  |  |  |  | 75 |  |  |  |  | 80 |  |  |  |  |
| Phe | Asn | Cys | Gly | Asn | Cys | Lys | Phe | Gly | Phe | Trp | Gly | Pro | Asn | Cys | Thr |
| 85 |  |  |  |  | 90 |  |  |  |  | 95 |  |  |  |  | 100 |
| Glu | Arg | Arg | Leu | Leu | Val | Arg | Arg | Asn | Ile | Phe | Asp | Leu | Ser | Ala | Pro |
|  |  |  | 105 |  |  |  |  |  | 110 |  |  |  |  | 115 |  |
| Glu | Lys | Asp | Lys | Phe | Phe | Ala | Tyr | Leu | Thr | Leu | Ala | Lys | His | Thr | Ile |
|  |  |  | 120 |  |  |  |  |  | 125 |  |  |  |  | 130 |  |
| Ser | Ser | Asp | Tyr | Val | Ile | Pro | Ile | Gly | Thr | Tyr | Gly | Gln | Met | Lys | Asn |
|  |  | 135 |  |  |  |  |  | 140 |  |  |  |  | 145 |  |  |
| Gly | Ser | Thr | Pro | Met | Phe | Asn | Asp | Ile | Asn | Ile | Tyr | Asp | Leu | Phe | Val |
|  | 150 |  |  |  |  | 155 |  |  |  |  | 160 |  |  |  |  |
| Trp | Met | His | Tyr | Tyr | Val | Ser | Met | Asp | Ala | Leu | Leu | Gly | Gly | Tyr | Glu |
| 165 |  |  |  |  | 170 |  |  |  |  | 175 |  |  |  |  | 180 |
| Ile | Trp | Arg | Asp | Ile | Asp | Phe | Ala | His | Glu | Ala | Pro | Ala | Phe | Leu | Pro |
|  |  |  |  | 185 |  |  |  |  | 190 |  |  |  |  | 195 |  |
| Trp | His | Arg | Leu | Phe | Leu | Leu | Arg | Trp | Glu | Gln | Glu | Ile | Gln | Lys | Leu |
|  |  |  | 200 |  |  |  |  |  | 205 |  |  |  |  | 210 |  |
| Thr | Gly | Asp | Glu | Asn | Phe | Thr | Ile | Pro | Tyr | Trp | Asp | Trp | Arg | Asp | Ala |
|  |  |  | 215 |  |  |  |  |  | 220 |  |  |  |  | 225 |  |
| Glu | Lys | Cys | Asp | Ile | Cys | Thr | Asp | Glu | Tyr | Met | Gly | Gly | Gln | His | Pro |
|  |  |  | 230 |  |  |  |  | 235 |  |  |  |  | 240 |  |  |
| Thr | Asn | Pro | Ser | Leu | Leu | Ser | Pro | Ala | Ser | Phe | Phe | Ser | Ser | Trp | Gln |
| 245 |  |  |  |  | 250 |  |  |  |  | 255 |  |  |  |  | 260 |
| Ile | Val | Cys | Thr | Arg | Leu | Glu | Glu | Tyr | Asn | Ser | His | Gln | Ser | Leu | Cys |
|  |  |  |  | 265 |  |  |  |  | 270 |  |  |  |  | 275 |  |
| Asn | Gly | Thr | Pro | Glu | Gly | Pro | Leu | Arg | Arg | Asn | Pro | Gly | Asn | His | Asp |
|  |  |  | 280 |  |  |  |  |  | 285 |  |  |  |  | 290 |  |
| Lys | Ser | Thr | Thr | Pro | Arg | Leu | Pro | Ser | Ser | Ala | Asp | Val | Glu | Phe | Cys |
|  |  |  | 295 |  |  |  |  | 300 |  |  |  |  | 305 |  |  |
| Leu | Ser | Leu | Thr | Gln | Tyr | Glu | Ser | Gly | Ser | Met | Asp | Lys | Ala | Ala | Asn |
|  | 310 |  |  |  |  | 315 |  |  |  |  | 320 |  |  |  |  |
| Phe | Ser | Phe | Arg | Asn | Thr | Leu | Glu | Gly | Phe | Ala | Ser | Pro | Leu | Thr | Gly |
| 325 |  |  |  |  | 330 |  |  |  |  | 335 |  |  |  |  | 340 |
| Ile | Ala | Asp | Ala | Ser | Gln | Ser | Ser | Met | His | Asn | Ala | Leu | His | Ile | Tyr |
|  |  |  |  | 345 |  |  |  |  | 350 |  |  |  |  | 355 |  |
| Met | Asn | Gly | His | Val | Pro | Gly | Thr | Gly | Ser | Ala | Asn | Asp | Pro | Ile | Phe |
|  |  |  | 360 |  |  |  |  | 365 |  |  |  |  | 370 |  |  |
| Leu | Leu | His | His | Ala | Phe | Val | Asp | Ser | Ile | Phe | Glu | Gln | Trp | Leu | Gln |
|  |  | 375 |  |  |  |  | 380 |  |  |  |  | 385 |  |  |  |
| Arg | His | Arg | Pro | Leu | Gln | Glu | Val | Tyr | Pro | Glu | Ala | Asn | Ala | Pro | Ile |
|  | 390 |  |  |  |  | 395 |  |  |  |  | 400 |  |  |  |  |
| Gly | His | Asn | Arg | Glu | Ser | Tyr | Met | Val | Pro | Phe | Ile | Pro | Leu | Tyr | Arg |
| 405 |  |  |  |  | 410 |  |  |  |  | 415 |  |  |  |  | 420 |
| Asn | Gly | Asp | Phe | Phe | Ile | Ser | Ser | Lys | Asp | Leu | Gly | Tyr | Asp | Tyr | Ser |
|  |  |  |  | 425 |  |  |  |  | 430 |  |  |  |  | 435 |  |
| Tyr | Leu | Gln | Asp | Ser | Asp | Pro | Asp | Ser | Phe | Gln | Asp | Tyr | Ile | Lys | Ser |
|  |  |  | 440 |  |  |  |  | 445 |  |  |  |  | 450 |  |  |
| Tyr | Leu | Glu | Gln | Ala | Ser | Arg | Ile | Trp | Ser | Trp | Leu | Leu | Gly | Ala | Ala |
|  |  |  | 455 |  |  |  |  | 460 |  |  |  |  | 465 |  |  |

```
Met  Val  Gly  Ala  Val  Leu  Thr  Ala  Leu  Leu  Ala  Gly  Pro  Val  Ser  Leu
     470                 475                      480

Leu  Cys  Arg  His  Lys  Arg  Lys  Gln  Leu  Pro  Glu  Glu  Lys  Gln  Pro  Leu
485                      490                      495                      500

Leu  Met  Glu  Lys  Gly  Leu  Pro  Gln  Leu  Val  Ser  Glu  Pro  Phe  Ile
                    505                 510                      515

Lys  Gly  Leu  Gly  Asn  Arg  Val  Gly  Pro  Lys  Ser  Pro  Asp  Leu  Thr  Leu
                    520                 525                      530

Thr  Gln  Ser  Asn  Val  Gln  Val  Pro  Glu  Asn  Ile  Cys  Trp  Tyr  Phe  Leu
               535                 540                      545
```

( 2 ) INFORMATION FOR SEQ ID NO:6:

( i ) SEQUENCE CHARACTERISTICS:
        ( A ) LENGTH: 668 amino acids
        ( B ) TYPE: amino acid
        ( C ) STRANDEDNESS: single
        ( D ) TOPOLOGY: linear ( i i ) MOLECULE TYPE: protein ( x ) PUBLICATION INFORMATION:
        ( A ) AUTHORS: Kwon, Byoung Se
                Chintamaneni, Chaya
                Kozak, Christine A
                Copeland, Neal G
                Gilbert, Debra J
                Jenkins, Nancy
                Barton, David
                Francke, Uta
                Kobayashi, Yvonne
                Kim, Kack K
        ( B ) TITLE: A melanocyte-specific gene, Pmel 17, maps
               near the silver coat color locus on mouse
               chromosome 10 and is in a syntenic region on human
               chromosome 12
        ( C ) JOURNAL: Proc. Natl. Acad. Sci. U.S.A.
        ( D ) VOLUME: 88
        ( F ) PAGES: 9228-9232
        ( G ) DATE: October-1991
        ( K ) RELEVANT RESIDUES IN SEQ ID NO:6: FROM 1 TO 668

( x i ) SEQUENCE DESCRIPTION: SEQ ID NO:6:

```
Met  Asp  Leu  Val  Leu  Lys  Arg  Cys  Leu  Leu  His  Leu  Ala  Val  Ile  Gly
1                   5                      10                      15

Ala  Leu  Leu  Ala  Val  Gly  Ala  Thr  Lys  Val  Pro  Arg  Asn  Gln  Asp  Trp
               20                 25                      30

Leu  Gly  Val  Ser  Arg  Gln  Leu  Arg  Thr  Lys  Ala  Trp  Asn  Arg  Gln  Leu
          35                 40                      45

Tyr  Pro  Glu  Trp  Thr  Glu  Ala  Gln  Arg  Leu  Asp  Cys  Trp  Arg  Gly  Gly
     50                 55                      60

Gln  Val  Ser  Leu  Lys  Val  Ser  Asn  Asp  Gly  Pro  Thr  Leu  Ile  Gly  Ala
65                  70                 75                            80

Asn  Ala  Ser  Phe  Ser  Ile  Ala  Leu  Asn  Phe  Pro  Gly  Ser  Gln  Lys  Val
               85                 90                      95

Leu  Pro  Asp  Gln  Gly  Val  Ile  Trp  Val  Asn  Asn  Thr  Ile  Ile  Asn  Gly
               100                105                     110

Ser  Gln  Val  Trp  Gly  Gly  Gln  Pro  Val  Tyr  Pro  Gln  Glu  Thr  Asp  Asp
          115                 120                     125

Ala  Cys  Ile  Phe  Pro  Asp  Gly  Gly  Pro  Cys  Pro  Ser  Gly  Ser  Trp  Ser
     130                 135                     140

Gln  Lys  Arg  Ser  Phe  Val  Tyr  Val  Trp  Lys  Thr  Trp  Gly  Gln  Tyr  Trp
145                     150                     155                     160

Gln  Val  Leu  Gly  Gly  Pro  Val  Ser  Gly  Leu  Ser  Ile  Gly  Thr  Gly  Arg
```

|     |     |     |     |     | 165 |     |     |     | 170 |     |     |     |     | 175 |     |
| --- | --- | --- | --- | --- | --- | --- | --- | --- | --- | --- | --- | --- | --- | --- | --- |
| Ala | Met | Leu | Gly<br>180 | Thr | His | Thr | Met | Glu<br>185 | Val | Thr | Val | Tyr | His<br>190 | Arg | Arg |
| Gly | Ser | Arg<br>195 | Ser | Tyr | Val | Pro | Leu<br>200 | Ala | His | Ser | Ser | Ser<br>205 | Ala | Phe | Thr |
| Ile | Thr<br>210 | Asp | Gln | Val | Pro | Phe<br>215 | Ser | Val | Ser | Val | Ser<br>220 | Gln | Leu | Arg | Ala |
| Leu<br>225 | Asp | Gly | Gly | Asn | Lys<br>230 | His | Phe | Leu | Arg | Asn<br>235 | Gln | Pro | Leu | Thr | Phe<br>240 |
| Ala | Leu | Gln | Leu | His<br>245 | Asp | Pro | Ser | Gly | Tyr<br>250 | Leu | Ala | Glu | Ala | Asp<br>255 | Leu |
| Ser | Tyr | Thr | Trp<br>260 | Asp | Phe | Gly | Asp | Ser<br>265 | Ser | Gly | Thr | Leu | Ile<br>270 | Ser | Arg |
| Ala | Pro | Val<br>275 | Val | Thr | His | Thr | Tyr<br>280 | Leu | Glu | Pro | Gly | Pro<br>285 | Val | Thr | Ala |
| Gln | Val<br>290 | Val | Leu | Gln | Ala | Ala<br>295 | Ile | Pro | Leu | Thr | Ser<br>300 | Cys | Gly | Ser | Ser |
| Pro<br>305 | Val | Pro | Gly | Thr | Thr<br>310 | Asp | Gly | His | Arg | Pro<br>315 | Thr | Ala | Glu | Ala | Pro<br>320 |
| Asn | Thr | Thr | Ala | Gly<br>325 | Gln | Val | Pro | Thr | Thr<br>330 | Glu | Val | Val | Gly | Thr<br>335 | Thr |
| Pro | Gly | Gln | Ala<br>340 | Pro | Thr | Ala | Glu | Pro<br>345 | Ser | Gly | Thr | Thr | Ser<br>350 | Val | Gln |
| Val | Pro | Thr<br>355 | Thr | Glu | Val | Ile | Ser<br>360 | Thr | Ala | Pro | Val | Gln<br>365 | Met | Pro | Thr |
| Ala | Glu<br>370 | Ser | Thr | Gly | Met<br>375 | Thr | Pro | Glu | Lys | Val<br>380 | Pro | Val | Ser | Glu | Val |
| Met<br>385 | Gly | Thr | Thr | Leu | Ala<br>390 | Glu | Met | Ser | Thr | Pro<br>395 | Glu | Ala | Thr | Gly | Met<br>400 |
| Thr | Pro | Ala | Glu | Val<br>405 | Ser | Ile | Val | Val | Leu<br>410 | Ser | Gly | Thr | Thr | Ala<br>415 | Ala |
| Gln | Val | Thr | Thr<br>420 | Thr | Glu | Trp | Val | Glu<br>425 | Thr | Thr | Ala | Arg | Glu<br>430 | Leu | Pro |
| Ile | Pro | Glu<br>435 | Pro | Glu | Gly | Pro | Asp<br>440 | Ala | Ser | Ser | Ile | Met<br>445 | Ser | Thr | Glu |
| Ser | Ile<br>450 | Thr | Gly | Ser | Leu | Gly<br>455 | Pro | Leu | Leu | Asp | Gly<br>460 | Thr | Ala | Thr | Leu |
| Arg<br>465 | Leu | Val | Lys | Arg | Gln<br>470 | Val | Pro | Leu | Asp | Cys<br>475 | Val | Leu | Tyr | Arg | Tyr<br>480 |
| Gly | Ser | Phe | Ser | Val<br>485 | Thr | Leu | Asp | Ile | Val<br>490 | Gln | Gly | Ile | Glu | Ser<br>495 | Ala |
| Glu | Ile | Leu | Gln | Ala<br>500 | Val | Pro | Ser | Gly | Glu<br>505 | Gly | Asp | Ala | Phe | Glu<br>510 | Leu |
| Thr | Val | Ser | Cys<br>515 | Gln | Ser | Gly | Leu | Pro<br>520 | Lys | Glu | Ala | Cys<br>525 | Met | Glu | Ile |
| Ser | Ser<br>530 | Pro | Gly | Cys | Gln | Pro<br>535 | Pro | Ala | Gln | Arg | Leu<br>540 | Cys | Gln | Pro | Val |
| Leu<br>545 | Pro | Ser | Pro | Ala | Cys<br>550 | Gln | Leu | Val | Leu | His<br>555 | Gln | Ile | Leu | Lys | Gly<br>560 |
| Gly | Ser | Gly | Thr | Tyr<br>565 | Cys | Leu | Asn | Val | Ser<br>570 | Leu | Ala | Asp | Thr | Asn<br>575 | Ser |
| Leu | Ala | Val | Val<br>580 | Ser | Thr | Gln | Leu | Ile<br>585 | Met | Pro | Val | Pro | Gly<br>590 | Ile | Leu |

```
        Leu  Thr  Gly  Gln  Glu  Ala  Gly  Leu  Gly  Gln  Val  Pro  Leu  Ile  Val  Gly
             595                 600                      605

Ile  Leu  Leu  Val  Leu  Met  Ala  Val  Val  Leu  Ala  Ser  Leu  Ile  Tyr  Arg
             610                 615                      620

Arg  Arg  Leu  Met  Lys  Gln  Asp  Phe  Ser  Val  Pro  Gln  Leu  Pro  His  Ser
        625                 630                      635                           640

Ser  Ser  His  Trp  Leu  Arg  Leu  Pro  Arg  Ile  Phe  Cys  Ser  Cys  Pro  Ile
                            645                      650                      655

Gly  Glu  Asn  Ser  Pro  Leu  Leu  Ser  Gly  Gln  Gln  Val
                       660                 665
```

( 2 ) INFORMATION FOR SEQ ID NO:7:

( i ) SEQUENCE CHARACTERISTICS:
        ( A ) LENGTH: 1920 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 32..1621

( i x ) FEATURE:
        ( A ) NAME/KEY: mat_peptide
        ( B ) LOCATION: 86..1618

( i x ) FEATURE:
        ( A ) NAME/KEY: sig_peptide
        ( B ) LOCATION: 32..85

( x ) PUBLICATION INFORMATION:
        ( A ) AUTHORS: Chintamaneni, Chaya D
                       Halaban, Ruth
                       Kobayashi, Yvonne
                       Witkop, Carl J
                       Kwon, Byoung Se
        ( B ) TITLE: A single base insertion in the putative
                transmembrane domain of the tyrosinase gene as a
                cause for tyrosinase-negative oculocutaneous
                albinism
        ( C ) JOURNAL: Proc. Natl. Acad. Sci. U.S.A.
        ( D ) VOLUME: 88
        ( F ) PAGES: 5272-5276
        ( G ) DATE: June-1991

( x i ) SEQUENCE DESCRIPTION: SEQ ID NO:7:

```
TCCTGCAGAC  CTTGTGAGGA  CTAGAGGAAG  A  ATG  CTC  CTG  GCT  GTT  TTG  TAC                52
                                       Met  Leu  Leu  Ala  Val  Leu  Tyr
                                       -18                 -15

TGC  CTG  CTG  TGG  AGT  TTC  CAG  ACC  TCC  GCT  GGC  CAT  TTC  CCT  AGA  GCC          100
Cys  Leu  Leu  Trp  Ser  Phe  Gln  Thr  Ser  Ala  Gly  His  Phe  Pro  Arg  Ala
-10                      -5                      1                        5

TGT  GTC  TCC  TCT  AAG  AAC  CTG  ATG  GAG  AAG  GAA  TGC  TGT  CCA  CCG  TGG          148
Cys  Val  Ser  Ser  Lys  Asn  Leu  Met  Glu  Lys  Glu  Cys  Cys  Pro  Pro  Trp
                    10                      15                      20

AGC  GGG  GAC  AGG  AGT  CCC  TGT  GGC  CAG  CTT  TCA  GGC  AGA  GGT  TCC  TGT          196
Ser  Gly  Asp  Arg  Ser  Pro  Cys  Gly  Gln  Leu  Ser  Gly  Arg  Gly  Ser  Cys
               25                      30                      35

CAG  AAT  ATC  CTT  CTG  TCC  AAT  GCA  CCA  CTT  GGG  CCT  CAA  TTT  CCC  TTC          244
Gln  Asn  Ile  Leu  Leu  Ser  Asn  Ala  Pro  Leu  Gly  Pro  Gln  Phe  Pro  Phe
               40                      45                      50

ACA  GGG  GTG  GAT  GAC  CGG  GAG  TCG  TGG  CCT  TCC  GTC  TTT  TAT  AAT  AGG          292
Thr  Gly  Val  Asp  Asp  Arg  Glu  Ser  Trp  Pro  Ser  Val  Phe  Tyr  Asn  Arg
     55                      60                      65

ACC  TGC  CAG  TGC  TCT  GGC  AAC  TTC  ATG  GGA  TTC  AAC  TGT  GGA  AAC  TGC          340
```

|     |     |     |     |     |     |     |     |     |     |     |     |     |     |     |     |     |
|---|---|---|---|---|---|---|---|---|---|---|---|---|---|---|---|---|
| Thr | Cys | Gln | Cys | Ser | Gly | Asn | Phe | Met | Gly | Phe | Asn | Cys | Gly | Asn | Cys | |
| 70 | | | | 75 | | | | 80 | | | | | 85 | | | |

| AAG | TTT | GGC | TTT | TGG | GGA | CCA | AAC | TGC | ACA | GAG | AGA | CGA | CTC | TTG | GTG | 388 |
|---|---|---|---|---|---|---|---|---|---|---|---|---|---|---|---|---|
| Lys | Phe | Gly | Phe | Trp | Gly | Pro | Asn | Cys | Thr | Glu | Arg | Arg | Leu | Leu | Val | |
| | | | | 90 | | | | 95 | | | | | 100 | | | |
| AGA | AGA | AAC | ATC | TTC | GAT | TTG | AGT | GCC | CCA | GAG | AAG | GAC | AAA | TTT | TTT | 436 |
| Arg | Arg | Asn | Ile | Phe | Asp | Leu | Ser | Ala | Pro | Glu | Lys | Asp | Lys | Phe | Phe | |
| | | | 105 | | | | | 110 | | | | | 115 | | | |
| GCC | TAC | CTC | ACT | TTA | GCA | AAG | CAT | ACC | ATC | AGC | TCA | GAC | TAT | GTC | ATC | 484 |
| Ala | Tyr | Leu | Thr | Leu | Ala | Lys | His | Thr | Ile | Ser | Ser | Asp | Tyr | Val | Ile | |
| | | | 120 | | | | 125 | | | | | 130 | | | | |
| CCC | ATA | GGG | ACC | TAT | GGC | CAA | ATG | AAA | AAT | GGA | TCA | ACA | CCC | ATG | TTT | 532 |
| Pro | Ile | Gly | Thr | Tyr | Gly | Gln | Met | Lys | Asn | Gly | Ser | Thr | Pro | Met | Phe | |
| | | 135 | | | | | 140 | | | | | 145 | | | | |
| AAC | GAC | ATC | AAT | ATT | TAT | GAC | CTC | TTT | GTC | TGG | ATG | CAT | TAT | TAT | GTG | 580 |
| Asn | Asp | Ile | Asn | Ile | Tyr | Asp | Leu | Phe | Val | Trp | Met | His | Tyr | Tyr | Val | |
| 150 | | | | | 155 | | | | | 160 | | | | | 165 | |
| TCA | ATG | GAT | GCA | CTG | CTT | GGG | GGA | TAT | GAA | ATC | TGG | AGA | GAC | ATT | GAT | 628 |
| Ser | Met | Asp | Ala | Leu | Leu | Gly | Gly | Tyr | Glu | Ile | Trp | Arg | Asp | Ile | Asp | |
| | | | | 170 | | | | | 175 | | | | | 180 | | |
| TTT | GCC | CAT | GAA | GCA | CCA | GCT | TTT | CTG | CCT | TGG | CAT | AGA | CTC | TTC | TTG | 676 |
| Phe | Ala | His | Glu | Ala | Pro | Ala | Phe | Leu | Pro | Trp | His | Arg | Leu | Phe | Leu | |
| | | | 185 | | | | | 190 | | | | | 195 | | | |
| TTG | CGG | TGG | GAA | CAA | GAA | ATC | CAG | AAG | CTG | ACA | GGA | GAT | GAA | AAC | TTC | 724 |
| Leu | Arg | Trp | Glu | Gln | Glu | Ile | Gln | Lys | Leu | Thr | Gly | Asp | Glu | Asn | Phe | |
| | | 200 | | | | | 205 | | | | | 210 | | | | |
| ACT | ATT | CCA | TAT | TGG | GAC | TGG | CGG | GAT | GCA | GAA | AAG | TGT | GAC | ATT | TGC | 772 |
| Thr | Ile | Pro | Tyr | Trp | Asp | Trp | Arg | Asp | Ala | Glu | Lys | Cys | Asp | Ile | Cys | |
| | 215 | | | | | 220 | | | | | 225 | | | | | |
| ACA | GAT | GAG | TAC | ATG | GGA | GGT | CAG | CAC | CCC | ACA | AAT | CCT | AGC | TTA | CTC | 820 |
| Thr | Asp | Glu | Tyr | Met | Gly | Gly | Gln | His | Pro | Thr | Asn | Pro | Ser | Leu | Leu | |
| 230 | | | | | 235 | | | | | 240 | | | | | 245 | |
| AGC | CCA | GCA | TCA | TTC | TTC | TCC | TCT | TGG | CAG | ATT | GTC | TGT | ACC | CGA | TTG | 868 |
| Ser | Pro | Ala | Ser | Phe | Phe | Ser | Ser | Trp | Gln | Ile | Val | Cys | Thr | Arg | Leu | |
| | | | | 250 | | | | | 255 | | | | | 260 | | |
| GAG | GAG | TAC | AAC | AGC | CAT | CAG | TCT | TTA | TGC | AAT | GGA | ACG | CCC | GAG | GGA | 916 |
| Glu | Glu | Tyr | Asn | Ser | His | Gln | Ser | Leu | Cys | Asn | Gly | Thr | Pro | Glu | Gly | |
| | | | 265 | | | | | 270 | | | | | 275 | | | |
| CCT | TTA | CGG | CGT | AAT | CCT | GGA | AAC | CAT | GAC | AAA | TCC | ACA | ACC | CCA | AGG | 964 |
| Pro | Leu | Arg | Arg | Asn | Pro | Gly | Asn | His | Asp | Lys | Ser | Thr | Thr | Pro | Arg | |
| | | 280 | | | | | 285 | | | | | 290 | | | | |
| CTC | CCC | TCT | TCA | GCT | GAT | GTA | GAA | TTT | TGC | CTG | AGT | TTG | ACC | CAA | TAT | 1012 |
| Leu | Pro | Ser | Ser | Ala | Asp | Val | Glu | Phe | Cys | Leu | Ser | Leu | Thr | Gln | Tyr | |
| | 295 | | | | | 300 | | | | | 305 | | | | | |
| GAA | TCT | GGT | TCC | ATG | GAT | AAA | GCT | GCC | AAT | TTC | AGC | TTT | AGA | AAT | ACA | 1060 |
| Glu | Ser | Gly | Ser | Met | Asp | Lys | Ala | Ala | Asn | Phe | Ser | Phe | Arg | Asn | Thr | |
| 310 | | | | | 315 | | | | | 320 | | | | | 325 | |
| CTG | GAA | GGA | TTT | GCT | AGT | CCA | CTT | ACT | GGG | ATA | GCG | GAT | GCC | TCT | CAA | 1108 |
| Leu | Glu | Gly | Phe | Ala | Ser | Pro | Leu | Thr | Gly | Ile | Ala | Asp | Ala | Ser | Gln | |
| | | | | 330 | | | | | 335 | | | | | 340 | | |
| AGC | AGC | ATG | CAC | AAT | GCC | TTG | CAC | ATC | TAT | ATG | AAT | GGA | ACA | ATG | TCC | 1156 |
| Ser | Ser | Met | His | Asn | Ala | Leu | His | Ile | Tyr | Met | Asn | Gly | Thr | Met | Ser | |
| | | | 345 | | | | | 350 | | | | | 355 | | | |
| CAG | GTA | CAG | GGA | TCT | GCC | AAC | GAT | CCT | ATC | TTC | CTT | CTT | CAC | CAT | GCA | 1204 |
| Gln | Val | Gln | Gly | Ser | Ala | Asn | Asp | Pro | Ile | Phe | Leu | Leu | His | His | Ala | |
| | | 360 | | | | | 365 | | | | | 370 | | | | |
| TTT | GTT | GAC | AGT | ATT | TTT | GAG | CAG | TGG | CTC | CAA | AGG | CAC | CGT | CCT | CTT | 1252 |
| Phe | Val | Asp | Ser | Ile | Phe | Glu | Gln | Trp | Leu | Gln | Arg | His | Arg | Pro | Leu | |
| | 375 | | | | | 380 | | | | | 385 | | | | | |
| CAA | GAA | GTT | TAT | CCA | GAA | GCC | AAT | GCA | CCC | ATT | GGA | CAT | AAC | CGG | GAA | 1300 |

```
Gln Glu Val Tyr Pro Glu Ala Asn Ala Pro Ile Gly His Asn Arg Glu
390                 395                 400                 405

TCC TAC ATG GTT CCT TTT ATA CCA CTG TAC AGA AAT GGT GAT TTC TTT    1348
Ser Tyr Met Val Pro Phe Ile Pro Leu Tyr Arg Asn Gly Asp Phe Phe
            410                 415                 420

ATT TCA TCC AAA GAT CTG GGC TAT GAC TAT AGC TAT CTA CAA GAT TCA    1396
Ile Ser Ser Lys Asp Leu Gly Tyr Asp Tyr Ser Tyr Leu Gln Asp Ser
            425                 430                 435

GAC CCA GAC TCT TTT CAA GAC TAC ATT AAG TCC TAT TTG GAA CAA GCG    1444
Asp Pro Asp Ser Phe Gln Asp Tyr Ile Lys Ser Tyr Leu Glu Gln Ala
        440                 445                 450

AGT CGG ATC TGG TCA TGG CTC CTT GGG GCG GCG ATG GTA GGG GCC GTC    1492
Ser Arg Ile Trp Ser Trp Leu Leu Gly Ala Ala Met Val Gly Ala Val
    455                 460                 465

CTC ACT GCC CTG CTG GCA GGG CCT GTG AGC TTG CTG TGT CGT CAC AAG    1540
Leu Thr Ala Leu Leu Ala Gly Pro Val Ser Leu Leu Cys Arg His Lys
470                 475                 480                 485

AGA AAG CAG CTT CCT GAA GAA AAG CAG CCA CTC CTC ATG GAG AAA GAG    1588
Arg Lys Gln Leu Pro Glu Glu Lys Gln Pro Leu Leu Met Glu Lys Glu
                490                 495                 500

GAT TAC CAC AGC TTG TAT CAG AGC CAT TTA TAA AAAGGCTTAG GCAATAGAGT  1641
Asp Tyr His Ser Leu Tyr Gln Ser His Leu *
            505                 510

AGGGCCAAAA AGCCTGACCT CACTCTAACT CAAAGTAATG TCCAGGTTCC CAGAGAATAT  1701

CTGCTGGTAT TTTCTGTAAA GACCATTTGC AAAATTGTAA CCTAATACAA AGTGTAGCCT  1761

TCTTCCAACT CAGGTAGAAC ACACCTGTCT TTGTCTTGCT GTTTCACTC  AGCCCTTTTA  1821

ACATTTTCCC CTAAGCCCAT ATGTCTAAGG AAAGGATGCT ATTTGGTAAT GAGGAACTGT  1881

TATTTGTATG TGAATTAAAA GTGCTCTTAT TTTAAAAAA                        1920

( 2 ) INFORMATION FOR SEQ ID NO:8:

( i ) SEQUENCE CHARACTERISTICS:
            ( A ) LENGTH: 529 amino acids
            ( B ) TYPE: amino acid
            ( D ) TOPOLOGY: linear ( i i ) MOLECULE TYPE: protein ( x i ) SEQUENCE DESCRIPTION: SEQ ID NO:8:

Met Leu Leu Ala Val Leu Tyr Cys Leu Leu Trp Ser Phe Gln Thr Ser
-18         -15                 -10                 -5

Ala Gly His Phe Pro Arg Ala Cys Val Ser Ser Lys Asn Leu Met Glu
        1               5                   10

Lys Glu Cys Cys Pro Pro Trp Ser Gly Asp Arg Ser Pro Cys Gly Gln
15              20                  25                  30

Leu Ser Gly Arg Gly Ser Cys Gln Asn Ile Leu Leu Ser Asn Ala Pro
                35                  40                  45

Leu Gly Pro Gln Phe Pro Phe Thr Gly Val Asp Asp Arg Glu Ser Trp
            50                  55                  60

Pro Ser Val Phe Tyr Asn Arg Thr Cys Gln Cys Ser Gly Asn Phe Met
        65                  70                  75

Gly Phe Asn Cys Gly Asn Cys Lys Phe Gly Phe Trp Gly Pro Asn Cys
    80                  85                  90

Thr Glu Arg Arg Leu Leu Val Arg Arg Asn Ile Phe Asp Leu Ser Ala
95                  100                 105                 110

Pro Glu Lys Asp Lys Phe Phe Ala Tyr Leu Thr Leu Ala Lys His Thr
                115                 120                 125
```

| | | | | | | | | | | | | | |
|---|---|---|---|---|---|---|---|---|---|---|---|---|---|
|Ile|Ser|Ser|Asp|Tyr|Val|Ile|Pro|Ile|Gly|Thr|Tyr|Gly|Gln|Met|Lys|
| | | |130| | | |135| | | |140| |
|Asn|Gly|Ser|Thr|Pro|Met|Phe|Asn|Asp|Ile|Asn|Ile|Tyr|Asp|Leu|Phe|
| | |145| | | |150| | | |155| | |
|Val|Trp|Met|His|Tyr|Tyr|Val|Ser|Met|Asp|Ala|Leu|Leu|Gly|Gly|Tyr|
| |160| | | |165| | | |170| | | |
|Glu|Ile|Trp|Arg|Asp|Ile|Asp|Phe|Ala|His|Glu|Ala|Pro|Ala|Phe|Leu|
|175| | | |180| | | |185| | | |190|
|Pro|Trp|His|Arg|Leu|Phe|Leu|Leu|Arg|Trp|Glu|Gln|Glu|Ile|Gln|Lys|
| | | |195| | | |200| | | |205| |
|Leu|Thr|Gly|Asp|Glu|Asn|Phe|Thr|Ile|Pro|Tyr|Trp|Asp|Trp|Arg|Asp|
| | |210| | | |215| | | |220| | |
|Ala|Glu|Lys|Cys|Asp|Ile|Cys|Thr|Asp|Glu|Tyr|Met|Gly|Gly|Gln|His|
| |225| | | |230| | | |235| | | |
|Pro|Thr|Asn|Pro|Ser|Leu|Leu|Ser|Pro|Ala|Ser|Phe|Phe|Ser|Ser|Trp|
|240| | | |245| | | |250| | | | |
|Gln|Ile|Val|Cys|Thr|Arg|Leu|Glu|Glu|Tyr|Asn|Ser|His|Gln|Ser|Leu|
|255| | | |260| | | |265| | | |270|
|Cys|Asn|Gly|Thr|Pro|Glu|Gly|Pro|Leu|Arg|Arg|Asn|Pro|Gly|Asn|His|
| | | |275| | | |280| | | |285| |
|Asp|Lys|Ser|Thr|Thr|Pro|Arg|Leu|Pro|Ser|Ser|Ala|Asp|Val|Glu|Phe|
| | |290| | | |295| | | |300| | |
|Cys|Leu|Ser|Leu|Thr|Gln|Tyr|Glu|Ser|Gly|Ser|Met|Asp|Lys|Ala|Ala|
| |305| | | |310| | | |315| | | |
|Asn|Phe|Ser|Phe|Arg|Asn|Thr|Leu|Glu|Gly|Phe|Ala|Ser|Pro|Leu|Thr|
|320| | | |325| | | |330| | | | |
|Gly|Ile|Ala|Asp|Ala|Ser|Gln|Ser|Ser|Met|His|Asn|Ala|Leu|His|Ile|
|335| | | |340| | | |345| | | |350|
|Tyr|Met|Asn|Gly|Thr|Met|Ser|Gln|Val|Gln|Gly|Ser|Ala|Asn|Asp|Pro|
| | | |355| | | |360| | | |365| |
|Ile|Phe|Leu|Leu|His|His|Ala|Phe|Val|Asp|Ser|Ile|Phe|Glu|Gln|Trp|
| | |370| | | |375| | | |380| | |
|Leu|Gln|Arg|His|Arg|Pro|Leu|Gln|Glu|Val|Tyr|Pro|Glu|Ala|Asn|Ala|
| | |385| | | |390| | | |395| | |
|Pro|Ile|Gly|His|Asn|Arg|Glu|Ser|Tyr|Met|Val|Pro|Phe|Ile|Pro|Leu|
| |400| | | |405| | | |410| | | |
|Tyr|Arg|Asn|Gly|Asp|Phe|Phe|Ile|Ser|Ser|Lys|Asp|Leu|Gly|Tyr|Asp|
|415| | | |420| | | |425| | | |430|
|Tyr|Ser|Tyr|Leu|Gln|Asp|Ser|Asp|Pro|Asp|Ser|Phe|Gln|Asp|Tyr|Ile|
| | |435| | | |440| | | |445| |
|Lys|Ser|Tyr|Leu|Glu|Gln|Ala|Ser|Arg|Ile|Trp|Ser|Trp|Leu|Leu|Gly|
| |450| | | |455| | | |460| | | |
|Ala|Ala|Met|Val|Gly|Ala|Val|Leu|Thr|Ala|Leu|Leu|Ala|Gly|Pro|Val|
| |465| | | |470| | | |475| | | |
|Ser|Leu|Leu|Cys|Arg|His|Lys|Arg|Lys|Gln|Leu|Pro|Glu|Glu|Lys|Gln|
| |480| | | |485| | | |490| | | |
|Pro|Leu|Leu|Met|Glu|Lys|Glu|Asp|Tyr|His|Ser|Leu|Tyr|Gln|Ser|His|
|495| | | |500| | | |505| | | |510|
|Leu| | | | | | | | | | | | | |

( 2 ) INFORMATION FOR SEQ ID NO:9:

( i ) SEQUENCE CHARACTERISTICS:
        ( A ) LENGTH: 1558 base pairs
        ( B ) TYPE: nucleic acid ( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 32..1558

( i x ) FEATURE:
( A ) NAME/KEY: mat_peptide
( B ) LOCATION: 86..1555

( i x ) FEATURE:
( A ) NAME/KEY: sig_peptide
( B ) LOCATION: 32..85

( x ) PUBLICATION INFORMATION:
( A ) AUTHORS: Chintamaneni, Chaya D
Halaban, Ruth
Kobayashi, Yvonne
Witkop, Carl J
Kwon, Byoung Se
( B ) TITLE: A single base insertion in the putative
transmembrane domain of the tyrosinase gene as a
cause for tyrosinase-negative oculocutaneous
albinism
( C ) JOURNAL: Proc. Natl. Acad. Sci. U.S.A.
( D ) VOLUME: 88
( F ) PAGES: 5272-5276
( G ) DATE: June-1991

( x i ) SEQUENCE DESCRIPTION: SEQ ID NO:9:

```
TCCTGCAGAC CTTGTGAGGA CTAGAGGAAG A ATG CTC CTG GCT GTT TTG TAC          52
                                    Met Leu Leu Ala Val Leu Tyr
                                    -18              -15

TGC CTG CTG TGG AGT TTC CAG ACC TCC GCT GGC CAT TTC CCT AGA GCC        100
Cys Leu Leu Trp Ser Phe Gln Thr Ser Ala Gly His Phe Pro Arg Ala
-10             -5                       1                5

TGT GTC TCC TCT AAG AAC CTG ATG GAG AAG GAA TGC TGT CCA CCG TGG        148
Cys Val Ser Ser Lys Asn Leu Met Glu Lys Glu Cys Cys Pro Pro Trp
            10              15                      20

AGC GGG GAC AGG AGT CCC TGT GGC CAG CTT TCA GGC AGA GGT TCC TGT        196
Ser Gly Asp Arg Ser Pro Cys Gly Gln Leu Ser Gly Arg Gly Ser Cys
        25              30              35

CAG AAT ATC CTT CTG TCC AAT GCA CCA CTT GGG CCT CAA TTT CCC TTC        244
Gln Asn Ile Leu Leu Ser Asn Ala Pro Leu Gly Pro Gln Phe Pro Phe
        40              45              50

ACA GGG GTG GAT GAC CGG GAG TCG TGG CCT TCC GTC TTT TAT AAT AGG        292
Thr Gly Val Asp Asp Arg Glu Ser Trp Pro Ser Val Phe Tyr Asn Arg
    55              60              65

ACC TGC CAG TGC TCT GGC AAC TTC ATG GGA TTC AAC TGT GGA AAC TGC        340
Thr Cys Gln Cys Ser Gly Asn Phe Met Gly Phe Asn Cys Gly Asn Cys
70              75              80              85

AAG TTT GGC TTT TGG GGA CCA AAC TGC ACA GAG AGA CGA CTC TTG GTG        388
Lys Phe Gly Phe Trp Gly Pro Asn Cys Thr Glu Arg Arg Leu Leu Val
                90              95              100

AGA AGA AAC ATC TTC GAT TTG AGT GCC CCA GAG AAG GAC AAA TTT TTT        436
Arg Arg Asn Ile Phe Asp Leu Ser Ala Pro Glu Lys Asp Lys Phe Phe
            105             110             115

GCC TAC CTC ACT TTA GCA AAG CAT ACC ATC AGC TCA GAC TAT GTC ATC        484
Ala Tyr Leu Thr Leu Ala Lys His Thr Ile Ser Ser Asp Tyr Val Ile
        120             125             130

CCC ATA GGG ACC TAT GGC CAA ATG AAA AAT GGA TCA ACA CCC ATA TTT        532
Pro Ile Gly Thr Tyr Gly Gln Met Lys Asn Gly Ser Thr Pro Ile Phe
    135             140             145

AAC GAC ATC AAT ATT TAT GAC CTC TTT GTC TGG ATG CAT TAT TAT GTG        580
Asn Asp Ile Asn Ile Tyr Asp Leu Phe Val Trp Met His Tyr Tyr Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 150 |     |     |     |     | 155 |     |     |     |     | 160 |     |     |     |     | 165 |      |
| TCA | ATG | GAT | GCA | CTG | CTT | GGG | GGA | TCT | GAA | ATC | TGG | AGA | GAC | ATT | GAT | 628  |
| Ser | Met | Asp | Ala | Leu | Leu | Gly | Gly | Ser | Glu | Ile | Trp | Arg | Asp | Ile | Asp |      |
|     |     |     | 170 |     |     |     |     | 175 |     |     |     |     | 180 |     |     |      |
| TTT | GCC | CAT | GAA | GCA | CCA | GCT | TTT | CTG | CCT | TGG | CAT | AGA | CTC | TTC | TTG | 676  |
| Phe | Ala | His | Glu | Ala | Pro | Ala | Phe | Leu | Pro | Trp | His | Arg | Leu | Phe | Leu |      |
|     |     |     | 185 |     |     |     |     | 190 |     |     |     |     | 195 |     |     |      |
| TTG | CGG | TGG | GAA | CAA | GAA | ATC | CAG | AAG | CTG | ACA | GGA | GAT | GAA | AAC | TTC | 724  |
| Leu | Arg | Trp | Glu | Gln | Glu | Ile | Gln | Lys | Leu | Thr | Gly | Asp | Glu | Asn | Phe |      |
|     |     | 200 |     |     |     |     | 205 |     |     |     |     | 210 |     |     |     |      |
| ACT | ATT | CCA | TAT | TGG | GAC | TGG | CGG | GAT | GCA | GAA | AAG | TGT | GAC | ATT | TGC | 772  |
| Thr | Ile | Pro | Tyr | Trp | Asp | Trp | Arg | Asp | Ala | Glu | Lys | Cys | Asp | Ile | Cys |      |
|     | 215 |     |     |     |     | 220 |     |     |     |     | 225 |     |     |     |     |      |
| ACA | GAT | GAG | TAC | ATG | GGA | GGT | CAG | CAC | CCC | ACA | AAT | CCT | AGC | TTA | CTC | 820  |
| Thr | Asp | Glu | Tyr | Met | Gly | Gly | Gln | His | Pro | Thr | Asn | Pro | Ser | Leu | Leu |      |
| 230 |     |     |     |     | 235 |     |     |     |     | 240 |     |     |     |     | 245 |      |
| AGC | CCA | GCA | TCA | TTC | TTC | TCC | TCT | TGG | CAG | ATT | GTC | TGT | ACC | CGA | TTG | 868  |
| Ser | Pro | Ala | Ser | Phe | Phe | Ser | Ser | Trp | Gln | Ile | Val | Cys | Thr | Arg | Leu |      |
|     |     |     |     | 250 |     |     |     |     | 255 |     |     |     |     | 260 |     |      |
| GAG | GAG | TAC | AAC | AGC | CAT | CAG | TCT | TTA | TGC | AAT | GGA | ACG | CCC | GAG | GGA | 916  |
| Glu | Glu | Tyr | Asn | Ser | His | Gln | Ser | Leu | Cys | Asn | Gly | Thr | Pro | Glu | Gly |      |
|     |     |     | 265 |     |     |     |     | 270 |     |     |     |     | 275 |     |     |      |
| CCT | TTA | CGG | CGT | AAT | CCT | GGA | AAC | CAT | GAC | AAA | TCC | AGA | ACC | CCA | AGG | 964  |
| Pro | Leu | Arg | Arg | Asn | Pro | Gly | Asn | His | Asp | Lys | Ser | Arg | Thr | Pro | Arg |      |
|     |     | 280 |     |     |     |     | 285 |     |     |     |     | 290 |     |     |     |      |
| CTC | CCC | TCT | TCA | GCT | GAT | GTA | GAA | TTT | TGC | CTG | AGT | TTG | ACC | CAA | TAT | 1012 |
| Leu | Pro | Ser | Ser | Ala | Asp | Val | Glu | Phe | Cys | Leu | Ser | Leu | Thr | Gln | Tyr |      |
|     | 295 |     |     |     |     | 300 |     |     |     |     | 305 |     |     |     |     |      |
| GAA | TCT | GGT | TCC | ATG | GAT | AAA | GCT | GCC | AAT | TTC | AGC | TTT | AGA | AAT | ACA | 1060 |
| Glu | Ser | Gly | Ser | Met | Asp | Lys | Ala | Ala | Asn | Phe | Ser | Phe | Arg | Asn | Thr |      |
| 310 |     |     |     |     | 315 |     |     |     |     | 320 |     |     |     |     | 325 |      |
| CTG | GAA | GGA | TTT | GCT | AGT | CCA | CTT | ACT | GGG | ATA | GCG | GAT | GCC | TCT | CAA | 1108 |
| Leu | Glu | Gly | Phe | Ala | Ser | Pro | Leu | Thr | Gly | Ile | Ala | Asp | Ala | Ser | Gln |      |
|     |     |     |     | 330 |     |     |     |     | 335 |     |     |     |     | 340 |     |      |
| AGC | AGC | ATG | CAC | AAT | GCC | TTG | CAC | ATC | TAT | ATG | AAT | GGA | ACA | ATG | TCC | 1156 |
| Ser | Ser | Met | His | Asn | Ala | Leu | His | Ile | Tyr | Met | Asn | Gly | Thr | Met | Ser |      |
|     |     |     | 345 |     |     |     |     | 350 |     |     |     |     | 355 |     |     |      |
| CAG | GTA | CAG | GGA | TCT | GCC | AAC | GAT | CCT | ATC | TTC | CTT | CTT | CAC | CAT | GCA | 1204 |
| Gln | Val | Gln | Gly | Ser | Ala | Asn | Asp | Pro | Ile | Phe | Leu | Leu | His | His | Ala |      |
|     |     | 360 |     |     |     |     | 365 |     |     |     |     | 370 |     |     |     |      |
| TTT | GTT | GAC | AGT | ATT | TTT | GAG | CAG | TGG | CTC | CGA | AGG | CAC | CGT | CCT | CTT | 1252 |
| Phe | Val | Asp | Ser | Ile | Phe | Glu | Gln | Trp | Leu | Arg | Arg | His | Arg | Pro | Leu |      |
|     | 375 |     |     |     |     | 380 |     |     |     |     | 385 |     |     |     |     |      |
| CAA | GAA | GTT | TAT | CCA | GAA | GCC | AAT | GCA | CCC | ATT | GGA | CAT | AAC | CGG | GAA | 1300 |
| Gln | Glu | Val | Tyr | Pro | Glu | Ala | Asn | Ala | Pro | Ile | Gly | His | Asn | Arg | Glu |      |
| 390 |     |     |     |     | 395 |     |     |     |     | 400 |     |     |     |     | 405 |      |
| TCC | TAC | ATG | GTT | CCT | TTT | ATA | CCA | CTG | TAC | AGA | AAT | GGT | GAT | TTC | TTT | 1348 |
| Ser | Tyr | Met | Val | Pro | Phe | Ile | Pro | Leu | Tyr | Arg | Asn | Gly | Asp | Phe | Phe |      |
|     |     |     |     | 410 |     |     |     |     | 415 |     |     |     |     | 420 |     |      |
| ATT | TCA | TCC | AAA | GAT | CTG | GGC | TAT | GAC | TAT | AGC | TAT | CTA | CAA | GAT | TCA | 1396 |
| Ile | Ser | Ser | Lys | Asp | Leu | Gly | Tyr | Asp | Tyr | Ser | Tyr | Leu | Gln | Asp | Ser |      |
|     |     |     | 425 |     |     |     |     | 430 |     |     |     |     | 435 |     |     |      |
| GAC | CCA | GAC | TCT | TTT | CAA | GAC | TAC | ATT | AAG | TCC | TAT | TTG | GAA | CAA | GCG | 1444 |
| Asp | Pro | Asp | Ser | Phe | Gln | Asp | Tyr | Ile | Lys | Ser | Tyr | Leu | Glu | Gln | Ala |      |
|     |     | 440 |     |     |     |     | 445 |     |     |     |     | 450 |     |     |     |      |
| AGT | CGG | ATC | TGG | TCA | TGG | CTC | CTT | GGG | GCG | GCG | ATG | GTA | GGG | GCC | GTC | 1492 |
| Ser | Arg | Ile | Trp | Ser | Trp | Leu | Leu | Gly | Ala | Ala | Met | Val | Gly | Ala | Val |      |
|     | 455 |     |     |     |     | 460 |     |     |     |     | 465 |     |     |     |     |      |
| CTC | ACT | TGC | CCT | GCT | GGC | AGG | GCT | TGT | GAG | CTT | GCT | GTG | TCG | TCA | CAA | 1540 |
| Leu | Thr | Cys | Pro | Ala | Gly | Arg | Ala | Cys | Glu | Leu | Ala | Val | Ser | Ser | Gln |      |

```
470                    475                   480                   485

GAG  AAA  GCA  GCT  TCC  TGA                                                              1558
Glu  Lys  Ala  Ala  Ser  *
                    490
```

( 2 ) INFORMATION FOR SEQ ID NO:10:

( i ) SEQUENCE CHARACTERISTICS:
      ( A ) LENGTH: 508 amino acids
      ( B ) TYPE: amino acid
      ( D ) TOPOLOGY: linear ( i i ) MOLECULE TYPE: protein ( x i ) SEQUENCE DESCRIPTION: SEQ ID NO:10:

```
Met  Leu  Leu  Ala  Val  Leu  Tyr  Cys  Leu  Leu  Trp  Ser  Phe  Gln  Thr  Ser
-18            -15                 -10                      -5

Ala  Gly  His  Phe  Pro  Arg  Ala  Cys  Val  Ser  Ser  Lys  Asn  Leu  Met  Glu
          1                   5                       10

Lys  Glu  Cys  Cys  Pro  Pro  Trp  Ser  Gly  Asp  Arg  Ser  Pro  Cys  Gly  Gln
15                       20                  25                            30

Leu  Ser  Gly  Arg  Gly  Ser  Cys  Gln  Asn  Ile  Leu  Leu  Ser  Asn  Ala  Pro
               35                       40                            45

Leu  Gly  Pro  Gln  Phe  Pro  Phe  Thr  Gly  Val  Asp  Asp  Arg  Glu  Ser  Trp
               50                       55                       60

Pro  Ser  Val  Phe  Tyr  Asn  Arg  Thr  Cys  Gln  Cys  Ser  Gly  Asn  Phe  Met
          65                       70                       75

Gly  Phe  Asn  Cys  Gly  Asn  Cys  Lys  Phe  Gly  Phe  Trp  Gly  Pro  Asn  Cys
          80                       85                       90

Thr  Glu  Arg  Arg  Leu  Leu  Val  Arg  Arg  Asn  Ile  Phe  Asp  Leu  Ser  Ala
95                       100                      105                     110

Pro  Glu  Lys  Asp  Lys  Phe  Phe  Ala  Tyr  Leu  Thr  Leu  Ala  Lys  His  Thr
                    115                      120                     125

Ile  Ser  Ser  Asp  Tyr  Val  Ile  Pro  Ile  Gly  Thr  Tyr  Gly  Gln  Met  Lys
               130                      135                     140

Asn  Gly  Ser  Thr  Pro  Ile  Phe  Asn  Asp  Ile  Asn  Ile  Tyr  Asp  Leu  Phe
          145                      150                     155

Val  Trp  Met  His  Tyr  Tyr  Val  Ser  Met  Asp  Ala  Leu  Leu  Gly  Gly  Ser
     160                      165                     170

Glu  Ile  Trp  Arg  Asp  Ile  Asp  Phe  Ala  His  Glu  Ala  Pro  Ala  Phe  Leu
175                      180                      185                     190

Pro  Trp  His  Arg  Leu  Phe  Leu  Leu  Arg  Trp  Glu  Gln  Glu  Ile  Gln  Lys
                    195                      200                     205

Leu  Thr  Gly  Asp  Glu  Asn  Phe  Thr  Ile  Pro  Tyr  Trp  Asp  Trp  Arg  Asp
               210                      215                     220

Ala  Glu  Lys  Cys  Asp  Ile  Cys  Thr  Asp  Glu  Tyr  Met  Gly  Gly  Gln  His
          225                      230                     235

Pro  Thr  Asn  Pro  Ser  Leu  Leu  Ser  Pro  Ala  Ser  Phe  Phe  Ser  Ser  Trp
     240                      245                     250

Gln  Ile  Val  Cys  Thr  Arg  Leu  Glu  Glu  Tyr  Asn  Ser  His  Gln  Ser  Leu
255                      260                      265                     270

Cys  Asn  Gly  Thr  Pro  Glu  Gly  Pro  Leu  Arg  Arg  Asn  Pro  Gly  Asn  His
               275                      280                     285

Asp  Lys  Ser  Arg  Thr  Pro  Arg  Leu  Pro  Ser  Ser  Ala  Asp  Val  Glu  Phe
               290                      295                     300

Cys  Leu  Ser  Leu  Thr  Gln  Tyr  Glu  Ser  Gly  Ser  Met  Asp  Lys  Ala  Ala
          305                      310                     315
```

```
Asn  Phe  Ser  Phe  Arg  Asn  Thr  Leu  Glu  Gly  Phe  Ala  Ser  Pro  Leu  Thr
     320                 325                 330

Gly  Ile  Ala  Asp  Ala  Ser  Gln  Ser  Ser  Met  His  Asn  Ala  Leu  His  Ile
335                      340                 345                           350

Tyr  Met  Asn  Gly  Thr  Met  Ser  Gln  Val  Gln  Gly  Ser  Ala  Asn  Asp  Pro
                    355                 360                           365

Ile  Phe  Leu  Leu  His  His  Ala  Phe  Val  Asp  Ser  Ile  Phe  Glu  Gln  Trp
               370                      375                      380

Leu  Arg  Arg  His  Arg  Pro  Leu  Gln  Glu  Val  Tyr  Pro  Glu  Ala  Asn  Ala
          385                      390                 395

Pro  Ile  Gly  His  Asn  Arg  Glu  Ser  Tyr  Met  Val  Pro  Phe  Ile  Pro  Leu
     400                      405                      410

Tyr  Arg  Asn  Gly  Asp  Phe  Phe  Ile  Ser  Ser  Lys  Asp  Leu  Gly  Tyr  Asp
415                      420                      425                      430

Tyr  Ser  Tyr  Leu  Gln  Asp  Ser  Asp  Pro  Asp  Ser  Phe  Gln  Asp  Tyr  Ile
               435                      440                      445

Lys  Ser  Tyr  Leu  Glu  Gln  Ala  Ser  Arg  Ile  Trp  Ser  Trp  Leu  Leu  Gly
               450                      455                 460

Ala  Ala  Met  Val  Gly  Ala  Val  Leu  Thr  Cys  Pro  Ala  Gly  Arg  Ala  Cys
          465                      470                      475

Glu  Leu  Ala  Val  Ser  Ser  Gln  Glu  Lys  Ala  Ala  Ser
     480                 485                 490
```

( 2 ) INFORMATION FOR SEQ ID NO:11:

( i ) SEQUENCE CHARACTERISTICS:
        ( A ) LENGTH: 2397 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:11:

```
TAGACTGTTG  AGTACAACAC  GTGTAGGCCA  GAGGAGACAG  TGGCCTATAC  TTGGGACAAA      60
TAAAGAGGTC  TGTCCTATTT  AAGAAAATCA  ACCCTGTAAA  GGAAATTAAT  AGGACTAAGT     120
ACATTTTAGT  AAGGCCTCTA  AGCAGGCTCT  AAAGATTATG  AAAAATACAC  GGGACAGCAG     180
ACACAAAAGC  CCTTAAAGAG  CATGAAGACT  TTCTAAGTTA  TTTCACTGGA  AGCCTGATAG     240
TGGGGCAAGT  GTAAGGCAAA  ATTCTTAATT  AAATTGAAAA  TGATAAGTTG  AATTCTGTCT     300
TCGAGAACAT  AGAAAAGAAT  TATGAAATCC  CAACATGTGG  TTACAAGTAA  TGCAGACCCA     360
AGGCTCCCCA  GGGACAAGAA  GTCTTGTGTT  AACTCTTTGT  GGCTCTGAAA  GAAAGAGAGA     420
GAGAAAAGAT  TAAGCGTCCT  TGTGGAGATC  ATGTGATGAC  TTCCTGATTC  AGCCAGAGC      480
GAGCATTTCC  ATGGAAACTT  CTCTTCCTCT  TCACCCACAC  ACTGCTCCAT  GTACCTGCAA     540
AGCCTGTTCT  GTCTCAAAAA  AGTTGTTTGG  ATGAGCCGTG  ACTTTTTTTT  TTCTTAAATA     600
ATGAGACAAA  CTCCAGAAAA  AGAGAAAAAA  GCAGAGCACT  CTGACATTCC  CGCATCATCG     660
AAATAGTGAT  GGCTTTTCCT  AGAATGCTTC  AGCTAAGGAC  CCAAAATACT  AATGATCTCC     720
TCAAAGCTTC  AGAGGGGCAA  CTTTGATTTG  ACTACTCTTT  TTGTCACTCT  TCAGCTCACA     780
AAAGAGCTCA  CTTTAGTTCA  AAACACAAAG  CTTAAGCCC   CTCCATAGAT  TGGTCCAGGT     840
TTAATTTTCT  ATGATGAGTG  GAGGCCTCAG  TTTAATGCTC  CAACTTGATA  GATGAAACAC     900
AGTTCCCTCC  TCTACACATT  TCCCCTGACT  CAGGAGTTTG  TATATATTCT  CAGTTGTCTG     960
TCCAACTTAT  GCCCACTCTT  TGAGATATTA  ATCAAGGCAC  TCCCTTGATA  ACACTTGCAT    1020
```

```
ATTATTATCA   AAATTATGCA   ATTCTTTCTA   ATATCAGCCC   ACAAATACAT   CTCTTCCATT    1080
AAAAGTTTGA   CTAATTATCT   ATACTACTCA   TTTGAAAACT   AACATAGTTA   AGTTGTATTT    1140
TTAGCCATGA   ATTTCAGTTT   CCCTAGCTCA   CTATACACAG   AGAAGGAAAC   TTTTGAAATA    1200
ATTGAGATGA   TCAAAATAT    TTGCTGAAGT   AAATATATTT   CTCCTTTTCA   TTCACTCACT    1260
AATTGAGAAT   GTCTTTGCAC   AAAACACATT   GCAAAACAT    TTTCAAAAAA   ATTCCTAATT    1320
TCTAGAATTG   ATAGGAAAAA   CAATATGGCT   ACAGCATTGG   AGAGAGAGAG   AAAGGAAGAG    1380
GAGAAAGGAG   AGAGAGAGAA   AGGAGAGAGG   AGAGAGACAG   AGGAGAGAGA   GAGAGGATAG    1440
AGGGGGAGAG   AGAGAGAAGA   GACACAGAGG   AGAGAGAGAG   AGGATAGAGG   GGAGAGAGAG    1500
GGAGAGGGAG   AGAGAGGGAG   AGAGAGGGAG   AGAGAGAGAG   AGAGAGGGAG   AGAGAGAGAG    1560
AAAGAGAGAG   AGAGGGAGAG   AGAGAGAGAG   AGCTCTTTAA   CGTGAGATAT   CCCACAATGA    1620
ACAAATCTGC   CCAGTTATCA   AAGTGCAGCT   ATCCTTAGGA   GTTGTCAGAA   AATGCATCAG    1680
GATTATCAGA   GAAAAGTATC   AGAAAGATTT   TTTTTCTGA    TACGTTGTAT   AAAATAAACA    1740
AACTGAAATT   CAATAACATA   TAAGGAATTC   TGTCTGGGCT   CTGAAGACAA   TCTCTCTCTG    1800
CATATTGAGT   TCTTCAAACA   TTGTAGCCTC   TTTATGGTCT   CTGAGAAATA   ACTACCTTAA    1860
ACCCATAATC   TTTAATACTT   CCTAAACTTT   CTTAATAAGA   GAAGCTCTAT   TCCTGACACT    1920
ACCTCTCATT   TGCAAGGTCA   AATCATCATT   AGTTTGTAG    TCTATTAACT   GGGTTTGCTT    1980
AGGTCAGGCA   TTATTATTAC   TAACCTTATT   GTTAATATTC   TAACCATAAG   AATTAAACTA    2040
TTAATGGTGA   ATAGAGTTTT   TCACTTTAAC   ATAGGCCTAT   CCCACTGGTG   GGATACGAGC    2100
CAATTCGAAA   GAAAAGTCA    GTCATGTGCT   TTTCAGAGGA   TGAAAGCTTA   AGATAAAGAC    2160
TAAAAGTGTT   TGATGCTGGA   GGTGGGAGTG   GTATTATATA   GGTCTCAGCC   AAGACATGTG    2220
ATAATCACTG   TAGTAGTAGC   TGGAAAGAGA   AATCTGTGAC   TCCAATTAGC   CAGTTCCTGC    2280
AGACCTTGTG   AGGACTAGAG   GAAGAATGCT   CCTGGCTGTT   TTGTACTGCC   TGCTGTGGAG    2340
TTTCCAGACC   TCCGCTGGCC   ATTTCCCTAG   AGCCTGTGTC   TCCTCTAAGA   ACCTGAT       2397
```

( 2 ) INFORMATION FOR SEQ ID NO:12:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc ="oligo fragment"

( x i ) SEQUENCE DESCRIPTION: SEQ ID NO:12:

```
TGATGTATTC   TTGATACTAC   T                                                    21
```

( 2 ) INFORMATION FOR SEQ ID NO:13:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc ="oligo fragment"

( x i ) SEQUENCE DESCRIPTION: SEQ ID NO:13:

```
GCTGTAGCCA   TATTGT                                                            16
```

-continued (2) INFORMATION FOR SEQ ID NO:14:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="oligo fragment"

(xi) SEQUENCE DESCRIPTION: SEQ ID NO:14:

TGGTGGGCTG ATATTA        16

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="oligo fragment"

(xi) SEQUENCE DESCRIPTION: SEQ ID NO:15:

GAAATGGCCA GGGGAGG        17

(2) INFORMATION FOR SEQ ID NO:16:

(i) SEQUENCE CHARACTERISTICS:
        (A) LENGTH: 95 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

```
Pro Arg Gln Cys Ala Thr Val Glu Ala Leu Arg Ser Gly Met Cys Cys
 1               5                  10                      15
Pro Asp Leu Ser Pro Val Ser Gly Pro Gly Thr Asp Arg Cys Gly Ser
             20              25                  30
Ser Ser Gly Arg Gly Arg Cys Glu Ala Val Thr Gln Arg Val Leu Ile
         35              40                  45
Ser Thr Glu Asp Gly Pro Ile Arg Arg Asn Pro Ala Gly Asn Arg Pro
     50              55                  60
Met Val Gln Arg Leu Pro Glu Pro Gln Asp Val Asp Glu Ala Asn Gln
 65              70                  75                      80
Pro Leu Leu Thr Asp Gln Tyr Gln Cys Tyr Ala Glu Glu Arg Ile
             85              90                  95
```